(12) United States Patent
Zhi

(10) Patent No.: US 11,427,550 B2
(45) Date of Patent: Aug. 30, 2022

(54) 5-FLUOROURACIL COMPOUNDS

(71) Applicant: NUCORION PHARMACEUTICALS, INC., San Diego, CA (US)

(72) Inventor: Lin Zhi, Austin, TX (US)

(73) Assignee: NUCORION PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 16/930,123

(22) Filed: Jul. 15, 2020

(65) Prior Publication Data

US 2020/0399227 A1 Dec. 24, 2020

Related U.S. Application Data

(63) Continuation-in-part of application No. PCT/US2019/014080, filed on Jan. 17, 2019.

(60) Provisional application No. 62/619,557, filed on Jan. 19, 2018, provisional application No. 62/875,190, filed on Jul. 17, 2019.

(51) Int. Cl.
| | |
|---|---|
| *A01N 43/04* | (2006.01) |
| *A61K 31/70* | (2006.01) |
| *C07D 239/553* | (2006.01) |
| *C07H 19/10* | (2006.01) |
| *C07H 19/06* | (2006.01) |
| *A61P 1/16* | (2006.01) |

(52) U.S. Cl.
CPC .......... *C07D 239/553* (2013.01); *A61P 1/16* (2018.01); *C07H 19/06* (2013.01); *C07H 19/10* (2013.01)

(58) Field of Classification Search
CPC ....... C07H 21/04; A61P 35/00; A61K 9/0053; A61K 31/7084; C07K 16/082
See application file for complete search history.

(56) References Cited

U.S. PATENT DOCUMENTS

| | | |
|---|---|---|
| 4,401,808 A | 8/1983 | Yamaji et al. |
| 4,689,404 A | 8/1987 | Kawada et al. |
| 4,692,434 A | 9/1987 | Hertel |
| 4,966,891 A | 10/1990 | Morio et al. |
| 5,476,932 A | 12/1995 | Brinkman et al. |
| 6,312,662 B1 | 11/2001 | Erion et al. |
| 7,456,155 B2 | 11/2008 | Sommadossi et al. |
| 8,097,706 B2 | 1/2012 | Lee et al. |
| 8,603,999 B2 | 12/2013 | Drummond et al. |
| 8,653,048 B2 | 2/2014 | Xue et al. |
| 8,741,858 B2 | 6/2014 | Ren et al. |
| 9,447,137 B2 | 9/2016 | Suo |
| 9,744,186 B2 | 8/2017 | Suo |

(Continued)

FOREIGN PATENT DOCUMENTS

| | | |
|---|---|---|
| CN | 1033183 | 5/1989 |
| CN | 101525361 | 9/2009 |

(Continued)

OTHER PUBLICATIONS

Almarsson et. al., "Crystal Engineering of the Composition of Pharmaceutical Phases. Do Pharmaceutical Co-crystals Represent a New Path to Improved Medicines?" The Royal Society of Chemistry (2004) 1889-1896.

(Continued)

*Primary Examiner* — Patrick T Lewis
(74) *Attorney, Agent, or Firm* — Knobbe, Martens, Olson & Bear, LLP

(57) ABSTRACT

The compounds are of the class of 5-fluorouracil derived acetal and hemiaminal ether compounds, useful in treating liver diseases and various types of cancer. The following formulas are representative of the class of compounds provided herein:

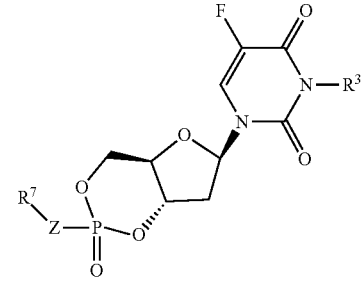

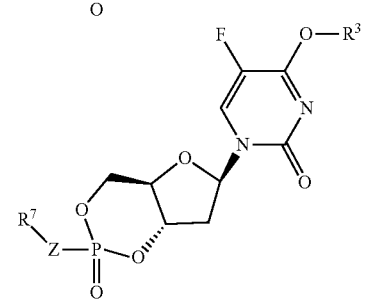

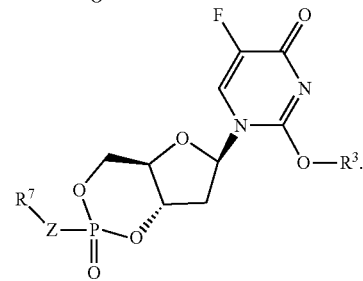

22 Claims, No Drawings

(56) References Cited

U.S. PATENT DOCUMENTS

| | | | |
|---|---|---|---|
| 10,000,521 B2 | 6/2018 | Suo et al. | |
| 10,059,733 B2 | 8/2018 | Suo et al. | |
| 10,435,429 B2* | 10/2019 | Zhi | C07H 19/11 |
| 2009/0069557 A1 | 3/2009 | Palle et al. | |
| 2009/0221524 A1 | 9/2009 | Kotra et al. | |
| 2010/0075917 A1 | 3/2010 | Decout et al. | |
| 2010/0286084 A1 | 11/2010 | Ren et al. | |
| 2011/0183933 A1 | 7/2011 | Guzi et al. | |
| 2012/0009147 A1 | 1/2012 | Cho et al. | |
| 2012/0070411 A1 | 3/2012 | Beigelman et al. | |
| 2012/0088908 A1 | 4/2012 | Xue et al. | |
| 2015/0224208 A1 | 8/2015 | Ueki et al. | |
| 2017/0057981 A1 | 3/2017 | Chen et al. | |
| 2018/0044368 A1 | 2/2018 | Zhi | |
| 2019/0100551 A1 | 4/2019 | Zhi | |
| 2021/0188887 A1 | 6/2021 | Zhi | |

FOREIGN PATENT DOCUMENTS

| | | |
|---|---|---|
| CN | 101875680 | 11/2010 |
| CN | 101921303 s | 12/2010 |
| CN | 102219817 | 10/2011 |
| CN | 106554382 | 4/2017 |
| EP | 0 588 317 | 3/1994 |
| EP | 0 602 454 B1 | 4/1996 |
| EP | 2 423 215 | 2/2012 |
| EP | 2 615 101 | 7/2013 |
| WO | WO 82/000293 | 2/1982 |
| WO | WO 02/12242 | 2/2002 |
| WO | WO 05/018330 | 3/2005 |
| WO | WO 06/065525 | 6/2006 |
| WO | WO 08/030373 | 3/2008 |
| WO | WO 08/083465 | 7/2008 |
| WO | WO 08/144980 | 12/2008 |
| WO | WO 09/082846 | 7/2009 |
| WO | WO 09/106243 | 9/2009 |
| WO | WO 09/152095 | 12/2009 |
| WO | WO 10/027326 | 3/2010 |
| WO | WO 10/056403 | 5/2010 |
| WO | WO 12/031539 | 3/2012 |
| WO | WO 12/040126 | 3/2012 |
| WO | WO 13/142525 | 9/2013 |
| WO | WO 13/177195 | 11/2013 |
| WO | WO 14/043380 | 3/2014 |
| WO | WO 14/074725 | 5/2014 |
| WO | WO 14/124430 | 8/2014 |
| WO | WO 14/145207 | 9/2014 |
| WO | WO 14/204831 | 12/2014 |
| WO | WO 15/081133 | 6/2015 |
| WO | WO 15/134334 | 9/2015 |
| WO | WO 16/138026 | 9/2016 |
| WO | WO 18/091542 | 5/2018 |
| WO | WO 18/113652 | 6/2018 |
| WO | WO 19/027905 | 2/2019 |
| WO | WO 19/169323 | 9/2019 |
| WO | WO 20/219464 | 10/2020 |

OTHER PUBLICATIONS

Bentrude et al., "Efficient Preparation of Cyclc 3',5'-Phosphoramidates and Amidates of Antiviral and Antitumor 5-X-2'-Deoxyuridines (X=H, CH3, I, F, CF3, trans-CH=CHBr)," Nucleosides and Nucleotides (1989) vol. 8, No. 7, pp. 1359-1367.

Beres et al., "An Efficient Synthesis of Certain 5-Substituted-2'-Deoxyuridine 3',5'-Cyclic Monophosphate P—O-Alkyl_Aralkyl) Esters. The Crystal and Molecular Structure of 5-Iodo-2'-Deoxyuridine 3',5'-Cyclic Monophosphate P—O-methyl Ester with Axial Methoxy Group," Tetrahedron (1984) vol. 40, No. 12, pp. 2405-2414.

Beres et al., 1986, Synthesis and antitumor and antiviral properties of 5-halo- and 5-(trifluoromethyl)-2'-deoxyuridine 3',5'-cyclic monophosphates and neutral triesters, J. Med. Chem., 29:1243-1249.

Chen et al., "A Facile One-Pot Synthesis of N4-Alkyloxycarbonyl Cytosine Nucleosides," Synthetic Communications (2004) vol. 34, No. 18, pp. 3273-3279.

Cheng et al., "QSAR Models for Phosphoramidate Prodrugs of 2'-Methylcytidine as Inhibitors of Hepatitis C Virus Based on PSO Boosting," Chem Biol and Drug Design (2011) 78:948-959.

Chou et al., "Analysis of combined drug effects: a new look at a very old problem." Trends Pharmacol Sci (1983) 4:450-454.

Chou et al., "Quantitative analysis of dose-effect relationships: the combined effects of multiple drugs or enzyme inhibitors." Adv Enzyme Regul (1984) 22:27-55.

Chou, T.C., "Theoretical basis, experimental design, and computerized simulation of synergism and antagonism in drug combination studies," Pharmacol Rev. (2006) 58(3):621-81.

Crook et al., "Examining the origin of selectivity in the reaction of racemic alcohols with chiral N-phosphoryl oxazolidinones," (2014) 25:1298-1308.

DeWaziers et al., "Cytochrome P 450 Isoenzymes, Epoxide Hydrolase and Glutathione Transferases in Rat and Human Hepatic and Extraheptaic Tissues," J Pharmacol and Experimental Therapeutics (1990) vol. 253, No. 1, pp. 387-394.

Donghi et al., "Synthesis and evaluation of novel phosphoramidate prodrugs of 2'-methyl cytidine as inhibitors of hepatitis c virus NS5B polymerase," Bioorganic &Medicinal Chem Letters (2009) 19:1392-1395.

Griffiths, 2001, Cytomegalovirus, in Principles and Practice of Clinical Virology, A.J. Zuckerman et al., eds, 5th ed., pp. 85-122.

Imai et al., "Novel cell-based reporter assay system using epitope-tagged protein for the identification of agonistic ligands of constitutive androstane receptor (CAR)," Drug Metab and Phamaco (2013) 28(4):290-298.

Jain et al., "Synthesis and Study of Cyclic Pronucleotides of 5-fluoro-2'-deoxyuridine," Bioorganic and Med Chem Letters (2012) vol. 22, pp. 4497-4501.

Kawaguchi et al., "Specificity of Esterases and Structure of Prodrug Esters. II. Hydrolytic Regeneration Behavior of 5-Fluro-2'-deoxyuridine (FUdR) from 3',5'-Diesters of FUdR with Rat Tissue Homogonates and Plasmain Relation to Their Antitumor Activity," Chem and Pharma Bulletin (1985) vol. 33, No. 4, pp. 1652-1659.

Kotra et al., "Structure-Activity Relationships of 2'-Deoxy-2',2'difluoro-L-erythro-pentofuranosyl Nucleosides," J Med Chem (1997) 40(1):3635-3644.

Kroep et al., "Pretreatment Deoxycytidine Kinase Levels Predict in Vivo Gemcitabine Sensitivity," Mol. Cancer Ther. (2002) 1, 371-376.

LaMarche et al., Oct. 2012, Anti-hepatitis C virus activity and toxicity of type III phosphatidylinositol-4-kinase beta inhibitors, Antimicrobial Agents and Chemotherapy, 56(10): 5149-5156.

Lianzhi et al., "Synthesis of Acyclonucleoside Derivatives and Analogues of 5-Fluorouracil," Nanjing Yaoxueyuan Xuebao (19896) vol. 17, No. 3, pp. 161-166.

Lohman et al., "Inactivation of lactobacillus leichmannii ribonucleotide reductase by 2',2'-difluoro-2'-deoxycitifdine 5'-triphosphate: Covalent Modification," Biochem (2010) 49(7):1404-1417.

Mackman et al., "Discovery of GS-9131: Design, synthesis and optimization of amidate prodrugs of the novel nucleoside phosphonate HIV reverse transcriptase (RT) inhibitor GS-9148," Bioorganic & Medicinal Chemistry (2010) 18:3606-3617.

Muller et al., Antiviral Strategies, 24 pp., 4 (H.-G. Krausslich et al., eds., 2009).

Pubchem SCHEMBLCN285547, CID: 53839260, Create Date: Dec. 4, 2011, 11 pages.

Quintiliani et al, "Design, synthesis and biological evaluation of 2'-deoxy-2',2'-diflouro-5-halouridine phosphoramidate protides," Bioorganic & Medicinal Chemistry (2011) 19(14):4338-4345.

Rautio et al., "Prodrugs: design and clinical applications," Nature Reviews Drug Discovery (2008) 7:255-270.

Saiki et al. "DCK is frequently inactivated in acquired gemcitabine-resistant human cancer cells," Biochim. Biophys. Res. Commun. (2012) 421, 98-104.

Slusarczyk et al., "Application of ProTide Technology to Gemcitabine: A Successful Approach to Overcome the Key Cancer Resistance

(56) References Cited

OTHER PUBLICATIONS

Mechanisms Leads to a New Agent (NUC-1031) in Clinical Development," J. Med. Chem. (2014) vol. 57, pp. 1531-1542.

Tanaka et al., "Chemical Synthesis of Deosyribonucleotide with a 5'-Phosphoryl Group on a Polystyrene Polymer Support by the Phosphotriester Method," Chem and Pharma Bulletin (1987) 35:2726-2733.

Thornton et al., "Nucleoside Phosphate and Phosphonate Prodrug Clinical Candidates," Journal of Medicinal Chemistry (2016) 59:10400-10410.

Wilson et al., "Precursor synthesis towards the development of [1241]-labelled 2',2'-difluoro-2'deoxycytidine as a potential pet radiotracer for the anticancer drig gemicitabine," J Labelled Compounds and Radiopharmaceuticals (2001) 44(S1):S976-978.

Wu et al, "Synthesis and Biological Activity of a Gemcitabine Phosphoramidate Prodrug," J. Med Chem (2007) 50(15):3743-3746.

Zhao et al, "Synthesis and Biological Evaluation of Oral Prodrugs Based on the Structure of Gemcitabine," Chem Bio & Drug Des (2012) 80(3):479-488.

Zhuk, R., "Strucutre-Activity Relationship in Ftorafur (Tegafur) and Related 5-FU Prodrugs," Advances in Experimental and Biology (Purine and Pyrimidine Metabolism in Man IW) (1998) pp. 677-680.

International Search Report and Written Opinion dated Apr. 12, 2019 in PCT/US2019/014080.

Package insert for Fluorouracil injection, for intravenous use, Spectrum Pharmaceuticals, Inc., Revised Jul. 2016.

\* cited by examiner

5-FLUOROURACIL COMPOUNDS

CROSS REFERENCE TO RELATED APPLICATIONS

This application is a continuation-in-part of International Application No. PCT/US2019/014080, filed on Jan. 17, 2019 and published as WO 2019/143860, which claims the benefit of U.S. Provisional Application No. 62/619,557 filed Jan. 19, 2018 entitled "5-FLUOROURACIL COMPOUNDS", which is incorporated by reference in its entirety. This application also claims priority to U.S. Provisional Application No. 62/875,190 filed on Jul. 17, 2019 entitled "CYCLIC DEOXYRIBONUCLEOTIDE COMPOUNDS", which is incorporated by reference in its entirety.

FIELD

The present disclosure relates to the field of chemistry and medicine. More specifically, the present disclosure relates to 5-fluorouracil derived compounds, including acetal and hemiaminal ether compounds, their preparation and their uses. In some embodiments, such compounds are useful to selectively deliver certain pharmaceutical agents to the liver.

BACKGROUND

The following description of the background is provided to aid in understanding the invention, but is not admitted to be, or to describe, prior art to the invention.

5-Fluorouracil is a synthetic analog of uracil that is one of the four nucleobases in RNA and has been used as a therapeutic agent to treat various forms of cancer. It is one of the Essential Medicines in WHO's list for its efficacy and safety, and available in intravenous injection and topical forms. The mechanism of action of 5-fluorouracil is mainly as a thymidylate synthase inhibitor that blocks synthesis of the pyrimidine thymidine to cause a cell starvation of thymidine leading to cell death. The active form of 5-fluorouracil as a thymidylate synthase inhibitor is fluorodeoxyuridine monophosphate (FdUMP) generated mainly in the liver.

5-Fluorouracil has very short biological half-life (16 minutes), very narrow therapeutic index, and varies side effects that can be very serious. Development of new 5-fluorouracil analog compounds for better efficacy and safety has been going for many years and several compounds have made to the market. Floxuridine, also as 5-fluorodeoxyuridine, has been used to treat colorectal cancer via a continuous hepatic artery infusion. Doxifluridine has been used in certain countries as a cytostatic agent in chemotherapy. Capecitabine has been used orally to treat breast, gastric, and colorectal cancers. Despite the progress in the field, there is a need for new compounds to further improve the drug delivery efficiency or address a new application based on new technologies. For example, liver-targeting compounds which can reach the liver more efficiently and are not active outside the liver reducing pharmacological or toxicological effects of an agent outside the target tissue. Thus, new compounds with liver-targeting profile may significantly improve the therapeutic index of 5-fluorouracil mechanism based therapies.

SUMMARY

Novel 5-fluorouracil derived acetal and hemiaminal ether compounds, their preparation and their uses are described.

Some embodiments are related to novel 5-fluorouracil derived acetal and hemiaminal ether compounds that are delivered orally to the liver where the compounds provide a therapeutic benefit. Another aspect includes the use of the 5-fluorouracil derived acetal and hemiaminal ether compounds to treat diseases that benefit from enhanced drug distribution to the liver and like tissues and cells, including but not limited to hepatocellular carcinoma (HCC), kidney cancer, colorectal cancer, breast cancer, stomach cancer, gastric cancer, esophageal cancer, pancreatic cancer, and cervical cancer. In another aspect, the 5-fluorouracil derived acetal and hemiaminal ether compounds are used to increase the pharmacological or clinical activity of certain classes of pharmaceutical compounds such as 5-fluorouracil derived analog compounds. In another aspect, the 5-fluorouracil derived acetal and hemiaminal ether compounds are used to reduce potential side effects of certain classes of pharmaceutical compounds such as 5-fluorouracil derived analog compounds, especially the side effects occurring outside the liver. In some embodiments, the 5-fluorouracil derived acetal and hemiaminal ether compounds are useful in the more efficient oral delivery of the 5-fluorouracil derived analog compounds to the liver. Some additional embodiments relate to a method of making the 5-fluorouracil derived acetal and hemiaminal ether compounds.

Some embodiments provided herein include a compound of Formula I:

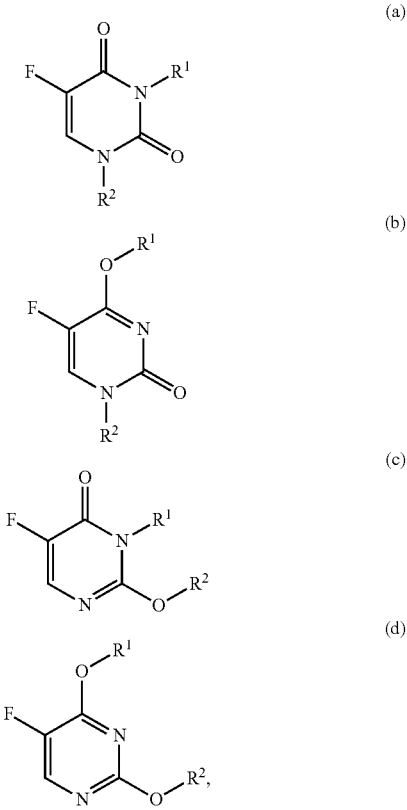

or a stereoisomer or a pharmaceutically acceptable salt thereof, wherein $R^1$ and $R^2$ have any of the values described herein.

Some embodiments relate to a compound of Formula II, III, IV, V, and VI:
(II)
(a)
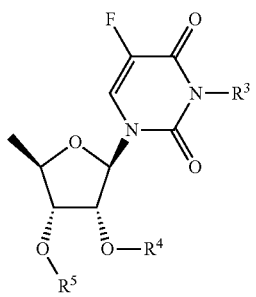
(b)
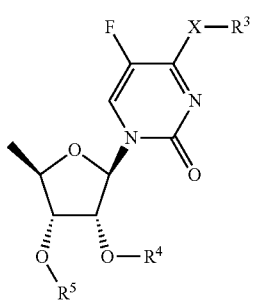
(c)
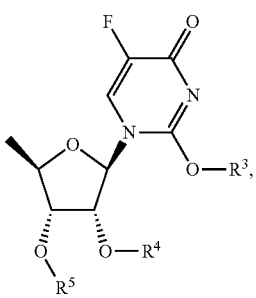
or a stereoisomer or a pharmaceutically acceptable salt thereof,
(III)
(a)
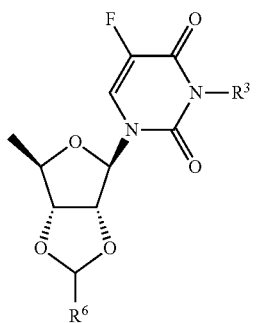
(b)
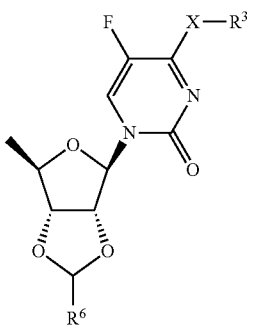
(c)
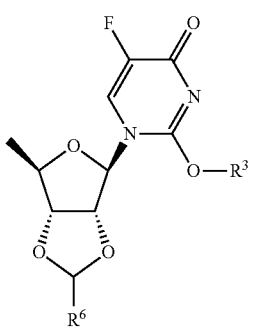
or a stereoisomer or a pharmaceutically acceptable salt thereof,
(IV)
(a)
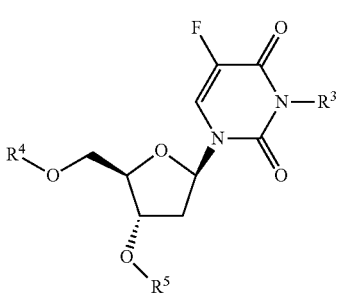
(b)
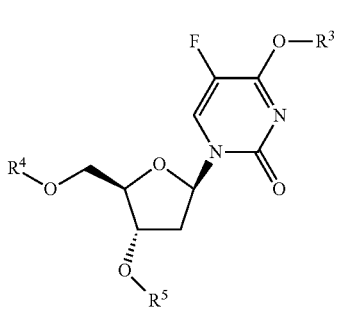

(V)

(c)
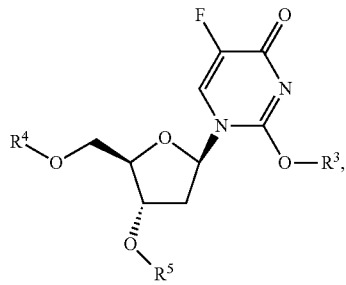

or a stereoisomer or a pharmaceutically acceptable salt thereof, (V)

(a)
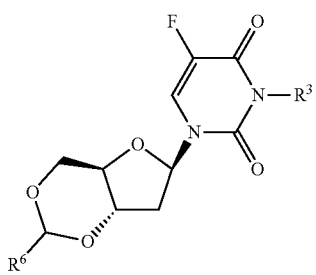

(b)
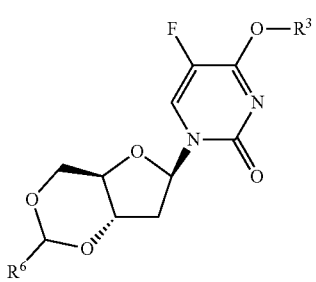

(c)
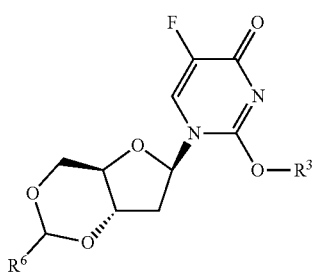

or a stereoisomer or a pharmaceutically acceptable salt thereof, (VI)

(a)
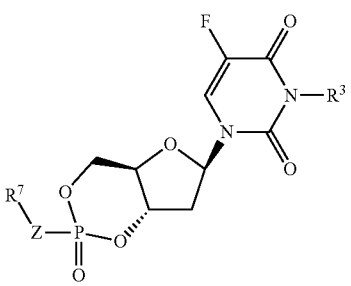

(b)
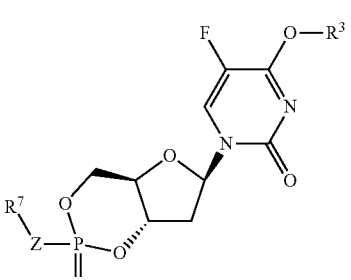

(c)
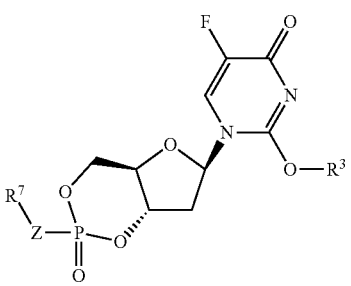

or a stereoisomer or a pharmaceutically acceptable salt thereof, wherein $R^3$, $R^4$, $R^5$, $R^6$, $R^7$, X, Y, and Z have any of the values described herein.

Some embodiments relate to a pharmaceutical composition comprising any of the above compounds and a pharmaceutically acceptable excipient.

Some embodiments relate to a pharmaceutical composition further comprising one or more anti-cancer agents.

Some embodiments relate to a method of treating a disease, disorder or condition comprising administering an effective amount of any of the above compounds.

In some embodiments, the disease, disorder or condition is a disease, disorder or condition of the liver.

In some embodiments, the disease, disorder or condition is a disease in which the liver is involved in the production and/or the homeostasis control of the biochemical end products of the disease, disorder or condition.

In some embodiments, the disease, disorder or condition is a metabolic, cardiovascular or hormonal disease in which the liver is involved in the production and/or the homeostasis control of the biochemical end products of the disease, disorder or condition.

In some embodiments, the disease, disorder or condition is selected from the group consisting of hepatocellular carcinoma, kidney cancer, colorectal cancer, breast cancer, stomach cancer, gastric cancer, esophageal cancer, pancreatic cancer, and cervical cancer.

In some embodiments, the disease, disorder or condition is a non-liver disease, disorder or condition.

In some embodiments, the non-liver disease, disorder or condition is various types of cancers, or other disease in which the 5-fluorouracil derived acetal and hemiaminal ether compounds enhances the distribution of an active drug to the target tissue or cell.

Some embodiments relate to a method of treating a liver disease comprising administering an effective amount of a compound of any of the above compounds to a subject in need thereof.

Some embodiments further comprise administering an effective amount of at least one additional therapeutic agent to the subject in need thereof.

In some embodiments, the subject is a mammal.
In some embodiments, the subject is human.
Some embodiments relate to a method of inhibiting viral replication in a cell comprising contacting the cell with any of the above compounds.

Some embodiments relate to a method of intervening in a molecular pathway or modulating a target in a cell comprising contacting the cell with any of the above compounds.

In some embodiments, the cell is in vivo.
In some embodiments, the cell is ex vivo.
In some embodiments, the cell is a hepatocyte.
In some embodiments, the cell is a cancerous cell.
In some embodiments, the cell is mammalian.
In some embodiments, the cell is human.
Some embodiments of the compounds, compositions, and methods provided herein include a pharmaceutical composition comprising any of the compounds provided herein and a pharmaceutically acceptable excipient.

Some embodiments of the compounds, compositions, and methods provided herein include a method of treating a disease or condition in the liver in a subject comprising administering an effective amount of any of the compounds provided herein to a subject in need thereof.

Some embodiments also include administering an effective amount of one or more additional therapeutic agents to the subject in need thereof.

In some embodiments, the subject is a mammal.
In some embodiments, the subject is a human.
Some embodiments of the compounds, compositions, and methods provided herein include the use of any one of the compounds provided herein for treating a disease in the liver or a disease or condition in which the physiological or pathogenic pathways involve the liver in a subject.

Some embodiments also include the use of any one of the compounds provided herein in combination with an additional therapeutic agent.

Some embodiments of the compounds, compositions, and methods provided herein include any one of the compositions provided herein for use in the preparation of a medicament for treating a disease or condition in the liver or a disease or condition in which the physiological or pathogenic pathways involve the liver.

DETAILED DESCRIPTION

The present embodiments are directed to compositions and methods related to novel 5-fluorouracil derived acetal and hemiaminal ether compounds, their preparation and their uses. In some embodiments, the novel 5-fluorouracil derived acetal and hemiaminal ether compounds facilitate delivery into cells of 5-fluorouracil derived therapeutic agents, such as 5-fluorouracil, doxifluridine, 5-fluorouridine monophosphonate and/or 5-fluorodeoxyuridine monophosphonate.

These 5-fluorouracil derived acetal and hemiaminal ether compounds and their stereoisomers and pharmaceutically acceptable salts are represented by Formula I, II, III, IV, V, and VI:

(I)

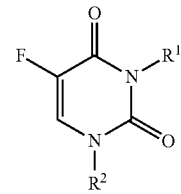

(a)

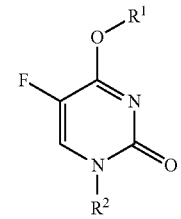

(b)

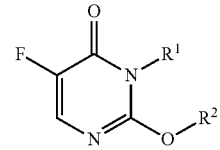

(c)

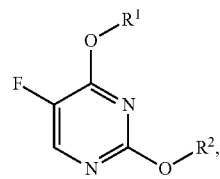

(d)

or a stereoisomer or a pharmaceutically acceptable salt thereof, (II)

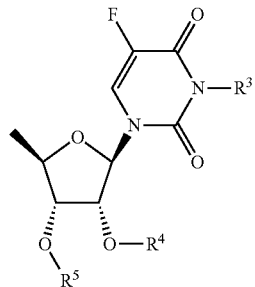

(a)

(b)
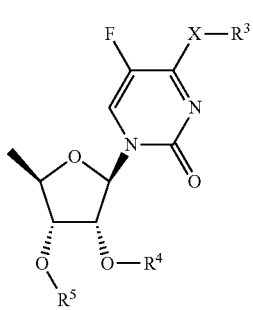
(c)
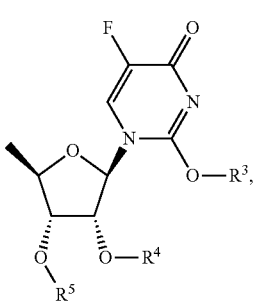
or a stereoisomer or a pharmaceutically acceptable salt thereof,
(III)
(a)
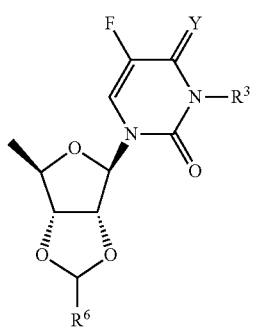
(b)
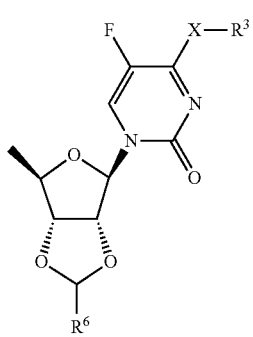
(c)
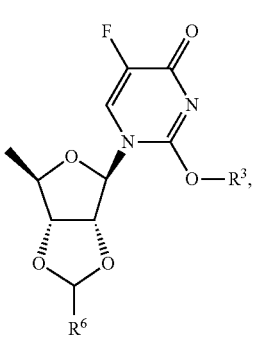
or a stereoisomer or a pharmaceutically acceptable salt thereof,
(IV)
(a)
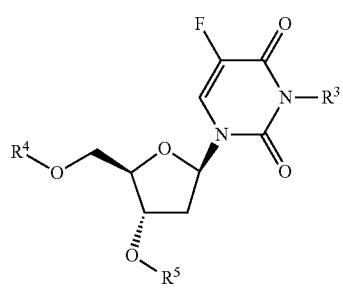
(b)
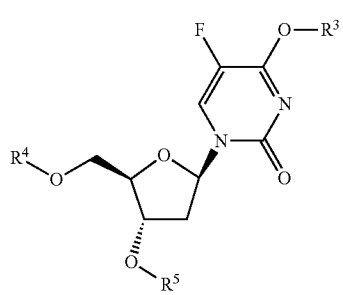
(c)
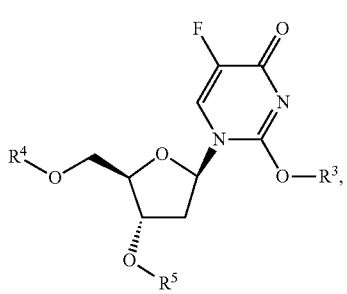
or a stereoisomer or a pharmaceutically acceptable salt thereof, (V)

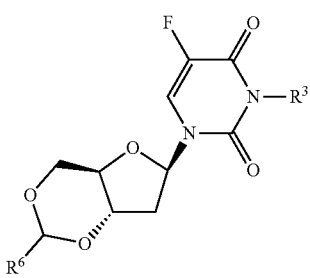
(a)

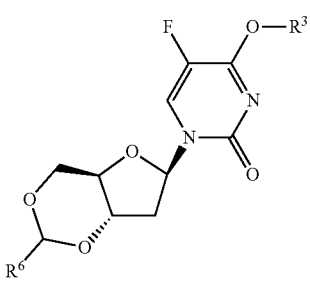
(b)

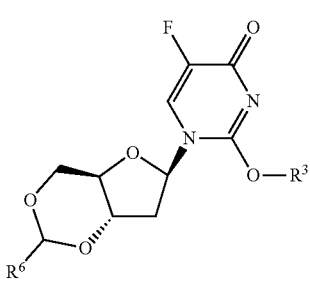
(c)

or a stereoisomer or a pharmaceutically acceptable salt thereof, (VI)

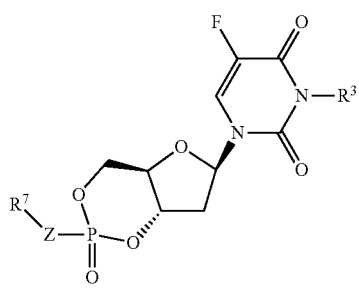
(a)

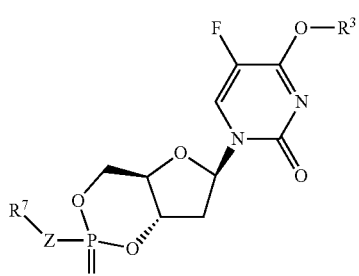
(b)

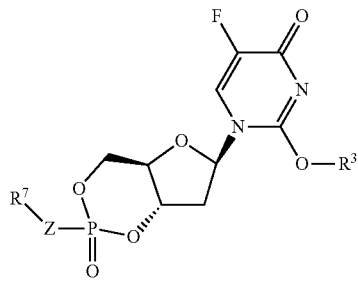
(c)

or a stereoisomer or a pharmaceutically acceptable salt thereof, wherein $R^1$, $R^2$, $R^3$, $R^4$, $R^5$, $R^6$, $R^7$, X, Y, and Z have any of the values described herein.

In some embodiments, $R^1$ and $R^2$ are independently selected from the group consisting of H, an optionally substituted $C_1$-$C_{10}$ alkyl-$OCH_2$—, an optionally substituted ($C_{6-10}$ aryl)-$CH_2$—$OCH_2$—, and an optionally substituted (5-10 membered heteroaryl)-$CH_2$—$OCH_2$—, an optionally substituted ($C_{6-10}$ aryl)-$OCH_2$—, and an optionally substituted (5-10 membered heteroaryl)-$OCH_2$—; provided that at least one of $R^1$ and $R^2$ is not H.

In some embodiments, $R^3$ is selected from the group consisting of H, an optionally substituted $C_1$-$C_{10}$ alkyl-$OCH_2$—, an optionally substituted $C_1$-$C_{10}$ alkyl-$NHCH_2$—, an optionally substituted $C_1$-$C_{10}$ acyl, an optionally substituted $C_1$-$C_{10}$ alkyl-$OC(O)$—, an optionally substituted ($C_{6-10}$ aryl)-$CH_2OCH_2$—, an optionally substituted ($C_{6-10}$ aryl)-$OCH_2$—, an optionally substituted ($C_{6-10}$ aryl)-$C(O)$—, an optionally substituted (5-10 membered heteroaryl)-$CH_2OCH_2$—, an optionally substituted (5-10 membered heteroaryl)-$OCH_2$—, an optionally substituted ($C_{6-10}$ aryl)-$OC(O)$—, an optionally substituted (5-10 membered heteroaryl)-$C(O)$—, and an optionally substituted (5-10 membered heteroaryl)-$OC(O)$—.

In some embodiments, $R^4$ and $R^5$ are independently selected from the group consisting of H, an optionally substituted $C_1$-$C_{10}$ alkyl-$OCH_2$—, an optionally substituted $C_1$-$C_{10}$ acyl, an optionally substituted ($C_{6-10}$ aryl)-$CH_2OCH_2$—, an optionally substituted ($C_{6-10}$ aryl)-$OCH_2$—, an optionally substituted ($C_{6-10}$ aryl)-$C(O)$—, an optionally substituted (5-10 membered heteroaryl)-$CH_2OCH_2$—, an optionally substituted (5-10 membered heteroaryl)-$OCH_2$—, an optionally substituted (5-10 membered heteroaryl)-$C(O)$—, an optionally substituted $C_1$-$C_{10}$ alkyl-$NR^{7A}CH_2$—, an optionally substituted ($C_{6-10}$ aryl)-$NR^{7A}CH_2$—, an optionally substituted (5-10 membered heteroaryl)-$NR^{7A}CH_2$—, $N(R^{7A})_2CH_2$—, and -L-$CH_2$—; $R^{7A}$ is independently selected from the group consisting of H, an optionally substituted $C_{1-10}$ alkyl, an optionally substituted $C_{1-10}$ acyl, an optionally substituted $C_{6-10}$ aryl, and an optionally substituted 5-10 membered heteroaryl; X is O or $NR^{1A}$; Y is O or $NR^{1B}$; $R^{1A}$ is selected from the group consisting of H, an optionally substituted $C_1$-$C_{10}$ alkyl-$OCH_2$—, an optionally substituted ($C_{6-10}$ aryl)-$OCH_2$—, and an optionally substituted (5-10 membered heteroaryl)-$OCH_2$—; $R^{1B}$ is selected from the group consisting of an optionally substituted $C_1$-$C_{10}$ alkyl-$OCH_2$—, an optionally substituted $C_1$-$C_{10}$ acyl, an optionally substituted $C_1$-$C_{10}$ alkyl-$OC(O)$—, an optionally substituted ($C_{6-10}$ aryl)-$OCH_2$—, an optionally substituted ($C_{6-10}$ aryl)-$C(O)$—, an optionally substituted (5-10 membered heteroaryl)-$OCH_2$—, an optionally substituted ($C_{6-10}$ aryl)-$OC(O)$—, an optionally substituted (5-10 membered heteroaryl)-C(O)—, and an optionally substituted (5-10 membered heteroaryl)-OC(O)—; and L is an optionally substituted 4-10 membered nitrogen-containing heterocycle, provided that at least one of $R^4$ and $R^5$ is not H when $R^3$ is H or —X—$R^3$ is —NHC(O)O-alkyl.

In some embodiments, $R^6$ is H or $R^{6A}$; $R^{6A}$ is a $C_1$-$C_{10}$ alkyl, an $C_{6-10}$ aryl, a 5-10 membered heteroaryl or a 4-10 membered heterocyclyl, each optionally substituted with 1 to 4 $R^{6AA}$; each $R^{6AA}$ is independently selected from the group consisting of halo, OH, an optionally substituted $C_1$-$C_{10}$ alkyl-OCH$_2$O—, an optionally substituted $C_1$-$C_{10}$ alkylC(O)O—, an optionally substituted $C_1$-$C_{10}$ alkyl-OC(O)O—, optionally substituted $C_1$-$C_{10}$ alkyl, optionally substituted $C_1$-$C_{10}$ alkoxy, optionally substituted $C_3$-$C_{10}$ cycloalkyl, optionally substituted $C_{6-10}$ aryl, optionally substituted 5-10 membered heteroaryl, optionally substituted 4-10 membered heterocyclyl an optionally substituted ($C_{6-10}$ aryl)-OCH$_2$—, and an optionally substituted (5-10 membered heteroaryl)-OCH$_2$—.

In some embodiments, $R^7$ is selected from the group consisting of an optionally substituted $C_1$-$C_{20}$ alkyl, an optionally substituted $C_3$-$C_{20}$ cycloalkyl, an optionally substituted $C_2$-$C_{20}$ alkenyl, an optionally substituted $C_{6-10}$ aryl, an optionally substituted 5-10 membered heteroaryl, an optionally substituted $C_1$-$C_{10}$ alkyl-OCH$_2$—, an optionally substituted $C_1$-$C_{10}$ alkyl-CO—OCH$_2$—, an optionally substituted ($C_{6-10}$ aryl)-OCH$_2$—, an optionally substituted (5-10 membered heteroaryl)-OCH$_2$—; an optionally substituted ($C_{6-10}$ aryl)-CH$_2$—, an optionally substituted (5-10 membered heteroaryl)-CH$_2$—, an optionally substituted ($C_3$-$C_{10}$ cycloalkenyl)-CH$_2$,

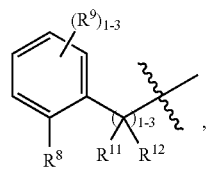

and

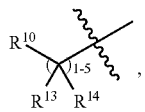

In some embodiments, $R^8$ is selected from the group consisting of halo, —O—$C_{1-6}$ alkyl, $C_1$-$C_{10}$ alkyl, —OCH$_2$OR$^{15}$, —CH(OR$^{15}$)$_2$, —C-amido, —CH$_2$CH$_2$OR$^{15}$,

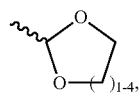

and —CH$_2$O-carboxy.

In some embodiments, each $R^9$ is independently selected from the group consisting of H, halo, and $C_1$-$C_{10}$ alkyl.

In some embodiments, $R^{10}$ is selected from the group consisting of —O-carboxy, —OCH$_2$OR$^{15}$, —CH(OR$^{15}$)$_2$, —C-carboxy, —C-amido, —CH$_2$OCH$_2$OR$^{15}$,

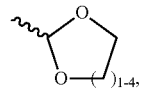

—CH$_2$O-carboxy, $C_1$-$C_{10}$ alkyl, and $C_3$-$C_{10}$ cycloalkyl.

In some embodiments, each $R^{11}$ and $R^{12}$ are independently H or $C_1$-$C_{10}$ alkyl; or alternatively, an $R^{11}$ and $R^{12}$ attached to the same carbon atom may be taken together with the atom to which they are attached form a $C_3$-$C_{10}$ cycloalkyl.

In some embodiments, each $R^{13}$ and $R^{14}$ are independently H or $C_1$-$C_{10}$ alkyl; or alternatively, an $R^{13}$ and $R^{14}$ attached to the same carbon atom may be taken together with the atom to which they are attached form a $C_3$-$C_{10}$ cycloalkyl.

In some embodiments, $R^{15}$ is an optionally substituted $C_1$-$C_{10}$ alkyl.

In some embodiments, X is O or NR$^{1A}$; and R$^{1A}$ is selected from the group consisting of H, an optionally substituted $C_1$-$C_{10}$ alkyl-OCH$_2$—, an optionally substituted ($C_{6-10}$ aryl)-OCH$_2$—, and an optionally substituted (5-10 membered heteroaryl)-OCH$_2$—.

In some embodiments, Y is O or NR$^{1B}$; and R$^{1B}$ is selected from the group consisting of an optionally substituted $C_1$-$C_{10}$ alkyl-OCH$_2$—, an optionally substituted $C_1$-$C_{10}$ acyl, an optionally substituted $C_1$-$C_{10}$ alkyl-OC(O)—, an optionally substituted ($C_{6-10}$ aryl)-OCH$_2$—, an optionally substituted ($C_{6-10}$ aryl)-C(O)—, an optionally substituted (5-10 membered heteroaryl)-OCH$_2$—, an optionally substituted ($C_{6-10}$ aryl)-OC(O)—, an optionally substituted (5-10 membered) heteroaryl-C(O)—, and an optionally substituted (5-10 membered heteroaryl)-OC(O)—.

In some embodiments, Z is O or NR$^{1C}$; and R$^{1C}$ is selected from the group consisting of H, an optionally substituted $C_1$-$C_{10}$ alkyl, and an optionally substituted aryl.

In some embodiments, $R^3$ is H.

In some embodiments, Z is O.

In some embodiments, $R^7$ is selected from the group consisting of an optionally substituted $C_1$-$C_{20}$ alkyl, an optionally substituted $C_2$-$C_{20}$ alkenyl, an optionally substituted $C_3$-$C_{20}$ cycloalkyl, an optionally substituted $C_{6-10}$ aryl, an optionally substituted 5-10 membered heteroaryl, an optionally substituted $C_1$-$C_{10}$ alkyl-OCH$_2$—, an optionally substituted $C_1$-$C_{10}$ alkyl-CO—OCH$_2$—, an optionally substituted ($C_{6-10}$ aryl)-OCH$_2$—, an optionally substituted (5-10 membered heteroaryl)-OCH$_2$—; an optionally substituted ($C_{6-10}$ aryl)-CH$_2$—, and an optionally substituted (5-10 membered heteroaryl)-CH$_2$—. In some embodiments, $R^7$ is an optionally substituted $C_1$-$C_{20}$ alkyl. In some embodiments, $R^7$ is an optionally substituted $C_{6-10}$ aryl. In some embodiments, $R^7$ is an optionally substituted ($C_{6-10}$ aryl)-CH$_2$—.

Some embodiments have the structure:

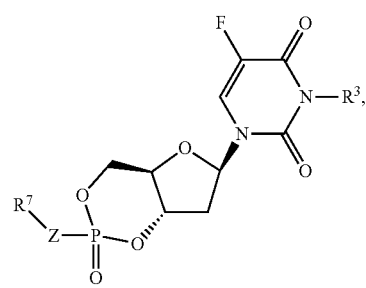

or a stereoisomer or a pharmaceutically acceptable salt thereof.

In some embodiments, $R^7$ is

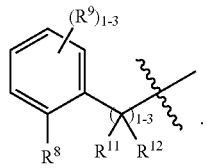

In some embodiments, $R_8$ is selected from the group consisting of H, F, $C_1$-$C_{10}$ alkyl, —OMe, —OEt, —OCH$_2$R$^{15}$, —CH(OR$^{15}$)$_2$, —C-amido, —CH$_2$OCH$_2$OR$^{15}$,

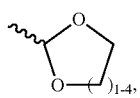

and —CH$_2$O-carboxy; and

In some embodiments, $R^9$ is selected from the group consisting of H, F, and $C_1$-$C_{10}$ alkyl.

In some embodiments, $R^8$ is H and $R^9$ is H or F.

In some embodiments, $R^8$ is selected from the group consisting of —OMe, —OEt, —OCH$_2$OR$^{15}$, —CH(OR$^{15}$)$_2$, —C-amido, —CH$_2$CH$_2$OR$^{15}$,

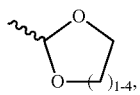

and —CH$_2$O-carboxy.

In some embodiments, $R^8$ is F.
In some embodiments, $R^9$ is H.
In some embodiments, $R^9$ is F.
In some embodiments, $R^7$ is

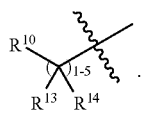

In some embodiments, $R^{10}$ is selected from the group consisting of —O-carboxy, —OCH$_2$OR$^{15}$, —CH(OR$^{15}$)$_2$, —C-carboxy, —C-amido, —CH$_2$CH$_2$OR$^{15}$,

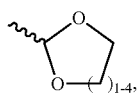

and —CH$_2$O-carboxy.

In some embodiments, $R^{10}$ is a $C_1$-$C_{10}$ alkyl or a $C_3$-$C_{10}$ cycloalkyl.

Some embodiments include a compound selected from the group consisting of:

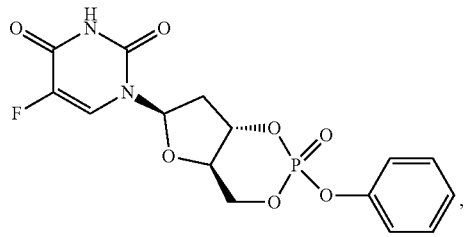

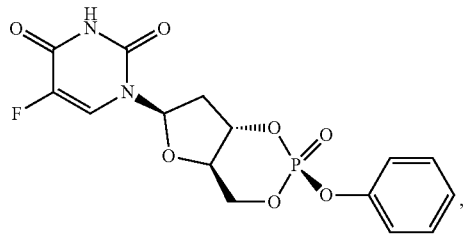

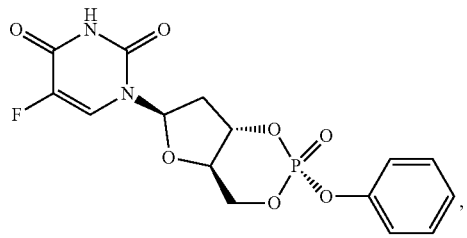

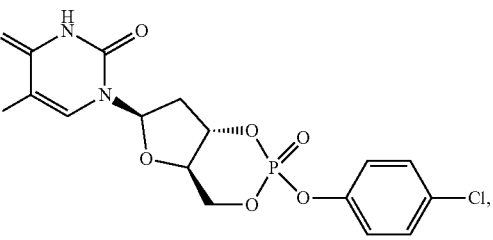

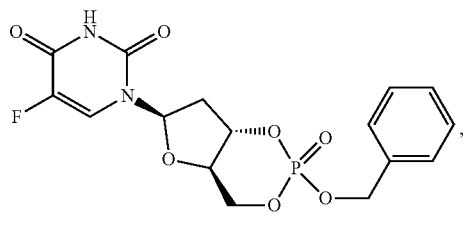

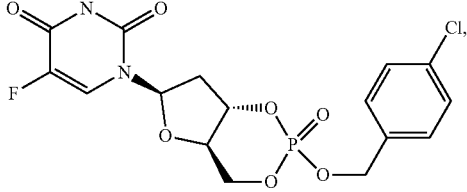

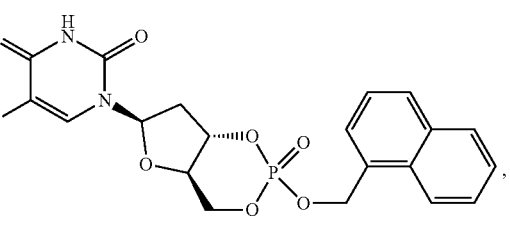

-continued
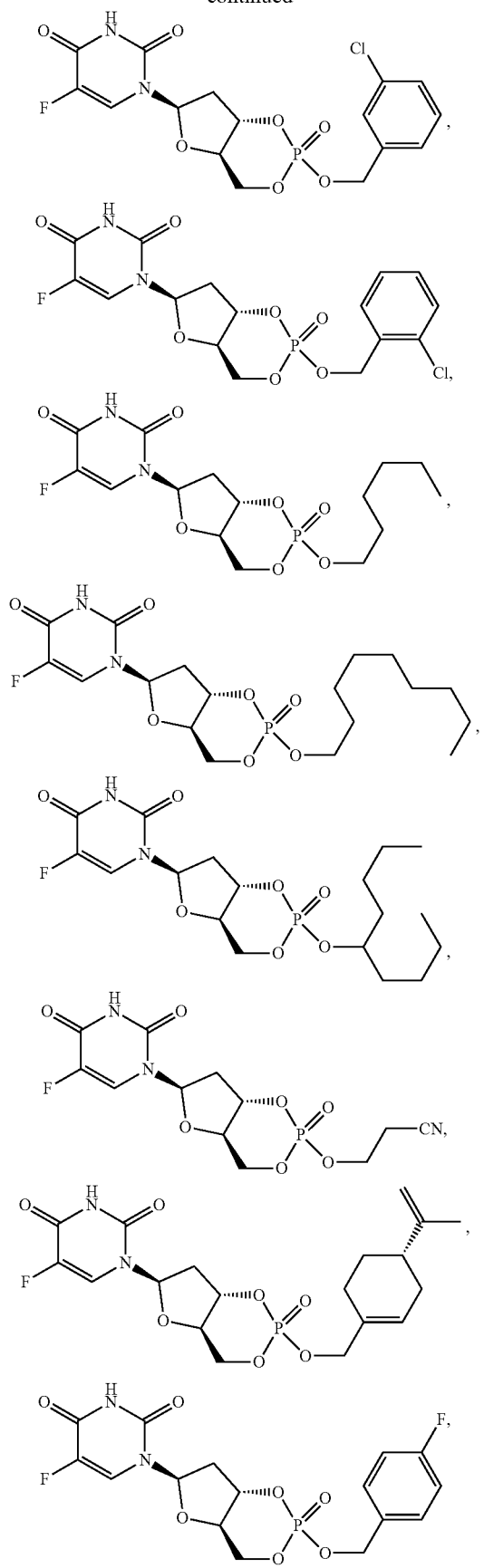
-continued
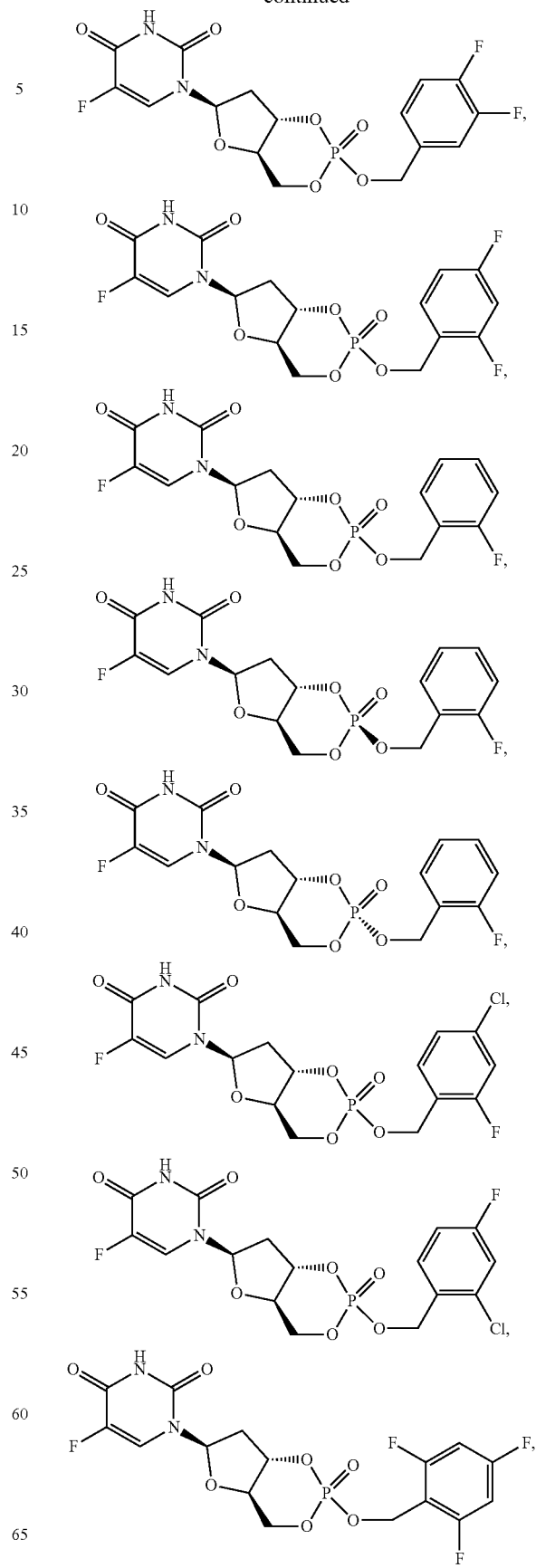

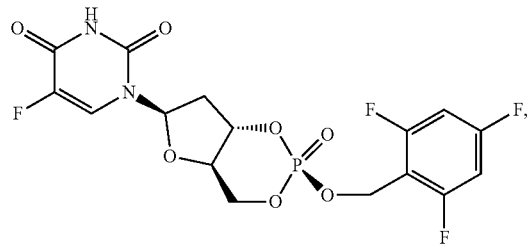
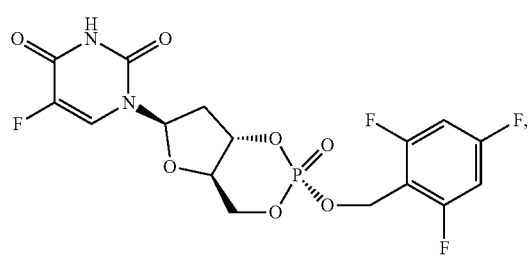
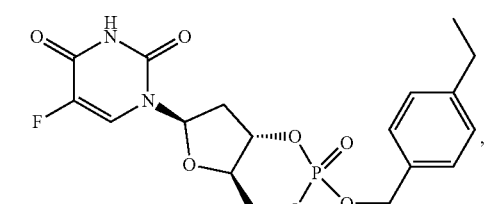
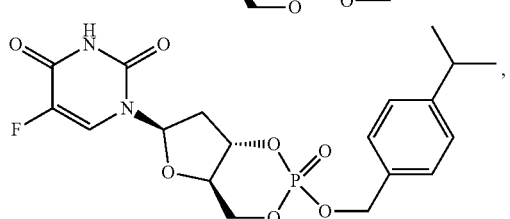
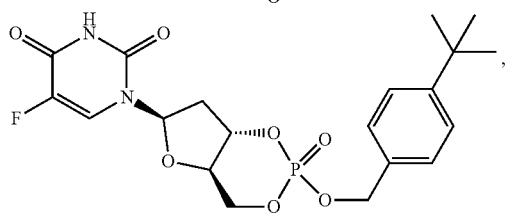
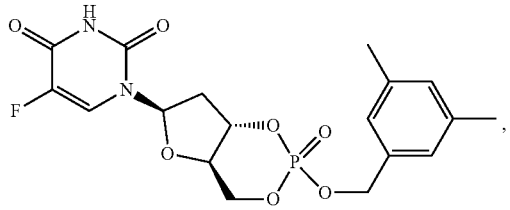
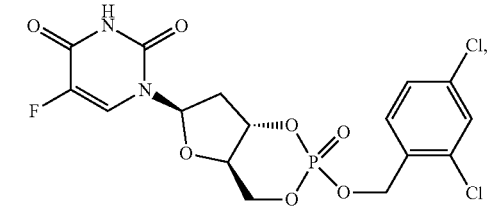
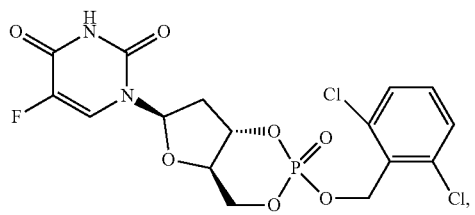
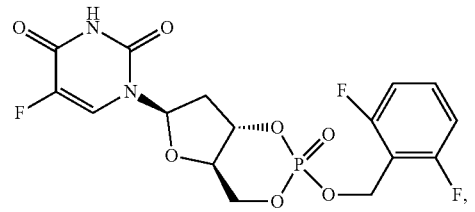
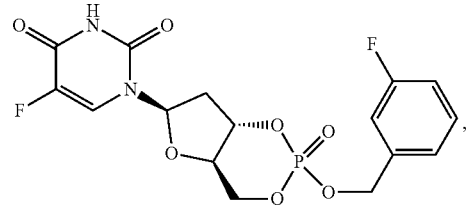
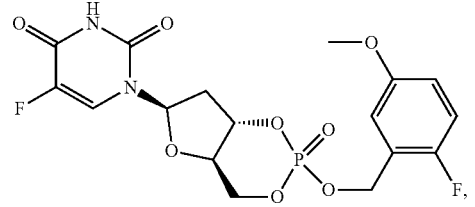
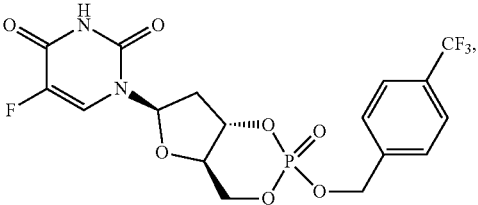
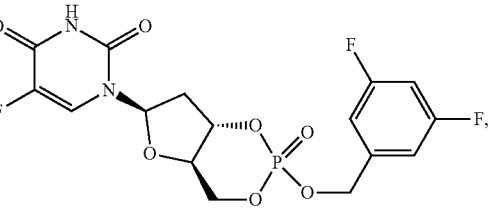
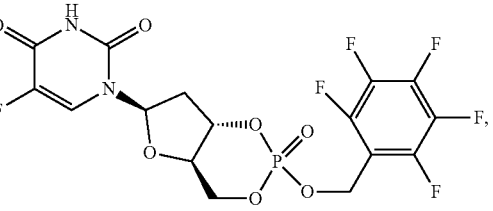
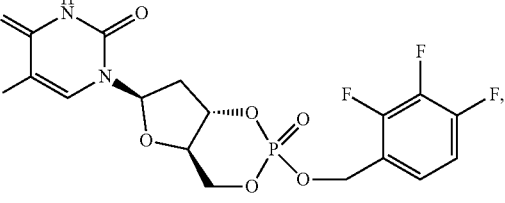

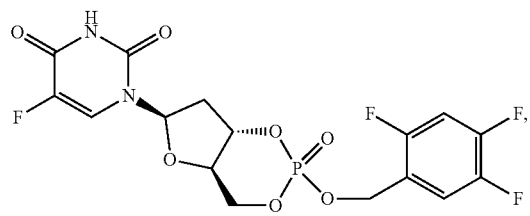
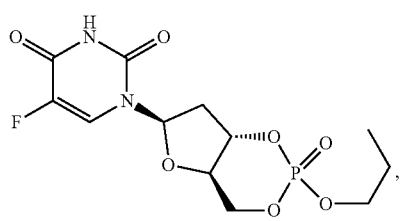
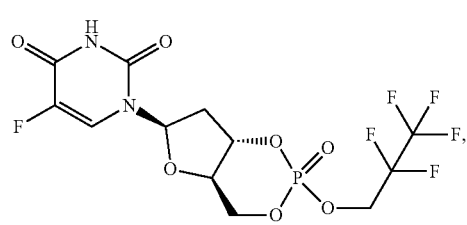
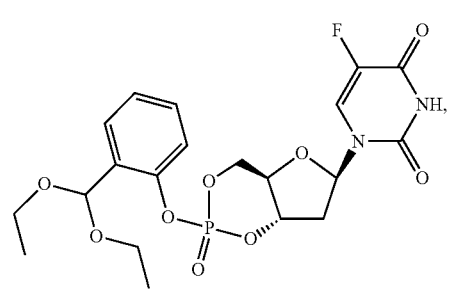
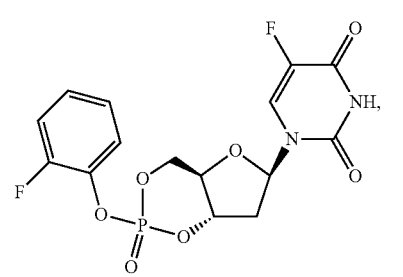
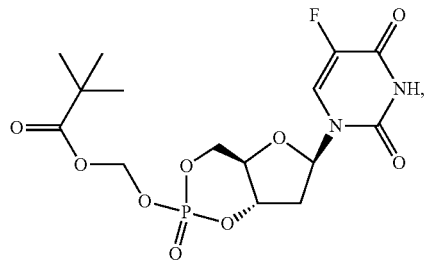
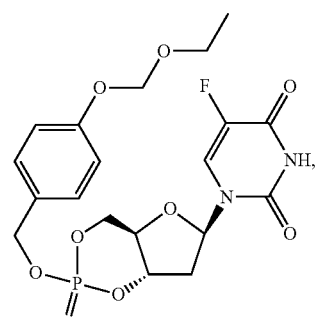
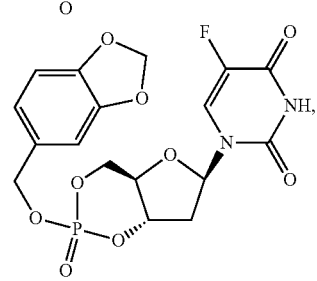
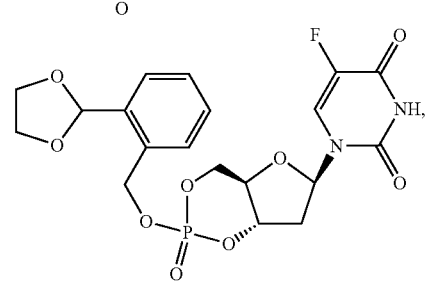
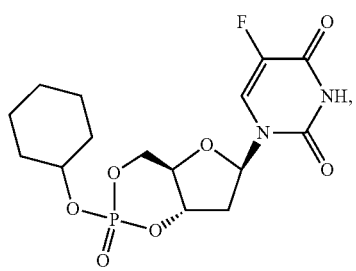
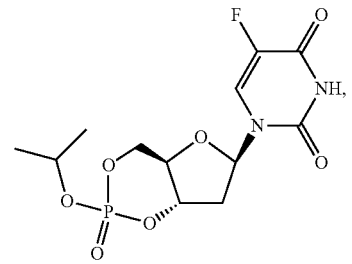
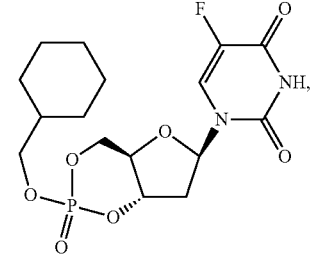

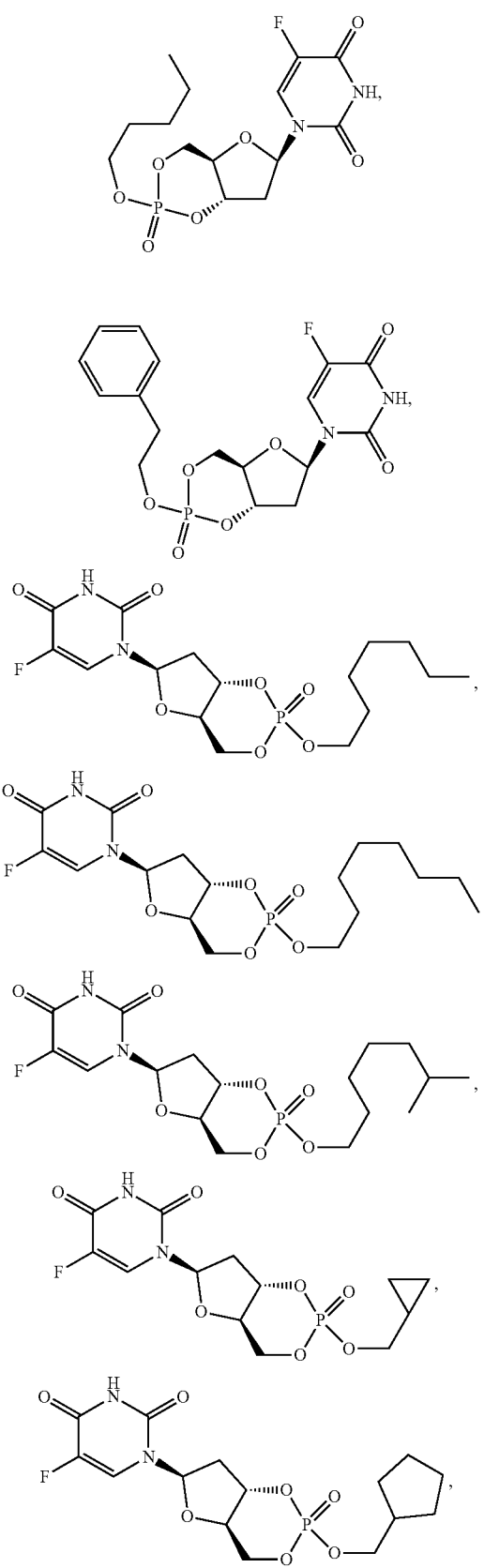
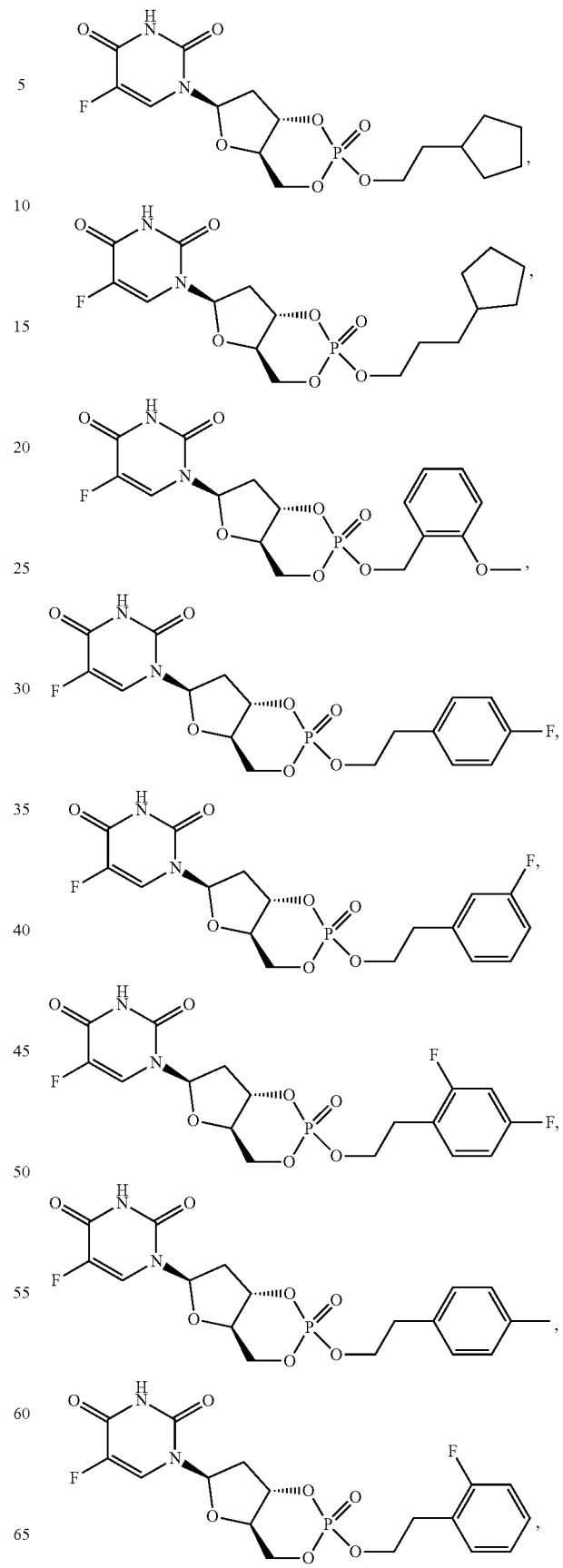

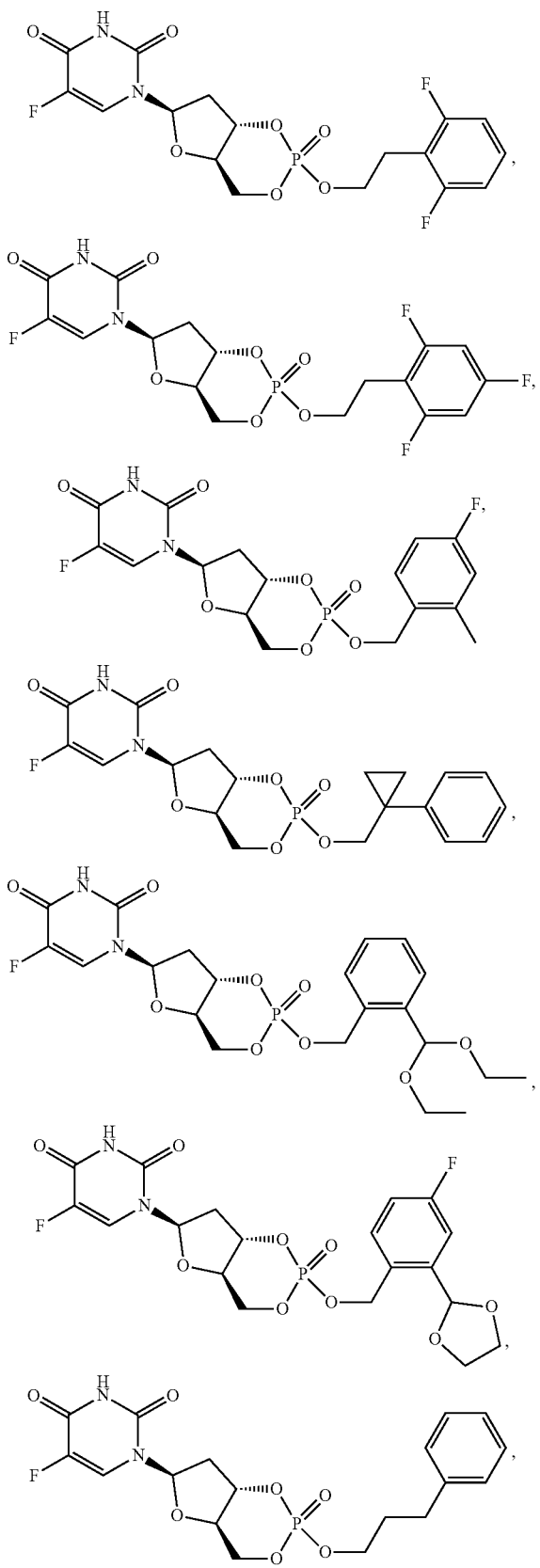

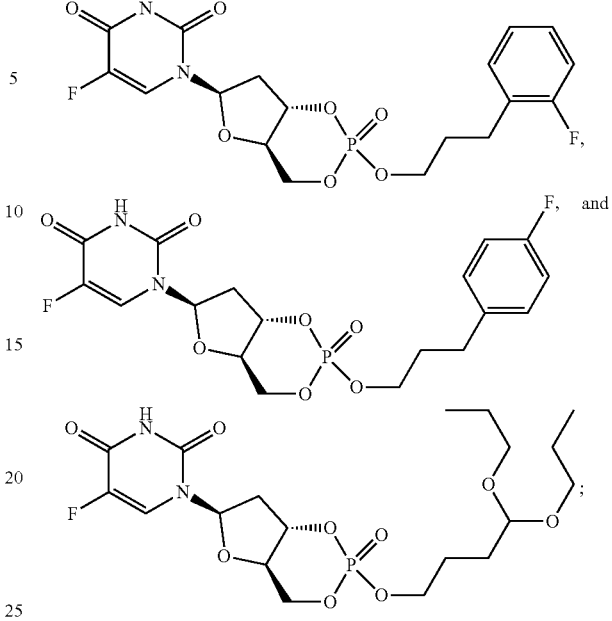

or a stereoisomer or pharmaceutically acceptable salt thereof.

In some embodiments, the 5-fluorouracil derived acetal and hemiaminal ether compounds of Formula I, II, III, IV, V, and VI are substrates of liver enzymes such as cytochrome p450 isozymes CYP3As (a family of monooxygenase), dehydrogenases, esterases, and amidases.

CYP3A4 is expressed in the liver in a level much higher than other tissues (DeWaziers et al. J Pharm Exp Ther 253:387 (1990)). 5-Fluorouracil derived acetal and hemiaminal ether compounds of Formula I, II, III, IV, V, and VI are predominantly activated via CYP3A4 in the liver. In some embodiments, the compounds of Formula I, II, III, IV, V, and VI have high efficiency in liver-targeting via selective delivery of biologically active agents to the liver. In some embodiments, the acetal and hemiaminal compounds are used to increase the therapeutic index of a drug, since the compounds of Formula I, II, III, IV, V, and VI may not be active or may be less active outside the liver.

In some embodiments, due to the liver-targeting nature of the 5-fluorouracil derived acetal and hemiaminal ether compounds of Formula I, II, III, IV, V, and VI, the compounds are used to treat diseases that benefit from enhanced drug distribution to the liver and like tissues and cells, including but not limited to diseases in the liver, such as hepatocellular carcinoma.

In some embodiments, the disclosed compounds are used to improve pharmacokinetic properties such as prolonging half-life or enhancing absorption of a drug. In addition, the disclosed methodology can be used to achieve sustained delivery of an active therapeutic agent. Due to the pharmacokinetic property enhancement of the 5-fluorouracil derived acetal and hemiaminal ether compounds of Formula I, II, III, IV, V, and VI, the compounds are used to treat diseases that benefit from enhanced drug properties, including but not limited to diseases such as various types of cancer. In some embodiments, a method of making these compounds is described.

Certain compounds of Formula I, II, III, IV, V, and VI have asymmetric centers where the stereochemistry may be unspecified, and the diastereomeric mixtures of these compounds are included, as well as the individual stereoisomers when referring to a compound of Formula I, II, III, IV, V, and VI generally.

Some embodiments of the compounds, compositions and methods provided herein include a pharmaceutical composition comprising a compound provided herein and a pharmaceutically acceptable carrier.

Some embodiments also include administering an effective amount of a second or multiple therapeutic agents in combination with a compound provided herein to the subject in need thereof.

In some embodiments, the subject is mammalian.

In some embodiments, the subject is human.

Some embodiments of the compounds, compositions and methods provided herein include a method of testing a compound in a cell comprising contacting the cell with the disclosed compounds.

Some embodiments of the compounds, compositions and methods provided herein include use of a compound provided herein in the treatment of a disease in the liver.

Some embodiments include the use of a compound provided herein in combination with additional therapeutic agent(s) for the treatment of a disease in the liver.

Some embodiments of the compounds, compositions and methods provided herein include use of a compound provided herein in the treatment of a disease or condition by intervening in a molecular pathway in the liver.

Some embodiments include the use of a compound provided herein in combination with additional therapeutic agent(s) for the treatment of a disease or condition by intervening in a molecular pathway in the liver.

Some embodiments of the compounds, compositions and methods provided herein include use of a compound provided herein in the treatment of a non-liver disease such as various types of cancer.

Some embodiments include the use of a compound provided herein in combination with additional therapeutic agent(s) for the treatment of a non-liver disease such as various types of cancer.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

In accordance with the present disclosure and as used herein, the following terms are defined with the following meanings, unless explicitly stated otherwise. It is to be understood that both the foregoing general description and the following detailed description are exemplary and explanatory only and are not restrictive of the subject matter claimed. In this application, the use of the singular includes the plural unless specifically stated otherwise. In this application, the use of "or" means "and/or" unless stated otherwise. Furthermore, use of the term "including" as well as other forms, such as "includes," and "included" is not limiting.

As used herein, ranges and amounts can be expressed as "about" a particular value or range. "About" also includes the exact amount. Hence "about 10%" means "about 10%" and also "10%."

As used herein, "optional" or "optionally" means that the subsequently described event or circumstance does or does not occur, and that the description includes instances where the event or circumstance occurs and instances where it does not. For example, an optionally substituted group means that the group is unsubstituted or is substituted.

As used herein, the singular forms "a," "an" and "the" include plural referents unless the context clearly dictates otherwise. Thus, for example, reference to a composition comprising "a therapeutic agent" includes compositions with one or a plurality of therapeutic agents.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_2$-$C_6$ alkenyl, $C_2$-$C_6$ alkynyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy (optionally substituted with halo, $C_1$-$C_6$alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$ alkyl, $C_1$-$C_6$ alkoxy, $C_1$-$C_6$haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, $C_2$-$C_{10}$ heteroalkyl, and oxo (=O). Wherever a group is described as "optionally substituted" that group can be substituted with the above substituents.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. Non-limiting examples include formyl, acetyl, propanoyl, benzoyl, and acryl.

An "heteroacyl" refers to —C(=O)R, wherein R is a $C_{1-6}$ heteroalkyl.

An "alkyloxymethylene" refers to —$CH_2OR$, wherein R is a $C_{1-6}$ alkyl, or heteroalkyl, all optionally substituted.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "sulfonyl" group refers to an "—$SO_2R$" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-sulfonamido" group refers to a "—$N(R_A)SO_2R_B$" group in which $R_A$ and $R_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-carbamyl" group refers to a "—OC(=O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-carbamyl" group refers to an "—$N(R_A)C(=O)OR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-thiocarbamyl" group refers to a "—OC(=S)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-thiocarbamyl" group refers to an "—N($R_A$)C(=S)O$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-amido" group refers to a "—C(=O)N$R_A R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein each optionally substituted with one or more substituents selected from the group consisting of —OH, $C_{1-6}$ alkyl, $C_{3-7}$ carbocyclyl, $C_{6-10}$ aryl, 5-10 membered heteroaryl, 3-10 membered heterocycyl, $C_{1-6}$ alkyl optionally substituted with $C_{1-6}$ alkoxy or —OH and $C_{1-6}$ alkoxy optionally substituted with $C_{1-6}$ alkoxy or —OH.

An "N-amido" group refers to a "—N($R_A$)C(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein each optionally substituted with one or more substituents selected from the group consisting of —OH, $C_{1-6}$ alkyl, $C_{3-7}$ carbocyclyl, $C_{6-10}$ aryl, 5-10 membered heteroaryl, 3-10 membered heterocycyl, $C_{1-6}$ alkyl optionally substituted with $C_{1-6}$ alkoxy or —OH and $C_{1-6}$ alkoxy optionally substituted with $C_{1-6}$ alkoxy or —OH.

An "amino" group refers to a "—N$R_A R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. A non-limiting example includes free amino (i.e., —$NH_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

The term "acyloxy" refers to —OC(O)R where R is alkyl.

The term "alkoxy" or "alkyloxy" refers to OR where R is alkyl, or heteroalkyl, all optionally substituted.

The term "carboxyl" refers to a C(O)OH.

The term "oxo" refers to an =O group.

The term "halogen" or "halo" refers to F (fluoro), Cl (chloro), Br (bromo) and I (iodo).

The term "haloalkyl" refer to alkyl groups containing at least one halogen, in a further aspect are 1 to 3 haloatoms. Suitable haloatoms include F, Cl, and Br.

The term "haloacyl" refer to —C(O)-haloalkyl groups.

The term "alkenyl" refers to unsaturated groups which have 2 to 12 atoms and contain at least one carbon carbon double bond and includes straight chain, branched chain and cyclic groups. Alkenyl groups may be optionally substituted. Suitable alkenyl groups include allyl.

The term "alkynyl" refers to unsaturated groups which have 2 to 12 atoms and contain at least one carbon carbon triple bond and includes straight chain, branched chain and cyclic groups. Alkynyl groups may be optionally substituted. Suitable alkynyl groups include ethynyl.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Heteroaryl groups may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In some embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

As used herein, "cycloalkyl" means a fully saturated carbocyclyl ring or ring system. Examples include cyclopropyl, cyclobutyl, cyclopentyl, and cyclohexyl. The cycloalkyl group may have 3 to 10 carbon atoms (whenever it appears herein, a numerical range such as "3 to 10" refers to each integer in the given range. The cycloalkyl group may be designated as "$C_3$-$C_8$ cycloalkyl" or similar designations. By way of example only, "$C_3$-$C_8$ cycloalkyl" indicates that there are three to eight carbon atoms in the carbocyclyl ring or ring system.

As used herein, "heterocyclyl" means a non-aromatic cyclic ring or ring structure that is fully saturated or partially saturated and includes at least one heteroatom selected from nitrogen, oxygen, and sulfur in the ring backbone. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocycloalkyl group may be designated as "3-15-membered heterocycloalkyl," "4-10-membered heterocycloalkyl," "3-15-membered $C_{2\text{-}14}$heterocycloalkyl," "5-9-membered $C_{4\text{-}8}$heterocycloalkyl," "5-10-membered $C_{4\text{-}9}$heterocycloalkyl," "5-membered $C_{3\text{-}4}$heterocycloalkyl," "6-membered $C_{4\text{-}5}$heterocycloalkyl," "7-membered $C_{5\text{-}6}$heterocycloalkyl," "bicyclic or tricyclic 9-15-membered $C_{8\text{-}14}$heterocycloalkyl," "monocyclic or bicyclic 3-10-membered $C_{2\text{-}9}$heterocycloalkyl," "bicyclic 8-10-membered $C_{4\text{-}9}$heterocycloalkyl," "bicyclic 8-10-membered $C_{5\text{-}9}$heterocycloalkyl," "monocyclic 4-7-membered $C_{3\text{-}6}$_heterocycloalkyl," "monocyclic 5-6-membered $C_{3\text{-}5}$_heterocycloalkyl," or similar designations. The heterocyclyl group could also be a $C_2$-$C_9$ heterocyclyl having 3 to 10 ring members with from one up to three of O (oxygen), N (nitrogen) or S (sulfur). The heterocyclyl group may be designated as "3-10 membered $C_2$-$C_9$ heterocyclyl" or similar designations. In preferred six membered monocyclic heterocyclyls, the heteroatom(s) are selected from one up to three of O (oxygen), N (nitrogen) or S (sulfur), and in preferred five membered monocyclic heterocyclyls, the heteroatom(s) are selected from one or two heteroatoms selected from O (oxygen), N (nitrogen) or S (sulfur). Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "cyclic acetal" refers to a cyclic group containing the following moiety wherein the two oxygens form part of the ring backbone:

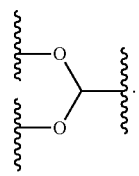 [SMILES: *OC(*)O*]

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atoms to which they are attached," it is meant that the collective unit of the atoms and the two R groups are the recited ring. The ring is not otherwise limited by the definition of each R group when taken individually. For example, when the following substructure is present:

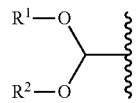

and $R^1$ and $R^2$ are defined as selected from the group consisting of alkyl and aryl, or $R^1$ and $R^2$ together with the oxygen to which they are each attached form a heterocyclyl, it is meant that $R^1$ and $R^2$ can be selected from alkyl or aryl, or alternatively, the substructure has structure:

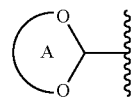

where ring A is a heterocyclic ring containing the depicted oxygens.

Similarly, when two "adjacent" R groups are said to form a ring "together with the atom to which they are attached," it is meant that the collective unit of the atoms, intervening bonds, and the two R groups are the recited ring. For example, when the following substructure is present:

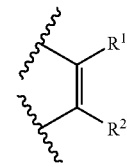

and $R^1$ and $R^2$ are defined as selected from the group consisting of hydrogen and alkyl, or $R^1$ and $R^2$ together with the atoms to which they are attached form an aryl or carbocylyl, it is meant that $R^1$ and $R^2$ can be selected from hydrogen or alkyl, or alternatively, the substructure has structure:

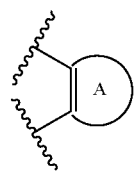

where A is an aryl ring or a carbocylyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

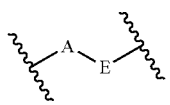

includes the substituent being oriented such that the A is attached at the leftmost attachment point of the molecule as well as the case in which A is attached at the rightmost attachment point of the molecule.

The phrase "therapeutically effective amount" means an amount of a compound or a combination of compounds that partially or fully ameliorates, attenuates or eliminates one or more of the symptoms of a particular disease or condition or prevents, modifies, or delays the onset of one or more of the symptoms of a particular disease or condition. Such amount can be administered as a single dosage or can be administered according to a regimen, whereby it is effective. Repeated administration may be needed to achieve a desired result (e.g., treatment of the disease and/or condition).

The term "pharmaceutically acceptable salt" includes salts of compounds of Formula I, II, and III derived from the combination of a compound of the present embodiments and an organic or inorganic acid or base. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, adipic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzenesulfonic acid, methanesulfonic acid, ethanesulfonic acid, p-toluenesulfonic acid, (+)-7,7-dimethyl-2-oxobicyclo[2.2.1]heptane-1-methanesulfonic acid, 1,2-ethanedisulfonic acid, dodecyl sulfonic acid, salicylic acid, glucoheptonic acid, gluconic acid, glucuronic acid, hippuric acid, hydrochloride hemiethanolic acid, 2-hydroxyethanesulfonic acid, lactic acid, lactobionic acid, methylbromide acid, methyl sulfuric acid, 2-naphthalenesulfonic acid, oleic acid, 4,4'-methylen-ebis-[3-hydroxy-2-naphthalenecarboxylic acid], polygalac-turonic acid, stearic acid, sulfosalicylic acid, tannic acid, terphthalic acid and the like. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

Where the number of any given substituent is not specified (e.g., "haloalkyl"), there may be one or more substituents present. For example, "haloalkyl" can include one or more of the same or different halogens. For example, "haloalkyl" includes each of the substituents $CF_3$, $CHF_2$ and $CH_2F$.

The term "patient" refers to an animal being treated including a mammal, such as a dog, a cat, a cow, a horse, a sheep, and a human. In some embodiments, the patient is a mammal, either male or female. In some embodiments, the patient is a male or female human.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g. HO—, HS—, HOOC—, HOOPR2-, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are examples, not exhaustive, and one skilled in the art could prepare other known varieties of prodrugs. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site specific delivery of the compound.

The term "stereoisomer" refers to the relative or absolute spatial relationship of the R group(s) attached to the stereogenic centers either carbon or phosphorus atoms, and refers to individual or any combination of the individual isomers such as a racemic mixture and a diastereomeric mixture. When a compound has two stereogenic centers, there are 4 potential stereoisomers.

The term "liver" refers to the liver organ.

The term "liver specificity" refers to the ratio:

[drug or a drug metabolite in liver tissue]/[drug or a drug metabolite in blood or another tissue]

as measured in animals treated with the drug or a prodrug. The ratio can be determined by measuring tissue levels at a specific time or may represent an AUC (area under a curve) based on values measured at three or more time points.

The term "increased or enhanced liver specificity" refers to an increase in liver specificity ratio in animals treated with the prodrug relative to animals treated with the parent drug.

The term "enhanced oral bioavailability" refers to an increase of at least about 50% of the absorption of the dose of the reference drug. In an additional aspect, the increase in oral bioavailability of the compound (compared to the reference drug) is at least about 100%, or a doubling of the absorption. Measurement of oral bioavailability usually refers to measurements of the prodrug, drug, or drug metabolite in blood, plasma, tissues, or urine following oral administration compared to measurements following parenteral administration.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "sustained delivery" refers to an increase in the period in which there is a prolongation of therapeutically-effective drug levels due to the presence of the prodrug.

The terms "treating" or "treatment" of a disease includes inhibiting the disease (slowing or arresting or partially arresting its development), preventing the disease, providing relief from the symptoms or side effects of the disease (including palliative treatment), and/or relieving the disease (causing regression of the disease).

The terms "biological agent" refers to a compound that has biological activity or that has molecular properties that can be used for therapeutic or diagnosis purposes, such as a compound carrying a radioactive isotope or a heavy atom.

The terms "molecular pathway" refers to a series of molecular events in tissues such as a receptor modulating sequence, an enzyme modulating sequence, or a biosynthesis sequence that is involved in physiological or pathophysiological functions of a living animal.

Administration and Pharmaceutical Compositions

The disclosed compounds may be used alone or in combination with other treatments. These compounds, when used in combination with other agents, may be administered as a daily dose or an appropriate fraction of the daily dose (e.g., bid). The compounds may be administered after a course of treatment by another agent, during a course of therapy with another agent, administered as part of a therapeutic regimen, or may be administered prior to therapy with another agent in a treatment program.

Examples of pharmaceutically acceptable salts include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfosalicylate, tannate, tartrate, terphthalate, tosylate, and triethiodide.

Compositions containing the active ingredient may be in any form suitable for the intended method of administration. In some embodiments, the compounds of a method and/or composition described herein can be provided via oral administration, rectal administration, transmucosal administration, intestinal administration, enteral administration, topical administration, transdermal administration, intrathecal administration, intraventricular administration, intraperitoneal administration, intranasal administration, intraocular administration and/or parenteral administration.

When the compounds are administered via oral administration, for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient can be mixed with an inert solid diluent, for example calcium phosphate or kaolin, or as soft gelatin capsules wherein the active ingredient can be mixed with water or an oil medium, such as peanut oil, liquid paraffin or olive oil.

Formulations suitable for parenteral administration include aqueous and non-aqueous isotonic sterile injection solutions which may contain, for example, antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

In some embodiments unit dosage formulations contain a daily dose or unit, daily sub-dose, or an appropriate fraction thereof, of a drug. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

The actual dose of the compounds described herein depends on the specific compound, and on the condition to be treated; the selection of the appropriate dose is well within the knowledge of the skilled artisan. In some embodiments, a daily dose may be from about 0.1 mg/kg to about 100 mg/kg or more of body weight, from about 0.25 mg/kg or less to about 50 mg/kg from about 0.5 mg/kg or less to about 25 mg/kg, from about 1.0 mg/kg to about 10 mg/kg of body weight. Thus, for administration to a 70 kg person, the dosage range would be from about 7 mg per day to about 7000 mg per day, from about 35 mg per day or less to about 2000 mg per day or more, from about 70 mg per day to about 1000 mg per day.

Methods of Treatment

Some embodiments of the present invention include methods of treating a disease, disorder or condition is selected from the group consisting of hepatitis, liver cancer, liver fibrosis, fatty liver, malaria, viral infection, parasitic infection, diabetes, hyperlipidemia, atherosclerosis, obesity, dyslipidemia, hyperglycemia, a hormonal condition, HIV, and various types of cancer with the compounds, and compositions comprising compounds described herein. Some methods include administering a compound, composition, pharmaceutical composition described herein to a subject in need thereof. In some embodiments, a subject can be an animal, e.g., a mammal, a human. In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament or additional therapeutic agent(s). By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment, the agents are administered through the same route, such as orally. In another embodiment, the agents are administered through different routes, such as one being administered orally and another being administered i.v.

Examples of additional medicaments include a therapeutic agent(s) selected from the group consisting of other types of chemotherapies such as cyclophosphamide, methotrexate, doxorubicin, docetaxel, cisplatin, epirubicin, oxaliplatin, and folinic acid; and other targeted antitumor agents such as HDAC inhibitors. In some embodiments, the additional therapeutic agent for HCC treatment may be one or more of sorafenib, regorafenib, an immune-oncology agent such as a PD-1 or PD-L1 checkpoint inhibitor.

Examples of additional medicaments also include a medical procedure selected from the group consisting of tumor ablation, selective internal radiation therapy (SIRT), and trans-arterial chemoembolization (TACE).

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Synthesis of Compounds

The following procedures for the preparation of the new compounds illustrate the general procedures used to prepare the 5-fluorouracil derived acetal and hemiaminal ether compounds.

Scheme I describes general strategies of synthesis of the compounds of Formula I. 5-Fluorouracil (1) is reacted with an alkylating agent of structure 2 in the presence of a base to give a product of structure 3 that can be further reacted with the second alkylating agent of structure 4 in the presence of a base to give the final product of structure 5. Alternatively, fluorouracil can be double alkylated in one step to yield the final product of structure 5 if the two alkylating agents are identical.

Scheme I

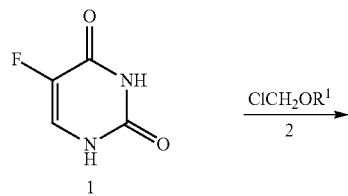

Compounds of Formula II and IV are synthesized in a manner similar to that of Scheme I with doxifluridine as the starting material. Scheme II describes general strategies of synthesis of the compounds of Formula III and V. Doxifluridine (6) is condensed with an aldehyde of structure 7 in the presence of an acid catalyst under a standard condition to produce the ketal product of structure 8 that can be further reacted with an alkylating or acylating agent of structure 9 to afford the final product of structure 10.

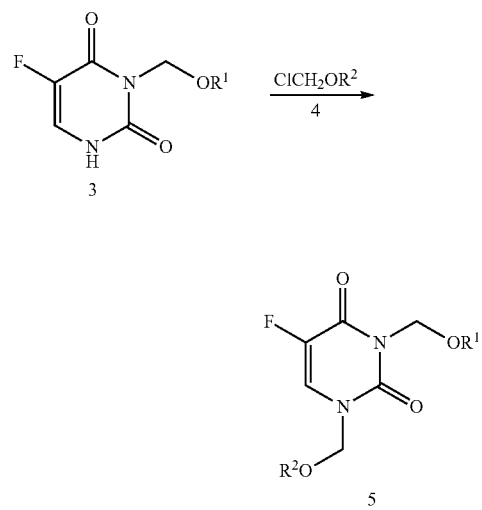

Scheme II

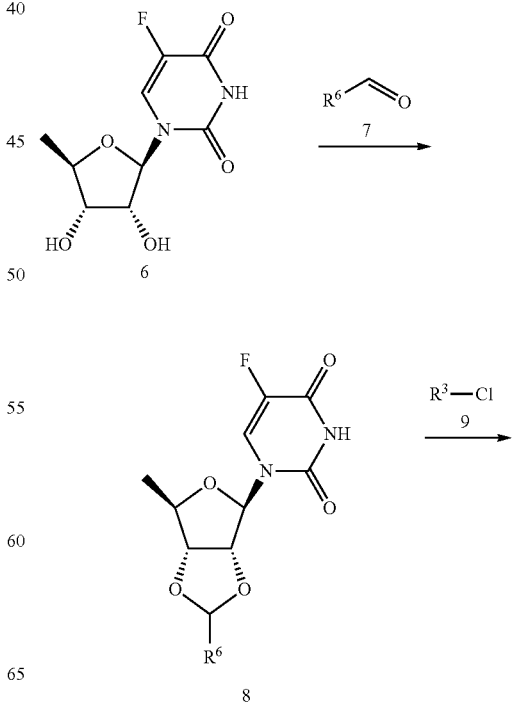

41
-continued

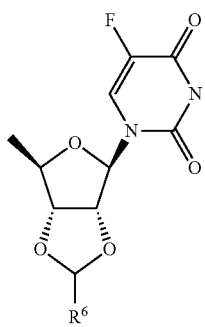

10

Scheme III describes general synthesis of the compounds of Formula VI. Floxuridine (11) reacts with the phosphane-diamine (12) in the presence of 4,5-dicyanoimidazole to give the cyclic product of structure 13 and the crude reaction mixture is then treated with an oxidation agent such as tert-butyl hydroperoxide to afford the final product of structure 14.

Scheme III

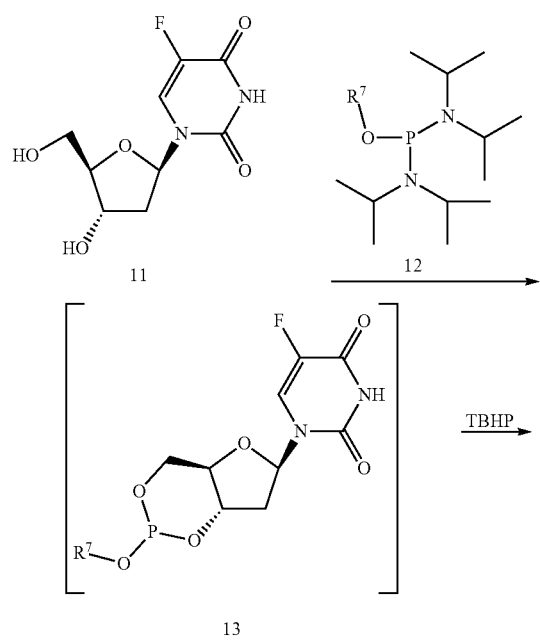

$R^7$ has any of the values described herein

42
EXAMPLES

Some compounds of Formula I, II, III, IV, V, and VI are prepared as outlined below.

Example 1

1-((Benzyloxy)methyl)-5-fluoropyrimidine-2,4(1H, 3H)-dione (Compound 101)

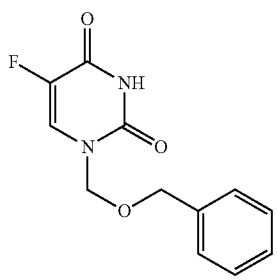 [SMILES: O=c1[nH]c(=O)n(COCc2ccccc2)cc1F]

Compound 101 was prepared according to Scheme I from chloromethyl benzylether and 5-fluorouracil. To a solution of 5-fluorouracil (1.0 g, 7.7 mmol)) in dichloromethane in the presence of excess amount of DIPEA was added chloromethyl benzylether (1.2 g, 7.7 mmol) and the resulting solution was stirred at room temperature overnight. Standard work-up followed by Pre-HPLC to give compound 101 (190 mg, 10%). [M–H]$^-$ calculated for $C_{12}H_{11}FN_2O_3$: 249.07; found: 249.1. $^1$H-NMR (CDCl$_3$, 400 MHz) 8.22 (bs, 1H), 7.40-7.30 (m, 6H), 5.21 (s, 2H), and 4.63 (s, 2H).

Example 2

3-((Benzyloxy)methyl)-5-fluoropyrimidine-2,4(1H, 3H)-dione (Compound 102)

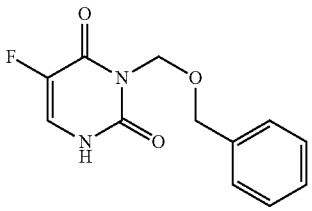 [SMILES: O=c1[nH]cc(F)c(=O)n1COCc1ccccc1]

Compound 102 was isolated from the reaction described in Example 1 in 18% yield. [M–H]$^-$ calculated for $C_{12}H_{11}FN_2O_3$: 249.07; found: 249.1. $^1$H-NMR (CDCl$_3$, 400 MHz) 9.33 (bs, 1H), 7.40-7.28 (m, 5H), 7.23 (d, J=7.0, 1H), 5.49 (s, 2H), and 4.71 (s, 2H).

Example 3

1,3-bis-((Benzyloxy)methyl)-5-fluoropyrimidine-2,4 (1H,3H)-dione (Compound 103)

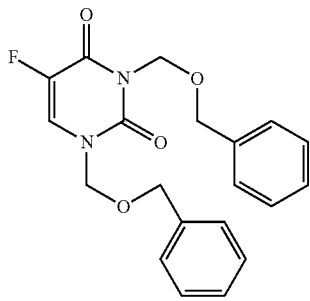 [SMILES: O=c1c(F)cn(COCc2ccccc2)c(=O)n1COCc1ccccc1]

Compound 103 was isolated from the reaction described in Example 1 in 25% yield. [M−H]⁻ calculated for $C_2H_{19}FN_2O_4$: 369.12; found: 369.0. ¹H-NMR (CDCl₃, 400 MHz) 7.40-7.26 (m, 11H), 5.50 (s, 2H), 5.23 (s, 2H), 4.71 (s, 2H), and 4.62 (s, 2H).

Example 4

1,3-bis-((Ethyloxy)methyl)-5-fluoropyrimidine-2,4 (1H,3H)-dione (Compound 104)

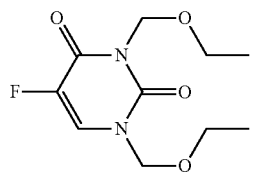 [SMILES: CCOCn1cc(F)c(=O)n(COCC)c1=O]

Compound 104 was prepared according to Scheme I from chloromethyl ethylether and 5-fluorouracil. [M+H]⁺ calculated for $C_{10}H_{15}FN_2O_4$: 247.11; found: 247.1.

Example 5

3-((Benzyloxy)methyl)-1-((2R,3R,4S,5R)-3,4-dihydroxy-5-methyltetrahydrofuran-2-yl)-5-fluoropyrimidine-2,4(1H,3H)-dione (Compound 105)

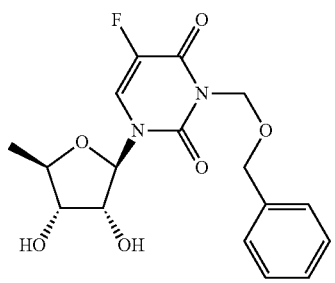 [SMILES: C[C@H]1O[C@@H](n2cc(F)c(=O)n(COCc3ccccc3)c2=O)[C@H](O)[C@@H]1O]

Compound 105 was prepared according to the method similar to Scheme I from chloromethyl benzylether and doxifluridine. [M+H]⁺ calculated for $C_{17}H_{19}FN_2O_6$: 367.13; found: 367.1.

Example 6

1-((2R,3R,4R,5R)-3-((Benzyloxy)methoxy)-4-hydroxy-5-methyltetrahydrofuran-2-yl)-3-((benzyloxy)methyl)-5-fluoropyrimidine-2,4(1H,3H)-dione (Compound 106)

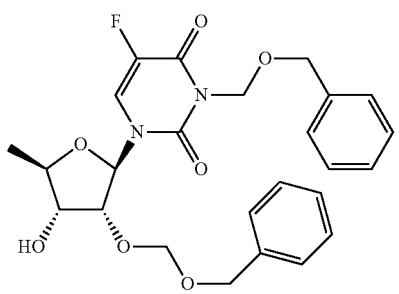 [SMILES: C[C@H]1O[C@@H](n2cc(F)c(=O)n(COCc3ccccc3)c2=O)[C@H](OCOCc2ccccc2)[C@@H]1O]

Compound 106 was prepared according to the method similar to Scheme I from chloromethyl benzylether and doxifluridine. [M+H2O]⁺ calculated for $C_{25}H_{27}FN_2O_7$: 504.19; found: 504.2.

Example 7

1-((2R,3R,4R,5R)-4-((Benzyloxy)methoxy)-4-hydroxy-5-methyltetrahydrofuran-2-yl)-3-((benzyloxy)methyl)-5-fluoropyrimidine-2,4(1H,3H)-dione (Compound 107)

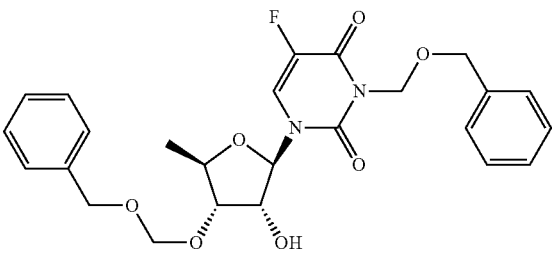 [SMILES: C[C@H]1O[C@@H](n2cc(F)c(=O)n(COCc3ccccc3)c2=O)[C@H](O)[C@@H]1OCOCc1ccccc1]

Compound 107 was prepared according to the method similar to Scheme I from chloromethyl benzylether and doxifluridine. [M+H2O]⁺ calculated for $C_{25}H_{27}FN_2O_7$: 504.19; found: 504.2.

Example 8

1-((2R,3R,4R,5R)-3-(Ethoxymethoxy)-4-hydroxy-5-methyltetrahydrofuran-2-yl)-3-(ethoxymethyl)-5-fluoropyrimidine-2,4(1H,3H)-dione (Compound 108)

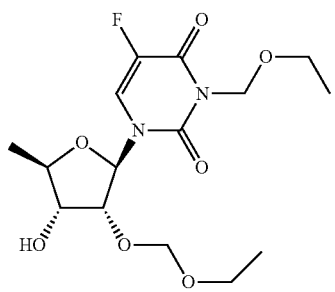 [SMILES: CCOCO[C@@H]1[C@H](O)[C@@H](C)O[C@H]1n1cc(F)c(=O)n(COCC)c1=O]

Compound 108 was prepared according to the method similar to Scheme I from chloromethyl ethylether and doxifluridine. $^1$H-NMR (CDC$_3$, 400 MHz) 7.41 (d, J=6.0, 1H), 5.84 (s, 1H), 5.45 (d, J=10.0, 1H), 5.41 (d, J=10.0, 1H), 4.97 (d, J=6.8, 1H), 4.88 (d, J=6.8, 1H), 4.18 (dd, J=5.6 and 2.0, 1H), 4.11-4.01 (m, 1H), 3.75-3.60 (m, 5H), 2.85 (d, J=8.4, 1H), 1.47 (d, J=6.0, 3H), and 1.22 (t, J=7.2, 6H).

Example 9

1-((2R,3R,4R,5R)-4-(Ethoxymethoxy)-3-hydroxy-5-methyltetrahydrofuran-2-yl)-3-(ethoxymethyl)-5-fluoropyrimidine-2,4(1H,3H)-dione (Compound 109)

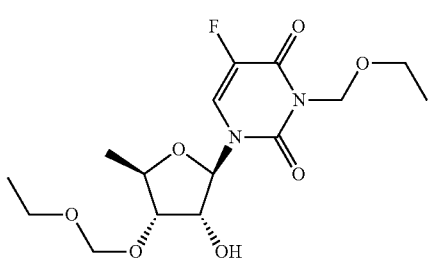 [SMILES: CCOCO[C@H]1[C@@H](O)[C@H](n2cc(F)c(=O)n(COCC)c2=O)O[C@@H]1C]

Compound 109 was prepared according to the method similar to Scheme I from chloromethyl ethylether and doxifluridine. $^1$H-NMR (CDC$_3$, 400 MHz) 7.41 (d, J=6.4, 1H), 5.74 (d, J=3.6, 1H), 5.44 (d, J=11.2, 1H), 5.41 (d, J=11.2, 1H), 4.81 (d, J=6.8, 1H), 4.77 (d, J=6.8, 1H), 4.24-4.20 (m, 2H), 3.83 (t, J=6.0, 1H), 3.72-3.65 (m, 4H), 1.44 (d, J=6.4, 3H), 1.24 (t, J=7.2, 3H), and 1.22 (d, J=7.2, 3H).

Example 10

Pentyl(1-((2R,3R,4S,5R)-3,4-dihydroxy-5-methyltetrahydrofuran-2-yl)-5-fluoro-2-oxo-1,2-dihydropyrimidin-4-yl)(ethoxymethyl)carbamate (Compound 110)

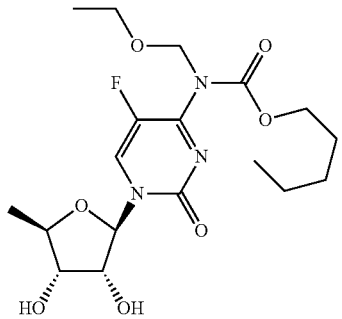 [SMILES: CCCCCOC(=O)N(COCC)c1nc(=O)n([C@@H]2O[C@H](C)[C@@H](O)[C@H]2O)cc1F]

Compound 110 was prepared according to the method similar to Scheme I from chloromethyl ethylether and capecitabine. $^1$H-NMR (CDCl$_3$, 400 MHz) 7.97 (d, J=6.4, 1H), 5.69 (d, J=4.4, 1H), 5.37 (d, J=10.4, 1H), 5.33 (d, J=10.4, 1H), 4.45-4.35 (m, 1H), 4.30-4.20 (m, 3H), 3.91 (t, J=4.4, 1H), 3.65 (q, J=6.8, 2H), 1.70-1.64 (m, 2H), 1.40 (d, J=6.4, 3H), 1.35-1.30 (m, 4H), 1.18 (t, J=6.8, 3H), and 0.90 (t, J=6.8, 3H).

Example 11

Pentyl (1-((2R,3R,4S,5R)-3,4-dihydroxy-5-methyltetrahydrofuran-2-yl)-3-(ethoxymethyl)-5-fluoro-2-oxo-2,3-dihydropyrimidin-4(1H)-ylidene)carbamate (Compound 111)

Compound 111 was prepared according to the method similar to Scheme I from chloromethyl ethylether and capecitabine. $^1$H-NMR (CDCl$_3$, 400 MHz) 7.37 (d, J=7.2, 1H), 5.57 (d, J=3.2, 1H), 5.51 (d, J=9.6, 1H), 5.46 (d, J=9.6, 1H), 4.35-4.25 (m, 1H), 4.25-4.15 (m, 4H), 3.92-3.88 (m, 1H), 3.73 (q, J=6.8, 2H), 3.0 (d, J=4.4, 1H), 1.75-1.66 (m, 2H), 1.40 (d, J=6.4, 3H), 1.43-1.35 (m, 4H), 1.23 (t, J=7.2, 3H), and 0.93 (t, J=7.2, 3H).

Example 12

Pentyl (1-((3aR,4R,6R,6aR)-2,6-dimethyltetrahydro-furo[3,4-d][1,3]dioxol-4-yl)-5-fluoro-2-oxo-1,2-dihydropyrimidin-4-yl)carbamate (Compound 112)

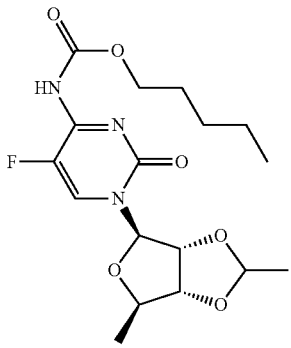

Compound 112 was prepared according to the method described in Scheme II from ethaldehyde and capecitabine. [M+1]$^+$ calculated for $C_{17}H_{24}FN_3O_6$: 386.17; found: 386.1.

Example 13

1-((3aR,4R,6R,6aR)-2-(3,5-Dimethylphenyl)-6-methyltetrahydrofuro[3,4-d][1,3]dioxol-4-yl)-5-fluoropyrimidine-2,4(1H,3H)-dione (Compound 113)

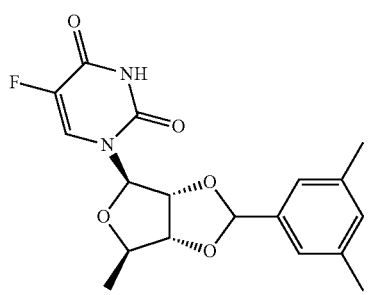

Compound 113 was prepared according to the method described in Scheme II from 3,5-dimethylbenzaldehyde and capecitabine and isolated as a 3:1 mixture of 2 stereoisomers. [M+1]$^+$ calculated for $C_{18}H_{19}FN_2O_5$: 363.14; found: 363.1.

Example 14

1-((3aR,4R,6R,6aR)-2-(Benzo[d][1,3]dioxol-5-yl)-6-methyltetrahydrofuro[3,4-d][1,3]dioxol-4-yl)-5-fluoropyrimidine-2,4(1H,3H)-dione (Compound 114)

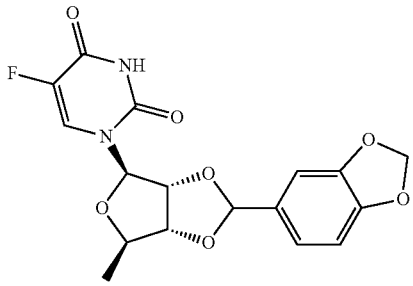

Compound 114 was prepared according to the method described in Scheme II from benzo[d][1,3]dioxole-5-carbaldehyde and capecitabine and isolated as a 3:1 mixture of 2 stereoisomers. [M+1]$^+$ calculated for $C_{17}H_{15}FN_2O_7$: 379.1; found: 379.0.

Example 15

1-((3aR,4R,6R,6aR)-2-(2-(4-Ethyl-1,3-dioxolan-2-yl)phenyl)-6-methyltetrahydrofuro[3,4-d][1,3]dioxol-4-yl)-5-fluoropyrimidine-2,4(1H,3H)-dione (Compound 115)

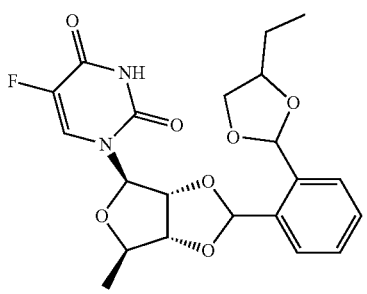

Compound 115 was prepared according to the method described in Scheme II from 2-(4-ethyl-1,3-dioxolan-2-yl)benzaldehyde and capecitabine and isolated as a mixture of stereoisomers. [M+1]$^+$ calculated for $C_{21}H_{23}FN_2O_7$: 435.16; found: 435.1.

Example 16

5-Fluoro-1-((3aR,4R,6R,6aR)-2-(4-hydroxyphenyl)-6-methyltetrahydrofuro[3,4-d][1,3]dioxol-4-yl)pyrimidine-2,4(1H,3H)-dione (Compound 116)

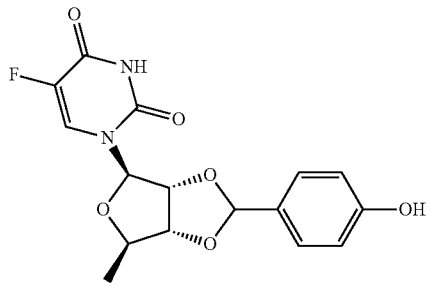

Compound 116 was prepared according to the method described in Scheme II from 4-hydroxybenzaldehyde and capecitabine and isolated as a 6:1 mixture of 2 stereoisomers. [M+1]$^+$ calculated for $C_{16}H_{15}FN_2O_6$: 351.1; found: 351.0.

Example 17

3-(Ethoxymethyl)-5-fluoro-1-((3aR,4R,6R,6aR)-2-(4-hydroxyphenyl)-6-methyltetrahydrofuro[3,4-d][1,3]dioxol-4-yl)pyrimidine-2,4(1H,3H)-dione (Compound 117)

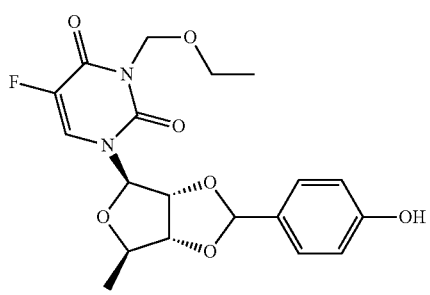

Compound 117 was prepared according to the method described in Scheme II from chloromethyl ethylether, 4-hydroxybenzaldehyde, and capecitabine and isolated as a mixture of 2 stereoisomers. [M+1]$^+$ calculated for $C_{19}H_{21}FN_2O_7$: 409.14; found: 409.1.

Example 18

5-Fluoro-1-((3aR,4R,6R,6aR)-2-(4-methoxyphenyl)-6-methyltetrahydrofuro[3,4-d][1,3]dioxol-4-yl)pyrimidine-2,4(1H,3H)-dione (Compound 118)

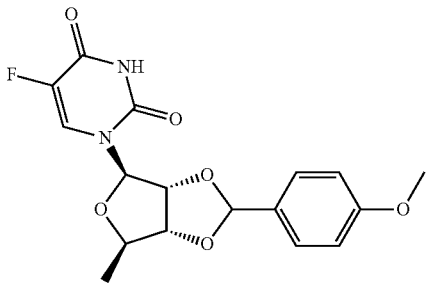

Compound 118 was prepared according to the method described in Scheme II from 4-methoxybenzaldehyde and capecitabine and isolated as a mixture of 2 stereoisomers. [M+1]$^+$ calculated for $C_{17}H_{17}FN_2O_6$: 365.12; found: 365.1.

Example 19

4-((3aR,4R,6R,6aR)-4-(5-Fluoro-2,4-dioxo-3,4-dihydropyrimidin-1(2H)-yl)-6-methyltetrahydrofuro[3,4-d][1,3]dioxol-2-yl)phenyl Isobutyrate (Compound 119)

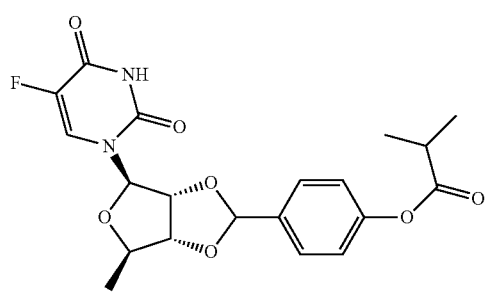

Compound 119 was prepared according to the method described in Scheme II from 4-hydroxybenzaldehyde, capecitabine, and isobutyric acid, and isolated as a mixture of 2 stereoisomers. [M+1]$^+$ calculated for $C_2H_{21}FN_2O_7$: 421.24; found: 421.1.

Example 20

1-((3aR,4R,6R,6aR)-2-(4-(Ethoxymethoxy)phenyl)-6-methyltetrahydrofuro[3,4-d][1,3]dioxol-4-yl)-5-fluoropyrimidine-2,4(1H,3H)-dione (Compound 120)

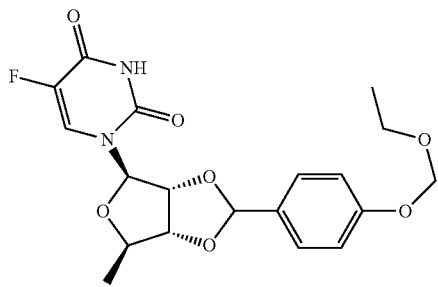

Compound 120 was prepared according to the method described in Scheme II from 4-methoxybenzaldehyde, capecitabine, and chloromethyl ethylether, and isolated as a mixture of 2 stereoisomers. $^1$H-NMR (CDC$_3$, 400 MHz) 7.41-7.36 (m, 3H), 6.85 (d, J=8.4, 2H), 5.93 (s, 1H), 5.75 (d, J=2.4, 1H), 1.47 (d, J=10, 3H).

Example 21

1-((4aR,6R,7aS)-2-(3,5-Dimethylphenyl)tetrahydro-4H-furo[3,2-d][1,3]dioxin-6-yl)-5-fluoropyrimidine-2,4(1H,3H)-dione (Compound 121)

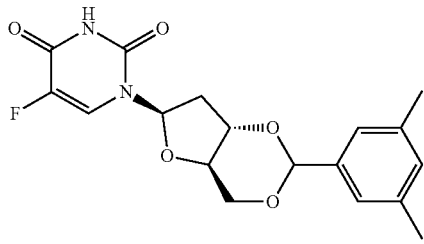

Compound 121 can be made according to the method described in Scheme II from 4-methoxybenzaldehyde and floxuridine.

Example 22

5-Fluoro-1-((4aR,6R,7aS)-2-oxido-2-phenoxytetrahydro-4H-furo[3,2-d][1,3,2]dioxaphosphinin-6-yl)pyrimidine-2,4(1H,3H)-dione (Compound 122)

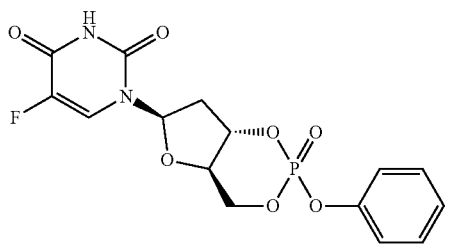

Compound 122 was prepared according to the method described in Scheme III from N,N,N',N'-tetraisopropyl-1-phenoxyphosphanediamine and floxuridine, and isolated as a mixture of 2 stereoisomers. [M+1]$^+$ calculated for C$_{15}$H$_{14}$FN$_2$O$_7$P: 385.06; found: 385.0.

Example 23

5-Fluoro-1-((2S,4aR,6R,7aS)-2-oxido-2-phenoxytetrahydro-4H-furo[3,2-d][1,3,2]dioxaphosphinin-6-yl)pyrimidine-2,4(1H,3H)-dione (Compound 123)

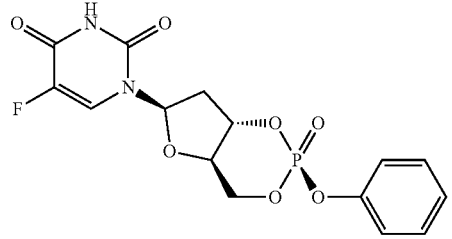 [SMILES: O=c1[nH]c(=O)n([C@H]2C[C@@H]3O[P@@](=O)(Oc4ccccc4)OC[C@H]3O2)cc1F]

Compound 123 was isolated by HPLC from Compound 122.

Example 24

5-Fluoro-1-((2R,4aR,6R,7aS)-2-oxido-2-phenoxytetrahydro-4H-furo[3,2-d][1,3,2]dioxaphosphinin-6-yl)pyrimidine-2,4(1H,3H)-dione (Compound 124)

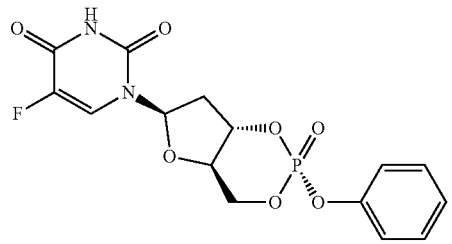 [SMILES: O=c1[nH]c(=O)n([C@H]2C[C@@H]3O[P@](=O)(Oc4ccccc4)OC[C@H]3O2)cc1F]

Compound 124 was isolated by HPLC from Compound 122.

Example 25

5-Fluoro-1-((4aR,6R,7aS)-2-oxido-2-(4-chlorophenoxy)tetrahydro-4H-furo[3,2-d][1,3,2]dioxaphosphinin-6-yl)pyrimidine-2,4(1H,3H)-dione (Compound 125)

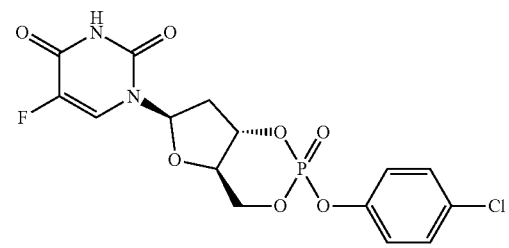

Compound 125 was prepared according to the method described in Scheme III from N,N,N',N'-tetraisopropyl-1-(4-chlorophenoxy)phosphanediamine and floxuridine, and isolated as a single isomer. $^1$H-NMR (MeOD, 400 MHz) 7.92 (d, J=6.4, 1H), 7.43 (dd, J=6.8 and 1.2, 2H), 7.32 (dd, J=7.6 and 1.2, 2H), 6.26 (dd, J=7.6 and 3.5, 1H).

Example 26

1-((4aR,6R,7aS)-2-(Benzyloxy)-2-oxidotetrahydro-4H-furo[3,2-d][1,3,2]dioxaphosphinin-6-yl)-5-fluoropyrimidine-2,4(1H,3H)-dione (Compound 126)

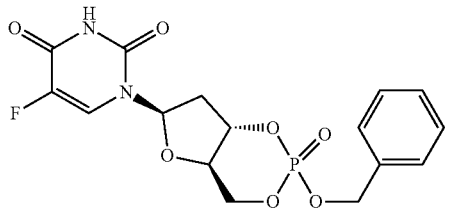

Compound 126 was prepared according to the method described in Scheme III from N,N,N',N'-tetraisopropyl-1-benzyloxyphosphanediamine and floxuridine, and isolated as a mixture of two isomers. [M+1]$^+$ calculated for $C_{16}H_{16}FN_2O_7P$: 399.08; found: 399.0.

Example 27

1-((4aR,6R,7aS)-2-(4-Chlorobenzyloxy)-2-oxidotetrahydro-4H-furo[3,2-d][1,3,2]dioxaphosphinin-6-yl)-5-fluoropyrimidine-2,4(1H,3H)-dione (Compound 127)

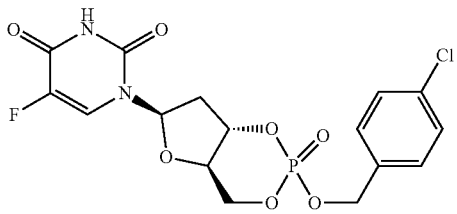

Compound 127 was prepared according to the method described in Scheme III from N,N,N',N'-tetraisopropyl-1-(4-chlorobenzyloxy)phosphanediamine and floxuridine, and isolated as a single isomer (absolute stereochemistry is not signed). [M+1]+ calculated for $C_{16}H_{15}ClFN_2O_7P$: 433.04; found: 433.0.

Example 28

5-Fluoro-1-((4aR,6R,7aS)-2-(naphthalen-1-ylmethoxy)-2-oxidotetrahydro-4H-furo[3,2-d][1,3,2]dioxaphosphinin-6-yl)pyrimidine-2,4(1H,3H)-dione (Compound 128)

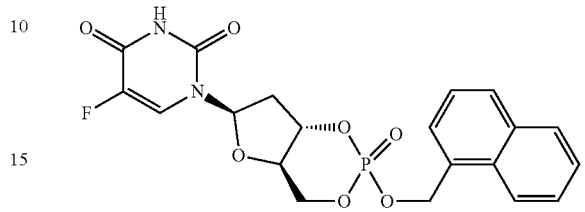

Compound 128 was prepared according to the method described in Scheme III from N,N,N',N'-tetraisopropyl-1-(1-naphthalenylmethoxy)phosphanediamine and floxuridine, and isolated as a single isomer (absolute stereochemistry is not signed). [M−1]$^+$ calculated for $C_{20}H_{18}FN_2O_7P$: 447.07; found: 447.1.

Example 29

1-((4aR,6R,7aS)-2-(3-Chlorobenzyloxy)-2-oxidotetrahydro-4H-furo[3,2-d][1,3,2]dioxaphosphinin-6-yl)-5-fluoropyrimidine-2,4(1H,3H)-dione (Compound 129)

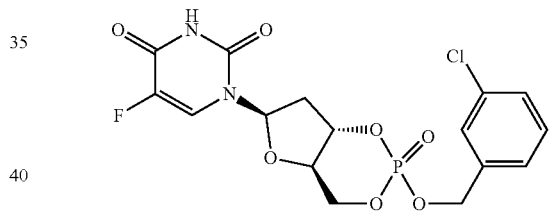

Compound 129 was prepared according to the method described in Scheme III from N,N,N',N'-tetraisopropyl-1-(3-chlorobenzyloxy)phosphanediamine and floxuridine, and isolated as a mixture of two isomers. [M−1]$^+$ calculated for $C_{16}H_{15}ClFN_2O_7P$: 431.02; found: 431.0.

Example 30

1-((4aR,6R,7aS)-2-(2-Chlorobenzyloxy)-2-oxidotetrahydro-4H-furo[3,2-d][1,3,2]dioxaphosphinin-6-yl)-5-fluoropyrimidine-2,4(1H,3H)-dione (Compound 130)

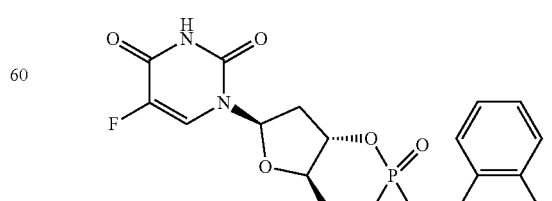

Compound 130 was prepared according to the method described in Scheme III from N,N,N',N'-tetraisopropyl-1-(2-chlorobenzyloxy)phosphanediamine and floxuridine, and isolated as a mixture of two isomers. [M−1]+ calculated for $C_{16}H_{15}ClFN_2O_7P$: 431.02; found: 431.0.

Example 31

5-Fluoro-1-((4aR,6R,7aS)-2-(hexyloxy)-2-oxidotetrahydro-4H-furo[3,2-d][1,3,2]dioxaphosphinin-6-yl)pyrimidine-2,4(1H,3H)-dione (Compound 131)

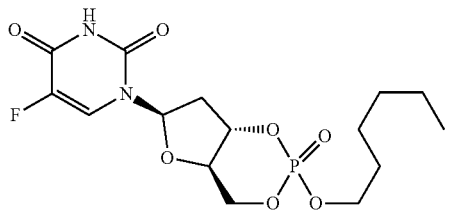

Compound 131 was prepared according to the method described in Scheme III from N,N,N',N'-tetraisopropyl-1-hexyloxyphosphanediamine and floxuridine, and isolated as a mixture of two isomers. [M−1]+ calculated for $C_{15}H_{20}FN_2O_7P$: 391.10; found: 391.0.

Example 32

5-Fluoro-1-((4aR,6R,7aS)-2-(nonyloxy)-2-oxidotetrahydro-4H-furo[3,2-d][1,3,2]dioxaphosphinin-6-yl)pyrimidine-2,4(1H,3H)-dione (Compound 132)

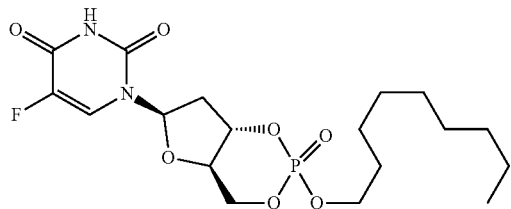

Compound 132 was prepared according to the method described in Scheme III from N,N,N',N'-tetraisopropyl-1-nonyloxyphosphanediamine and floxuridine, and isolated as a mixture of two isomers. [M−1]+ calculated for $C_{18}H_{28}FN_2O_7P$: 433.15; found: 433.1.

Example 33

5-Fluoro-1-((4aR,6R,7aS)-2-(nonan-5-yloxy)-2-oxidotetrahydro-4H-furo[3,2-d][1,3,2]dioxaphosphinin-6-yl)pyrimidine-2,4(1H,3H)-dione (Compound 133)

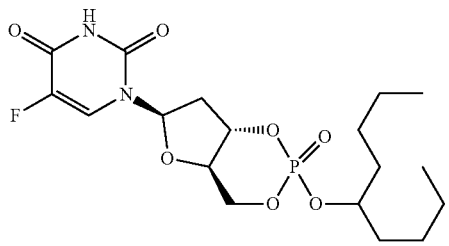

Compound 133 was prepared according to the method described in Scheme III from N,N,N',N'-tetraisopropyl-1-(nonan-5-yloxy)phosphanediamine and floxuridine, and isolated as a mixture of two isomers. [M−1]+ calculated for $C_{18}H_{28}FN_2O_7P$: 433.15; found: 433.1.

Example 34

3-(((4aR,6R,7aS)-6-(5-Fluoro-2,4-dioxo-3,4-dihydropyrimidin-1(2H)-yl)-2-oxidotetrahydro-4H-furo[3,2-d][1,3,2]dioxaphosphinin-2-yl)oxy)propanenitrile (Compound 134)

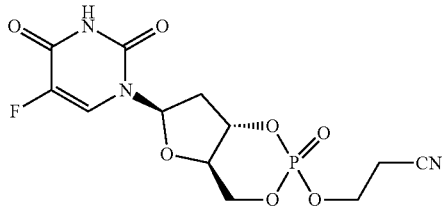

Compound 134 was prepared according to the method described in Scheme III from N,N,N',N'-tetraisopropyl-1-(2-cyanoethyloxy)phosphanediamine and floxuridine, and isolated as a single isomer (absolute stereochemistry is not signed). [M+1]+ calculated for $C_{12}H_{13}FN_3O_7P$: 362.06; found: 362.0.

Example 35

5-Fluoro-1-((4aR,6R,7aS)-2-oxido-2-(((S)-4-(prop-1-en-2-yl)cyclohex-1-en-1-yl)methoxy)tetrahydro-4H-furo[3,2-d][1,3,2]dioxaphosphinin-6-yl)pyrimidine-2,4(1H,3H)-dione (Compound 135)

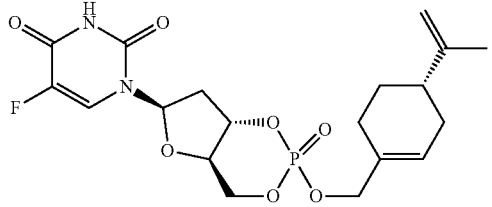

Compound 135 was prepared according to the method described in Scheme III from (S)—N,N,N',N'-tetraisopropyl-1-((4-(prop-1-en-2-yl)cyclohex-1-en-1-yl)methanoxy)phosphanediamine and floxuridine, and isolated as a mixture of two isomers. [M−1]+ calculated for $C_{15}H_{20}FN_2O_7P$: 441.12; found: 441.1.

Example 36

1-((4aR,6R,7aS)-2-(4-Fluorobenzyloxy)-2-oxidotetrahydro-4H-furo[3,2-d][1,3,2]dioxaphosphinin-6-yl)-5-fluoropyrimidine-2,4(1H,3H)-dione (Compound 136)

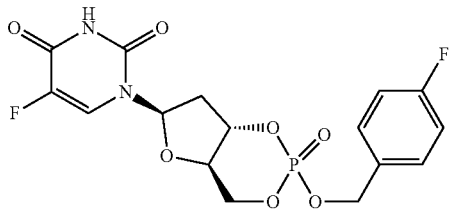

Compound 136 was prepared according to the method described in Scheme III from N,N,N',N'-tetraisopropyl-1-(4-fluorobenzyloxy)phosphanediamine and floxuridine, and isolated as a mixture of two isomers. [M−1]+ calculated for $C_{16}H_{15}F_2N_2O_7P$: 415.05; found: 415.0.

Example 37

1-((4aR,6R,7aS)-2-(3,4-Difluorobenzyloxy)-2-oxidotetrahydro-4H-furo[3,2-d][1,3,2]dioxaphosphinin-6-yl)-5-fluoropyrimidine-2,4(1H,3H)-dione (Compound 137)

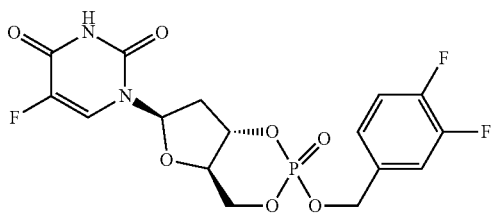

Compound 137 was prepared according to the method described in Scheme III from N,N,N',N'-tetraisopropyl-1-(3,4-difluorobenzyloxy)phosphanediamine and floxuridine, and isolated as a mixture of two isomers. [M+1]+ calculated for $C_{16}H_{14}F_3N_2O_7P$: 435.06; found: 435.0.

Example 38

1-((4aR,6R,7aS)-2-(2,4-Difluorobenzyloxy)-2-oxidotetrahydro-4H-furo[3,2-d][1,3,2]dioxaphosphinin-6-yl)-5-fluoropyrimidine-2,4(1H,3H)-dione (Compound 138)

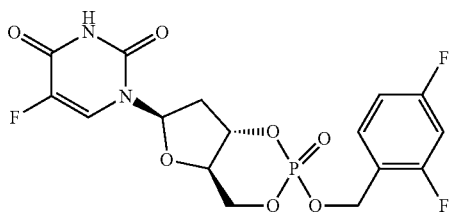

Compound 138 was prepared according to the method described in Scheme III from N,N,N',N'-tetraisopropyl-1-(2,4-difluorobenzyloxy)phosphanediamine and floxuridine, and isolated as a mixture of two isomers. [M−1]+ calculated for $C_{16}H_{14}F_3N_2O_7P$: 433.04; found: 433.0.

Example 39

1-((4aR,6R,7aS)-2-(2-Fluorobenzyloxy)-2-oxidotetrahydro-4H-furo[3,2-d][1,3,2]dioxaphosphinin-6-yl)-5-fluoropyrimidine-2,4(1H,3H)-dione (Compound 139)

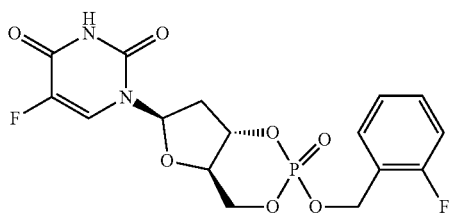

Compound 139 was prepared according to the method described in Scheme III from N,N,N',N'-tetraisopropyl-1-(2-fluorobenzyloxy)phosphanediamine and floxuridine, and isolated as a mixture of two isomers. [M−1]+ calculated for $C_{16}H_{15}F_2N_2O_7P$: 415.05; found: 415.0.

Example 40

5-Fluoro-1-((2S,4aR,6R,7aS)-2-((2-fluorobenzyl)oxy)-2-oxidotetrahydro-4H-furo[3,2-d][1,3,2]dioxaphosphinin-6-yl)pyrimidine-2,4(1H,3H)-dione (Compound 140)

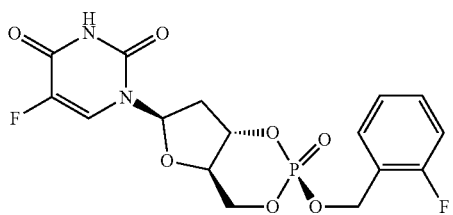 [SMILES: O=c1[nH]c(=O)n([C@H]2C[C@@H]3O[P@@](=O)(OCc4ccccc4F)OC[C@H]3O2)cc1F]

Compound 140 was isolated from Compound 139 by HPLC.

Example 41

5-Fluoro-1-((2R,4aR,6R,7aS)-2-((2-fluorobenzyl)oxy)-2-oxidotetrahydro-4H-furo[3,2-d][1,3,2]dioxaphosphinin-6-yl)pyrimidine-2,4(1H,3H)-dione (Compound 141)

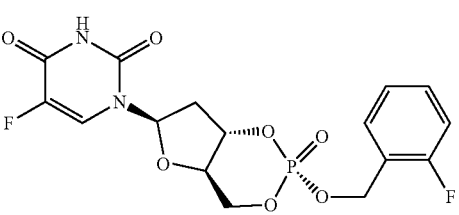 [SMILES: O=c1[nH]c(=O)n([C@H]2C[C@@H]3O[P@](=O)(OCc4ccccc4F)OC[C@H]3O2)cc1F]

Compound 141 was isolated from Compound 139 by HPLC.

Example 42

1-((4aR,6R,7aS)-2-(4-Chloro-2-fluorobenzyloxy)-2-oxidotetrahydro-4H-furo[3,2-d][1,3,2]dioxaphosphinin-6-yl)-5-fluoropyrimidine-2,4(1H,3H)-dione (Compound 142)

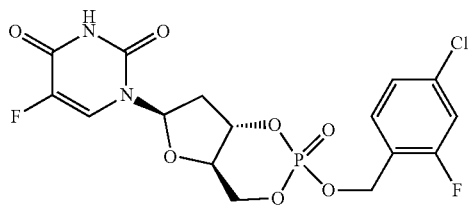

Compound 142 was prepared according to the method described in Scheme III from N,N,N',N'-tetraisopropyl-1-(4-chloro-2-fluorobenzyloxy)phosphanediamine and floxuridine, and isolated as a mixture of two isomers. [M−1]+ calculated for $C_{16}H_{14}ClF_2N_2O_7P$: 449.01; found: 449.0.

Example 43

1-((4aR,6R,7aS)-2-(2-Chloro-4-fluorobenzyloxy)-2-oxidotetrahydro-4H-furo[3,2-d][1,3,2]dioxaphosphinin-6-yl)-5-fluoropyrimidine-2,4(1H,3H)-dione (Compound 143)

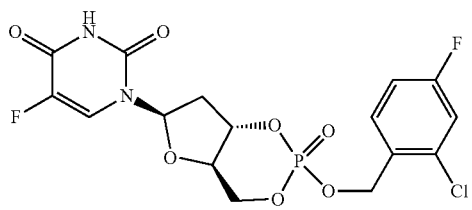

Compound 143 was prepared according to the method described in Scheme III from N,N,N',N'-tetraisopropyl-1-(2-chloro-4-fluorobenzyloxy)phosphanediamine and floxuridine, and isolated as a mixture of two isomers. [M−1]+ calculated for $C_{16}H_{14}ClF_2N_2O_7P$: 449.01; found: 449.0.

Example 44

1-((4aR,6R,7aS)-2-(2,4,6-Trifluorobenzyloxy)-2-oxidotetrahydro-4H-furo[3,2-d][1,3,2]dioxaphosphinin-6-yl)-5-fluoropyrimidine-2,4(1H,3H)-dione (Compound 144)

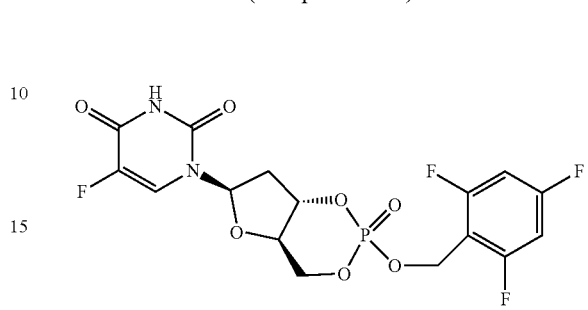

Compound 144 was prepared according to the method described in Scheme III from N,N,N',N'-tetraisopropyl-1-(2,4,6-trifluorobenzyloxy)phosphanediamine and floxuridine, and isolated as a mixture of two isomers. [M−1]− calculated for $C_{16}H_{13}F_4N_2O_7P$: 451.03; found: 451.0.

Example 45

5-Fluoro-1-((2S,4aR,6R,7aS)-2-oxido-2-((2,4,6-trifluorobenzyl)oxy)tetrahydro-4H-furo[3,2-d][1,3,2]dioxaphosphinin-6-yl)pyrimidine-2,4(1H,3H)-dione (Compound 145)

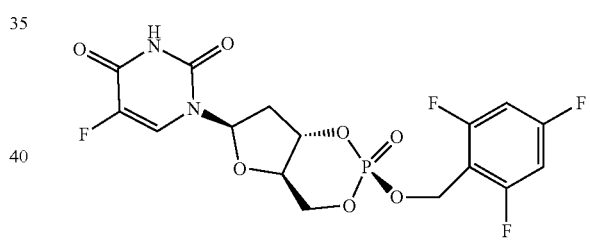

Compound 145 was isolated by HPLC from Compound 144.

Example 46

5-Fluoro-1-((2R,4aR,6R,7aS)-2-oxido-2-((2,4,6-trifluorobenzyl)oxy)tetrahydro-4H-furo[3,2-d][1,3,2]dioxaphosphinin-6-yl)pyrimidine-2,4(1H,3H)-dione (Compound 146)

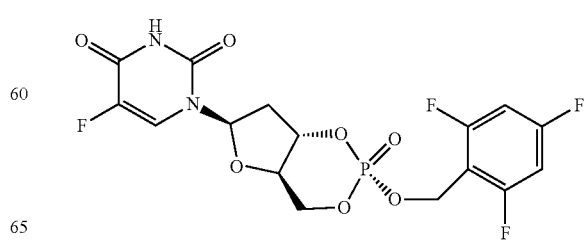

Example 47

1-((4aR,6R,7aS)-2-(4-Ethylbenzyloxy)-2-oxidotetrahydro-4H-furo[3,2-d][1,3,2]dioxaphosphinin-6-yl)-5-fluoropyrimidine-2,4(1H,3H)-dione (Compound 147)

Compound 146 was isolated by HPLC from Compound 144.

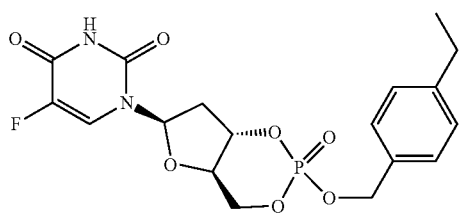

Compound 147 was prepared according to the method described in Scheme III from N,N,N',N'-tetraisopropyl-1-(4-ethylbenzyloxy)phosphanediamine and floxuridine, and isolated as a mixture of two isomers. [M−1]$^+$ calculated for $C_{18}H_{20}FN_2O_7P$: 425.09; found: 424.75.

Example 48

1-((4aR,6R,7aS)-2-(4-Isopropylbenzyloxy)-2-oxidotetrahydro-4H-furo[3,2-d][1,3,2]dioxaphosphinin-6-yl)-5-fluoropyrimidine-2,4(1H,3H)-dione (Compound 148)

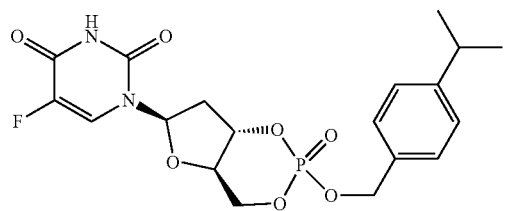

Compound 148 was prepared according to the method described in Scheme III from N,N,N',N'-tetraisopropyl-1-(4-isopropylbenzyloxy)phosphanediamine and floxuridine, and isolated as a mixture of two isomers. [M+1]$^+$ calculated for $C_{19}H_{22}FN_2O_7P$: 439.10; found: 439.1.

Example 49

1-((4aR,6R,7aS)-2-(4-tert-Butylbenzyloxy)-2-oxidotetrahydro-4H-furo[3,2-d][1,3,2]dioxaphosphinin-6-yl)-5-fluoropyrimidine-2,4(1H,3H)-dione (Compound 149)

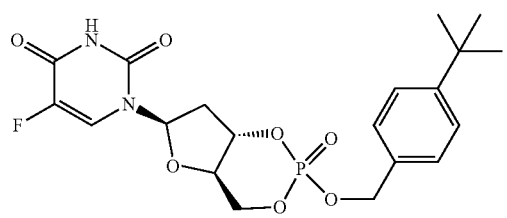

Compound 149 was prepared according to the method described in Scheme III from N,N,N',N'-tetraisopropyl-1-(4-tert-butylbenzyloxy)phosphanediamine and floxuridine, and isolated as a mixture of two isomers. [M−1]$^+$ calculated for $C_{20}H_{24}FN_2O_7P$: 453.12; found: 453.1.

Example 50

1-((4aR,6R,7aS)-2-(3,5-Dimethylbenzyloxy)-2-oxidotetrahydro-4H-furo[3,2-d][1,3,2]dioxaphosphinin-6-yl)-5-fluoropyrimidine-2,4(1H,3H)-dione (Compound 150)

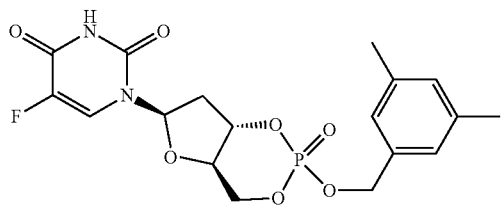

Compound 150 was prepared according to the method described in Scheme III from N,N,N',N'-tetraisopropyl-1-(3,5-dimethylbenzyloxy)phosphanediamine and floxuridine, and isolated as a mixture of two isomers. [M−1]$^+$ calculated for $C_{18}H_{20}FN_2O_7P$: 425.09; found: 425.0.

Example 51

1-((4aR,6R,7aS)-2-(2,4-Dichlorobenzyloxy)-2-oxidotetrahydro-4H-furo[3,2-d][1,3,2]dioxaphosphinin-6-yl)-5-fluoropyrimidine-2,4(1H,3H)-dione (Compound 151)

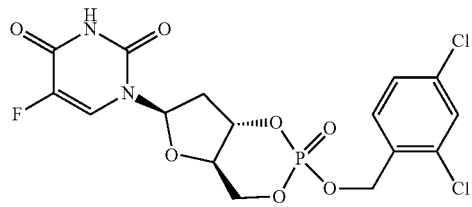

Compound 151 was prepared according to the method described in Scheme III from N,N,N',N'-tetraisopropyl-1-(2,4-dichlorobenzyloxy)phosphanediamine and floxuridine, and isolated as a mixture of two isomers. [M−1]$^+$ calculated for $C_{16}H_{14}Cl_2FN_2O_7P$: 464.97; found: 464.9.

Example 52

1-((4aR,6R,7aS)-2-(2,6-Dichlorobenzyloxy)-2-oxidotetrahydro-4H-furo[3,2-d][1,3,2]dioxaphosphinin-6-yl)-5-fluoropyrimidine-2,4(1H,3H)-dione (Compound 152)

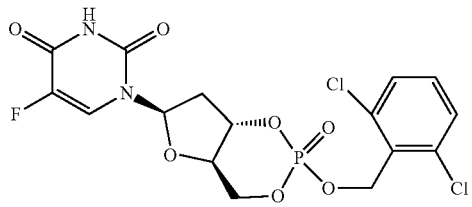

Compound 152 was prepared according to the method described in Scheme III from N,N,N',N'-tetraisopropyl-1-(2,6-dichlorobenzyloxy)phosphanediamine and floxuridine, and isolated as a mixture of two isomers. [M+1]$^+$ calculated for $C_{16}H_{14}Cl_2FN_2O_7P$: 466.99; found: 466.9.

Example 53

1-((4aR,6R,7aS)-2-(2,6-Difluorobenzyloxy)-2-oxidotetrahydro-4H-furo[3,2-d][1,3,2]dioxaphosphinin-6-yl)-5-fluoropyrimidine-2,4(1H,3H)-dione (Compound 153)

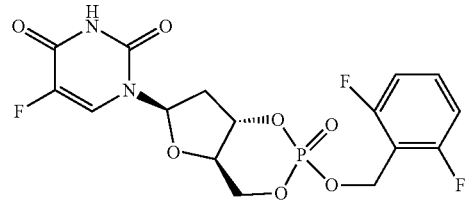

Compound 153 was prepared according to the method described in Scheme III from N,N,N',N'-tetraisopropyl-1-(2,6-difluorobenzyloxy)phosphanediamine and floxuridine, and isolated as a mixture of two isomers. [M−1]$^+$ calculated for $C_{16}H_{14}F_3N_2O_7P$: 433.04; found: 433.0.

Example 54

1-((4aR,6R,7aS)-2-(3-Fluorobenzyloxy)-2-oxidotetrahydro-4H-furo[3,2-d][1,3,2]dioxaphosphinin-6-yl)-5-fluoropyrimidine-2,4(1H,3H)-dione (Compound 154)

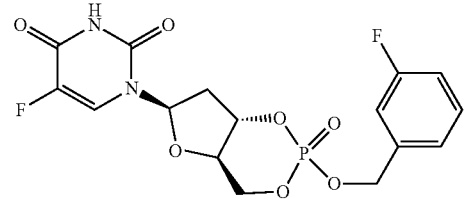

Compound 154 was prepared according to the method described in Scheme III from N,N,N',N'-tetraisopropyl-1-(3-fluorobenzyloxy)phosphanediamine and floxuridine, and isolated as a mixture of two isomers. [M−1]$^+$ calculated for $C_{16}H_{15}F_2N_2O_7P$: 415.05; found: 415.0.

Example 55

1-((4aR,6R,7aS)-2-(2-Fluoro-5-methoxybenzyloxy)-2-oxidotetrahydro-4H-furo[3,2-d][1,3,2]dioxaphosphinin-6-yl)-5-fluoropyrimidine-2,4(1H,3H)-dione (Compound 155)

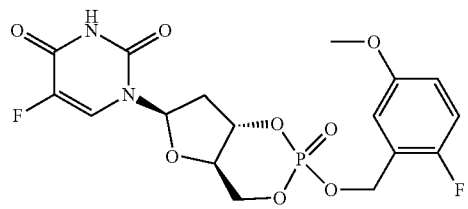

Compound 155 was prepared according to the method described in Scheme III from N,N,N',N'-tetraisopropyl-1-(2-fluoro-5-methoxybenzyloxy)phosphanediamine and floxuridine, and isolated as a mixture of two isomers. [M−1]$^+$ calculated for $C_{17}H_{17}F_2N_2O_8P$: 445.06; found: 445.0.

Example 56

5-Fluoro-1-((4aR,6R,7aS)-2-oxido-2-((4-(trifluoromethyl)benzyl)oxy)tetrahydro-4H-furo[3,2-d][1,3,2]dioxaphosphinin-6-yl)pyrimidine-2,4(1H,3H)-dione (Compound 156)

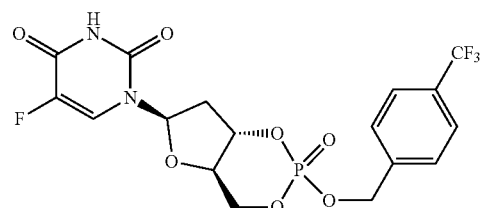

Compound 156 was prepared according to the method described in Scheme III from N,N,N',N'-tetraisopropyl-1-((4-(trifluoromethyl)benzyloxy)phosphanediamine and floxuridine, and isolated as a mixture of two isomers. [M−1]$^+$ calculated for $C_{17}H_{15}F_4N_2O_7P$: 465.05; found: 464.9.

Example 57

1-((2R,4aR,6R,7aS)-2-((4-Ethylbenzyl)amino)-2-oxidotetrahydro-4H-furo[3,2-d][1,3,2]dioxaphosphinin-6-yl)-5-fluoropyrimidine-2,4(1H,3H)-dione (Compound 157)

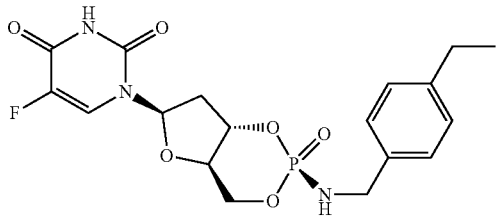 [SMILES: CCc1ccc(CN[P@@]2(=O)OC[C@H]3O[C@@H](n4cc(F)c(=O)[nH]c4=O)C[C@@H]3O2)cc1]

Compound 157 was prepared according to the method described in Scheme III from N,N,N',N'-tetraisopropyl-1-((4-ethylbenzylamino)phosphanediamine and floxuridine. [M+1]$^+$ calculated for $C_{18}H_{21}FN_3O_6P$: 426.13; found: 426.2.

Example 58

1-((2S,4aR,6R,7aS)-2-((4-Ethylbenzyl)amino)-2-oxidotetrahydro-4H-furo[3,2-d][1,3,2]dioxaphosphinin-6-yl)-5-fluoropyrimidine-2,4(1H,3H)-dione (Compound 158)

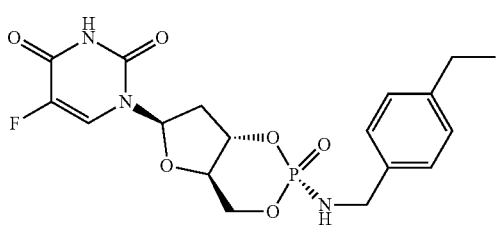 [SMILES: CCc1ccc(CN[P@]2(=O)OC[C@H]3O[C@@H](n4cc(F)c(=O)[nH]c4=O)C[C@@H]3O2)cc1]

Compound 158 was isolated from the reaction of Compound 157. [M+1]$^+$ calculated for $C_{18}H_{21}FN_3O_6P$: 426.13; found: 426.2.

Example 59

1-((2R,4aR,6R,7aS)-2-((2,4-Difluorobenzyl)amino)-2-oxidotetrahydro-4H-furo[3,2-d][1,3,2]dioxaphosphinin-6-yl)-5-fluoropyrimidine-2,4(1H,3H)-dione (Compound 159)

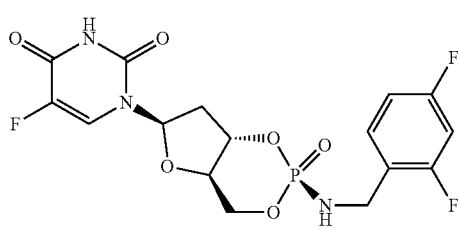 [SMILES: O=c1[nH]c(=O)n([C@H]2C[C@@H]3O[P@@](=O)(NCc4ccc(F)cc4F)OC[C@H]3O2)cc1F]

Compound 159 was prepared according to the method described in Scheme III from N,N,N',N'-tetraisopropyl-1-((2,4-difluorobenzylamino)phosphanediamine and floxuridine. [M+1]$^+$ calculated for $C_{16}H_{15}F_3N_3O_6P$: 434.08; found: 434.25.

Example 60

1-((2S,4aR,6R,7aS)-2-((2,4-Difluorobenzyl)amino)-2-oxidotetrahydro-4H-furo[3,2-d][1,3,2]dioxaphosphinin-6-yl)-5-fluoropyrimidine-2,4(1H,3H)-dione (Compound 160)

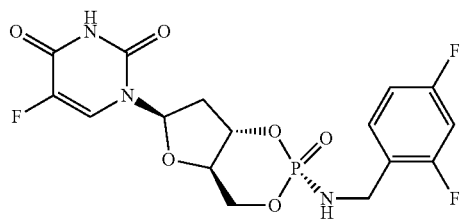 [SMILES: O=c1[nH]c(=O)n([C@H]2C[C@@H]3O[P@](=O)(NCc4ccc(F)cc4F)OC[C@H]3O2)cc1F]

Compound 160 was isolated as a minor isomer. [M+1]$^+$ calculated for $C_{16}H_{15}F_3N_3O_6P$: 434.08; found: 434.25.

Example 61

1-((4aR,6R,7aS)-2-(3,5-Difluorobenzyloxy)-2-oxidotetrahydro-4H-furo[3,2-d][1,3,2]dioxaphosphinin-6-yl)-5-fluoropyrimidine-2,4(1H,3H)-dione (Compound 161)

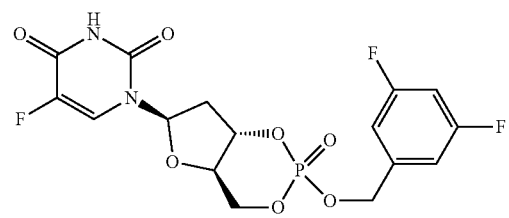

Compound 161 was prepared according to the method described in Scheme III from N,N,N',N'-tetraisopropyl-1-(3,5-difluorobenzyloxy)phosphanediamine and floxuridine, and isolated as a mixture of two isomers. [M−1]$^+$ calculated for $C_{16}H_{14}F_3N_2O_7P$: 433.04; found: 433.0.

Example 62

1-((4aR,6R,7aS)-2-(2,3,4,5,6-Pentafluorobenzyloxy)-2-oxidotetrahydro-4H-furo[3,2-d][1,3,2]dioxaphosphinin-6-yl)-5-fluoropyrimidine-2,4(1H,3H)-dione (Compound 162)

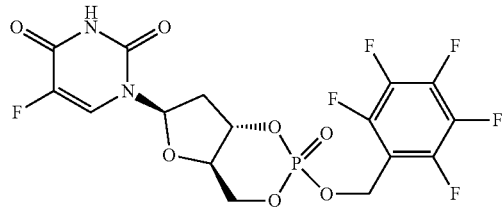

Compound 162 was prepared according to the method described in Scheme III from N,N,N',N'-tetraisopropyl-1-(2,3,4,5,6-pentafluorobenzyloxy)phosphanediamine and floxuridine, and isolated as a mixture of two isomers. [M−1]+ calculated for $C_{16}H_{11}F_6N_2O_7P$: 487.01; found: 487.0.

Example 63

1-((4aR,6R,7aS)-2-(2,3,4-Trifluorobenzyloxy)-2-oxidotetrahydro-4H-furo[3,2-d][1,3,2]dioxaphosphinin-6-yl)-5-fluoropyrimidine-2,4(1H,3H)-dione (Compound 163)

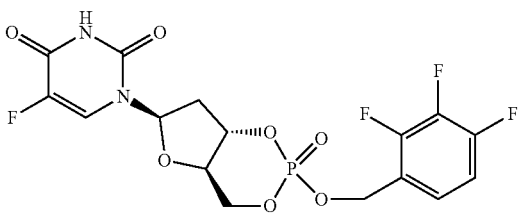

Compound 163 was prepared according to the method described in Scheme III from N,N,N',N'-tetraisopropyl-1-(2,3,4-trifluorobenzyloxy)phosphanediamine and floxuridine, and isolated as a mixture of two isomers. [M−1]+ calculated for $C_{16}H_{13}F_4N_2O_7P$: 451.03; found: 451.0.

Example 64

1-((4aR,6R,7aS)-2-(2,4,5-Trifluorobenzyloxy)-2-oxidotetrahydro-4H-furo[3,2-d][1,3,2]dioxaphosphinin-6-yl)-5-fluoropyrimidine-2,4(1H,3H)-dione (Compound 164)

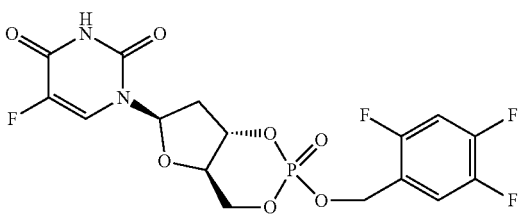

Compound 164 was prepared according to the method described in Scheme III from N,N,N',N'-tetraisopropyl-1-(2,4,5-trifluorobenzyloxy)phosphanediamine and floxuridine, and isolated as a mixture of two isomers. [M+1]+ calculated for $C_{16}H_{13}F_4N_2O_7P$: 453.05; found: 453.0.

Example 65

5-Fluoro-1-((4aR,6R,7aS)-2-(propyloxy)-2-oxidotetrahydro-4H-furo[3,2-d][1,3,2]dioxaphosphinin-6-yl)pyrimidine-2,4(1H,3H)-dione (Compound 165)

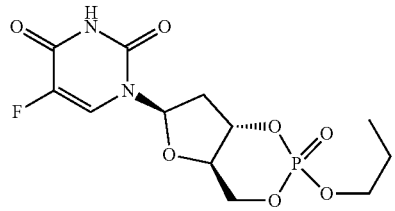

Compound 165 was prepared according to the method described in Scheme III from N,N,N',N'-tetraisopropyl-1-propyloxyphosphanediamine and floxuridine, and isolated as a mixture of two isomers. [M−1]+ calculated for $C_{12}H_{16}FN_2O_7P$: 349.06; found: 349.0.

Example 66

5-Fluoro-1-((4aR,6R,7aS)-2-(2,2,3,3,3-pentafluoropropyloxy)-2-oxidotetrahydro-4H-furo[3,2-d][1,3,2]dioxaphosphinin-6-yl)pyrimidine-2,4(1H,3H)-dione (Compound 166)

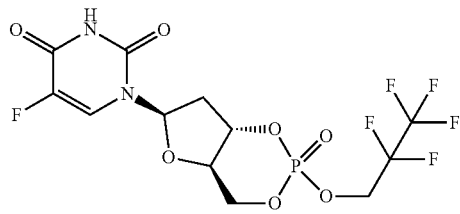

Compound 166 was prepared according to the method described in Scheme III from N,N,N',N'-tetraisopropyl-1-(2,2,3,3,3-pentafluoropropyloxy)phosphanediamine and floxuridine, and isolated as a mixture of two isomers. [M−1]+ calculated for $C_{12}H_{11}F_6N_2O_7P$: 439.01; found: 439.0.

Example 67

1-((4aR,6R,7aS)-2-(2-(Diethoxymethyl)phenoxy)-2-oxidotetrahydro-4H-furo[3,2-d][1,3,2]dioxaphosphinin-6-yl)-5-fluoropyrimidine-2,4(1H,3H)-dione (Compound 167)

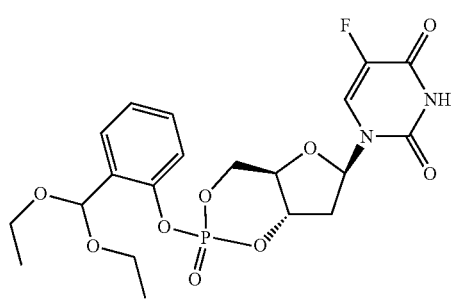

Compound 167 was prepared according to the method described in Scheme III from N,N,N',N'-tetraisopropyl-1-(2-diethoxymethylphenoxy)phosphanediamine and floxuridine, and isolated as a mixture of 2 stereoisomers. [M−1]+ calculated for $C_{20}H_{24}FN_2O_9P$: 485.11; found: 485.1.

Example 68

5-Fluoro-1-((4aR,6R,7aS)-2-(2-fluorophenoxy)-2-oxidotetrahydro-4H-furo[3,2-d][1,3,2]dioxaphosphinin-6-yl)pyrimidine-2,4(1H,3H)-dione (Compound 168)

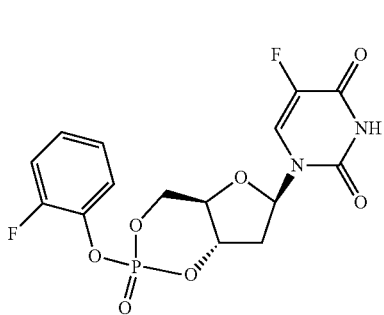

Compound 168 was prepared according to the method described in Scheme III from N,N,N',N'-tetraisopropyl-1-(2-fluorophenoxy)phosphanediamine and floxuridine, and isolated as a mixture of 2 stereoisomers. [M−1]+ calculated for $C_{15}H_{13}F_2N_2O_7P$: 401.03; found: 401.1.

Example 69

(((4aR,6R,7aS)-6-(5-Fluoro-2,4-dioxo-3,4-dihydropyrimidin-1(2H)-yl)-2-oxidotetrahydro-4H-furo[3,2-d][1,3,2]dioxaphosphinin-2-yl)oxy)methyl pivalate (Compound 169)

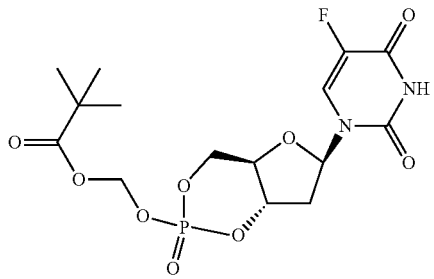

Compound 169 was prepared according to a known method from iodomethyl pivalate and floxuridine, and isolated as a mixture of 2 stereoisomers. [M−1]+ calculated for $C_{15}H_{20}FN_2O_9P$: 421.08; found: 421.1.

Example 70

1-((4aR,6R,7aS)-2-((4-(Ethoxymethoxy)benzyl)oxy)-2-oxidotetrahydro-4H-furo[3,2-d][1,3,2]dioxaphosphinin-6-yl)-5-fluoropyrimidine-2,4(1H,3H)-dione (Compound 170)

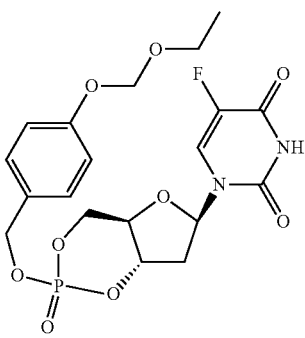

Compound 170 was prepared according the method described in Scheme III from N,N,N',N'-tetraisopropyl-1-(4-ethoxymethoxybenzyloxy)phosphanediamine and floxuridine, and isolated as a mixture of 2 stereoisomers. [M−1]+ calculated for $C_{19}H_{22}FN_2O_9P$: 471.09; found: 471.2.

Example 71

1-((4aR,6R,7aS)-2-(Benzo[d][1,3]dioxol-5-yl-methoxy)-2-oxidotetrahydro-4H-furo[3,2-d][1,3,2]dioxaphosphinin-6-yl)-5-fluoropyrimidine-2,4(1H,3H)-dione (Compound 171)

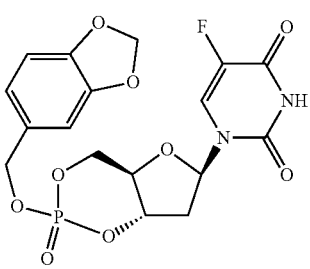

Compound 171 was prepared according the method described in Scheme III from N,N,N',N'-tetraisopropyl-1-(benzo[d][1,3]dioxol-5-ylmethoxy)phosphanediamine and floxuridine, and isolated as a mixture of 2 stereoisomers. [M−1]⁺ calculated for $C_{17}H_{16}FN_2O_9P$: 441.05; found: 441.1.

Example 72

1-((4aR,6R,7aS)-2-((2-(1,3-Dioxolan-2-yl)benzyl)oxy)-2-oxidotetrahydro-4H-furo[3,2-d][1,3,2]dioxaphosphinin-6-yl)-5-fluoropyrimidine-2,4(1H,3H)-dione (Compound 172)

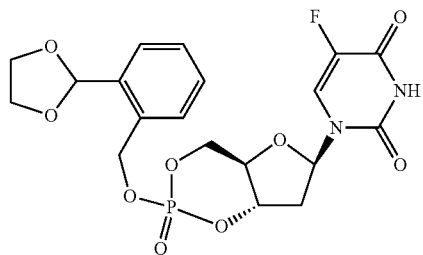

Compound 172 was prepared according the method described in Scheme III from N,N,N',N'-tetraisopropyl-1-(2-(1,3-dioxolan-2-yl)benzyloxy)phosphanediamine and floxuridine, and isolated as a mixture of 2 stereoisomers. [M−1]⁺ calculated for $C_{19}H_{20}FN_2O_9P$: 469.08; found: 469.1.

Example 73

1-((4aR,6R,7aS)-2-(Cyclohexyloxy)-2-oxidotetrahydro-4H-furo[3,2-d][1,3,2]dioxaphosphinin-6-yl)-5-fluoropyrimidine-2,4(1H,3H)-dione (Compound 173)

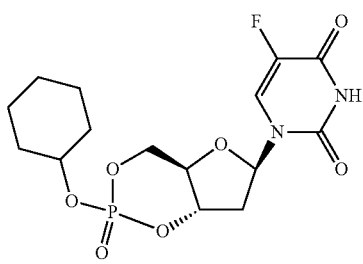

Compound 173 was prepared according the method described in Scheme III from N,N,N',N'-tetraisopropyl-1-cyclohexyloxyphosphanediamine and floxuridine, and isolated as a mixture of 2 stereoisomers. [M−1]⁺ calculated for $C_{15}H_{20}FN_2O_7P$: 389.09; found: 389.1.

Example 74

5-Fluoro-1-((4aR,6R,7aS)-2-isopropoxy-2-oxidotetrahydro-4H-furo[3,2-d][1,3,2]dioxaphosphinin-6-yl)pyrimidine-2,4(1H,3H)-dione (Compound 174)

Compound 174 was prepared according the method described in Scheme III from N,N,N',N'-tetraisopropyl-1-isopropoxyphosphanediamine and floxuridine, and isolated as a mixture of 2 stereoisomers. [M−1]⁺ calculated for $C_{12}H_{16}FN_2O_7P$: 349.06; found: 349.0.

Example 75

1-((4aR,6R,7aS)-2-(Cyclohexylmethoxy)-2-oxidotetrahydro-4H-furo[3,2-d][1,3,2]dioxaphosphinin-6-yl)-5-fluoropyrimidine-2,4(1H,3H)-dione (Compound 175)

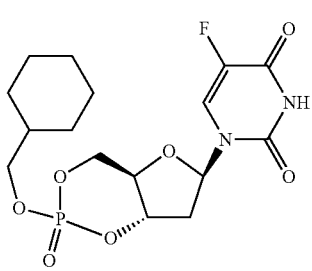

Compound 175 was prepared according the method described in Scheme III from N,N,N',N'-tetraisopropyl-1-cyclohexylmethoxyphosphanediamine and floxuridine, and isolated as a mixture of 2 stereoisomers. [M−1]+ calculated for $C_{16}H_{22}FN_2O_7P$: 403.10; found: 403.1.

Example 76

1-((4aR,6R,7aS)-2-(Pentyloxy)-2-oxidotetrahydro-4H-furo[3,2-d][1,3,2]dioxaphosphinin-6-yl)-5-fluoropyrimidine-2,4(1H,3H)-dione (Compound 176)

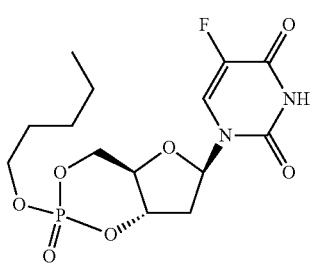

Compound 176 was prepared according the method described in Scheme III from N,N,N',N'-tetraisopropyl-1-pentyloxyphosphanediamine and floxuridine, and isolated as a mixture of 2 stereoisomers. [M−1]+ calculated for $C_{14}H_{20}FN_2O_7P$: 377.09; found: 377.1.

Example 77

1-((4aR,6R,7aS)-2-(2-Phenylethoxy)-2-oxidotetrahydro-4H-furo[3,2-d][1,3,2]dioxaphosphinin-6-yl)-5-fluoropyrimidine-2,4(1H,3H)-dione (Compound 177)

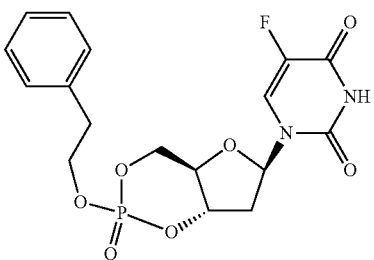

Compound 177 was prepared according the method described in Scheme III from N,N,N',N'-tetraisopropyl-1-(2-phenylethoxy)phosphanediamine and floxuridine, and isolated as a mixture of 2 stereoisomers. [M−1]+ calculated for $C_{17}H_{18}FN_2O_7P$: 411.07; found: 411.1.

Example 78

1-((3aR,4R,6R,6aR)-2-(6-Chlorobenzo[d][1,3]dioxol-5-yl)-6-methyltetrahydrofuro[3,4-d][1,3]dioxol-4-yl)-5-fluoropyrimidine-2,4(1H,3H)-dione (Compound 178)

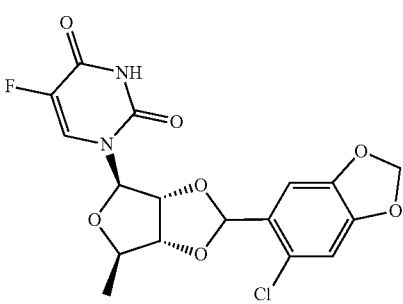

Compound 178 was prepared according to the method described in Scheme II from benzo[d][1,3]dioxole-4-chloro-5-carbaldehyde and capecitabine and isolated as a 1:1 mixture of two stereoisomers. [M+1]+ calculated for $C_{17}H_{14}ClFN_2O_7$: 413.06; found: 413.0.

Example 79

1-((3aR,4R,6R,6aR)-2-(6-Fluorobenzo[d][1,3]di-oxol-5-yl)-6-methyltetrahydrofuro[3,4-d][1,3]dioxol-4-yl)-5-fluoropyrimidine-2,4(1H,3H)-dione (Compound 179)

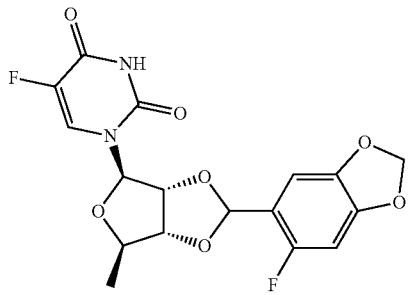

Compound 179 was prepared according to the method described in Scheme II from benzo[d][1,3]dioxole-4-fluoro-5-carbaldehyde and capecitabine and isolated as a 1:1 mixture of two stereoisomers. [M−1]⁺ calculated for $C_{17}H_{14}F_2N_2O_7$: 395.07; found: 394.9.

Example 80

1-((3aR,4R,6R,6aR)-2-(6-Methylbenzo[d][1,3]di-oxol-5-yl)-6-methyltetrahydrofuro[3,4-d][1,3]dioxol-4-yl)-5-fluoropyrimidine-2,4(1H,3H)-dione (Compound 180)

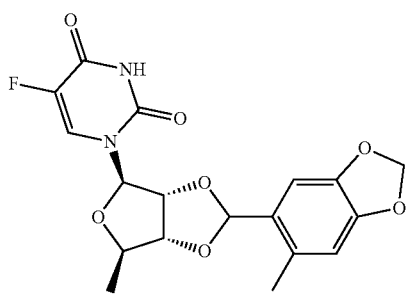

Compound 180 was prepared according to the method described in Scheme II from benzo[d][1,3]dioxole-4-methyl-5-carbaldehyde and capecitabine and isolated as a 3:2 mixture of two stereoisomers. [M−1]⁺ calculated for $C_{17}H_{14}F_2N_2O_7$: 395.07; found: 394.9.

Example 81

1-((2R,3R,4S,5R)-4-(Ethoxymethoxy)-3-hydroxy-5-methyltetrahydrofuran-2-yl)-5-fluoropyrimidine-2,4(1H,3H)-dione (Compound 181)

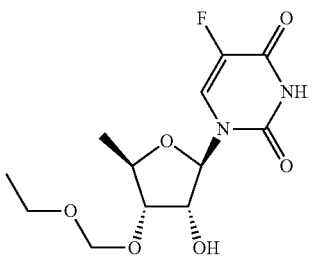 [SMILES: CCOCO[C@H]1[C@@H](O)[C@H](n2cc(F)c(=O)[nH]c2=O)O[C@@H]1C]

Compound 181 was prepared according to the method similar to Scheme I from chloromethyl ethylether and doxifluridine. [M−1]⁺ calculated for $C_{12}H_{17}FN_2O_6$: 303.10; found: 303.0.

Example 82

1-((2R,3R,4S,5R)-3-(Ethoxymethoxy)-4-hydroxy-5-methyltetrahydrofuran-2-yl)-5-fluoropyrimidine-2,4(1H,3H)-dione (Compound 182)

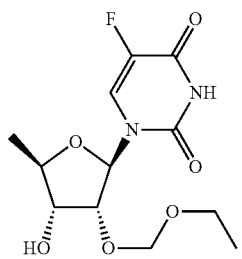 [SMILES: CCOCO[C@@H]1[C@H](O)[C@@H](C)O[C@H]1n1cc(F)c(=O)[nH]c1=O]

Compound 182 was isolated from the reaction described in Example 49. [M−1]⁺ calculated for $C_{12}H_{17}FN_2O_6$: 303.10; found: 303.0.

Example 101

5-Fluoro-1-((4aR,6R,7aS)-2-(heptyloxy)-2-oxidotet-rahydro-4H-furo[3,2-d][1,3,2]dioxaphosphinin-6-yl)pyrimidine-2,4(1H,3H)-dione (Compound 201)

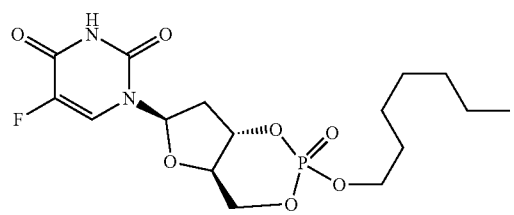

Compound 201 was prepared according to the method described in Scheme I from N,N,N',N'-tetraisopropyl-1-heptyloxyphosphanediamine and floxuridine, and isolated as a mixture of two isomers. [M−1]+ calculated for $C_{16}H_{24}FN_2O_7P$: 405.12; found: 405.0.

Example 102

5-Fluoro-1-((4aR,6R,7aS)-2-(octyloxy)-2-oxidotetrahydro-4H-furo[3,2-d][1,3,2]dioxaphosphinin-6-yl)pyrimidine-2,4(1H,3H)-dione (Compound 202)

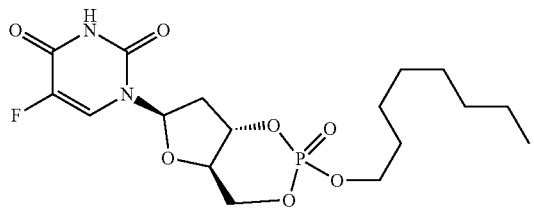

Compound 202 was prepared according to the method described in Scheme I from N,N,N',N'-tetraisopropyl-1-octyloxyphosphanediamine and floxuridine, and isolated as a mixture of two isomers. [M−1]+ calculated for $C_{17}H_{26}FN_2O_7P$: 419.14; found: 419.0.

Example 103

5-Fluoro-1-((4aR,6R,7aS)-2-(6-methylheptyloxy)-2-oxidotetrahydro-4H-furo[3,2-d][1,3,2]dioxaphosphinin-6-yl)pyrimidine-2,4(1H,3H)-dione (Compound 203)

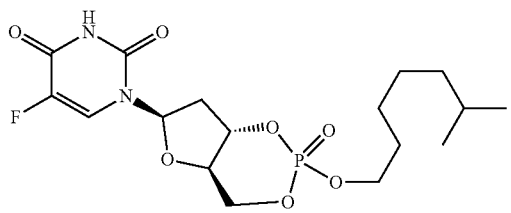

Compound 203 was prepared according to the method described in Scheme I from N,N,N',N'-tetraisopropyl-1-(6-methylheptyloxy)phosphanediamine and floxuridine, and isolated as a mixture of two isomers. [M−1]+ calculated for $C_{17}H_{26}FN_2O_7P$: 419.14; found: 419.0.

Example 104

5-Fluoro-1-((4aR,6R,7aS)-2-(cyclopropylmethyloxy)-2-oxidotetrahydro-4H-furo[3,2-d][1,3,2]dioxaphosphinin-6-yl)pyrimidine-2,4(1H,3H)-dione (Compound 204)

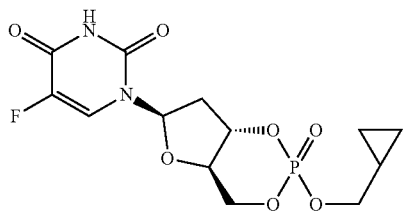

Compound 204 was prepared according to the method described in Scheme I from N,N,N',N'-tetraisopropyl-1-(cyclopropylmethyloxy)phosphanediamine and floxuridine, and isolated as a mixture of two isomers. [M−1]+ calculated for $C_{13}H_{16}FN_2O_7P$: 361.06; found: 361.0.

Example 105

5-Fluoro-1-((4aR,6R,7aS)-2-(cyclopentylmethyloxy)-2-oxidotetrahydro-4H-furo[3,2-d][1,3,2]dioxaphosphinin-6-yl)pyrimidine-2,4(1H,3H)-dione (Compound 205)

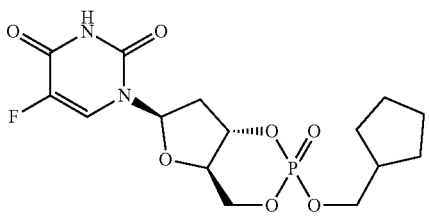

Compound 205 was prepared according to the method described in Scheme I from N,N,N',N'-tetraisopropyl-1-(cyclopentylmethyloxy)phosphanediamine and floxuridine, and isolated as a mixture of two isomers. [M−1]+ calculated for $C_{15}H_{20}FN_2O_7P$: 389.09; found: 389.0.

Example 106

5-Fluoro-1-((4aR,6R,7aS)-2-(2-cyclopentylethyloxy)-2-oxidotetrahydro-4H-furo[3,2-d][1,3,2]dioxaphosphinin-6-yl)pyrimidine-2,4(1H,3H)-dione (Compound 206)

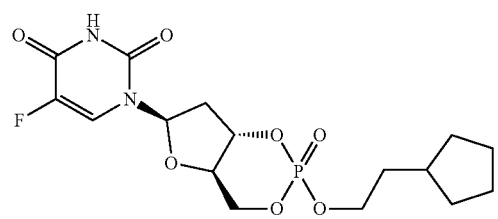

Compound 206 was prepared according to the method described in Scheme I from N,N,N',N'-tetraisopropyl-1-(2-cyclopentylethyloxy)phosphanediamine and floxuridine, and isolated as a mixture of two isomers. [M−1]+ calculated for $C_{16}H_{22}FN_2O_7P$: 403.10; found: 403.0.

Example 107

5-Fluoro-1-((4aR,6R,7aS)-2-(3-cyclopentylpropy-loxy)-2-oxidotetrahydro-4H-furo[3,2-d][1,3,2]dioxa-phosphinin-6-yl)pyrimidine-2,4(1H,3H)-dione (Compound 207)

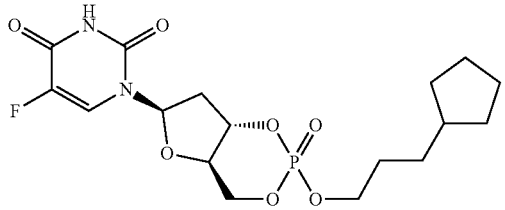

Compound 207 was prepared according to the method described in Scheme I from N,N,N',N'-tetraisopropyl-1-(3-cyclopentylpropyloxy)phosphanediamine and floxuridine, and isolated as a mixture of two isomers. [M+1]$^+$ calculated for $C_{17}H_{24}FN_2O_7P$: 419.14; found: 419.1.

Example 108

5-Fluoro-1-((4aR,6R,7aS)-2-(2-methoxybenzyloxy)-2-oxidotetrahydro-4H-furo[3,2-d][1,3,2]dioxaphos-phinin-6-yl)pyrimidine-2,4(1H,3H)-dione (Compound 208)

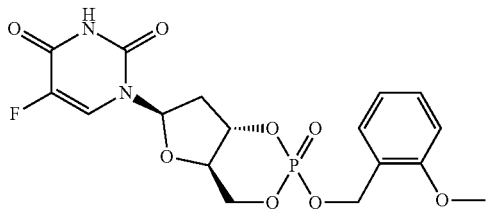

Compound 208 was prepared according to the method described in Scheme I from N,N,N',N'-tetraisopropyl-1-(2-methoxybenzyloxy)phosphanediamine and floxuridine, and isolated as a mixture of two isomers. [M–1]$^+$ calculated for $C_{17}H_{18}FN_2O_8P$: 427.07; found: 427.0.

Example 109

5-Fluoro-1-((4aR,6R,7aS)-2-(4-fluorophenethoxy)-2-oxidotetrahydro-4H-furo[3,2-d][1,3,2]dioxaphos-phinin-6-yl)pyrimidine-2,4(1H,3H)-dione (Compound 209)

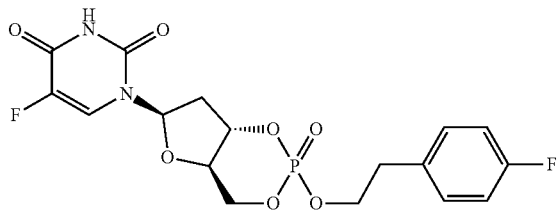

Compound 209 was prepared according to the method described in Scheme I from N,N,N',N'-tetraisopropyl-1-(4-fluorophenethoxy)phosphanediamine and floxuridine, and isolated as a mixture of two isomers. [M–1]$^+$ calculated for $C_{17}H_{17}F_2N_2O_8P$: 429.06; found: 429.0.

Example 110

5-Fluoro-1-((4aR,6R,7aS)-2-(3-fluorophenethoxy)-2-oxidotetrahydro-4H-furo[3,2-d][1,3,2]dioxaphos-phinin-6-yl)pyrimidine-2,4(1H,3H)-dione (Compound 210)

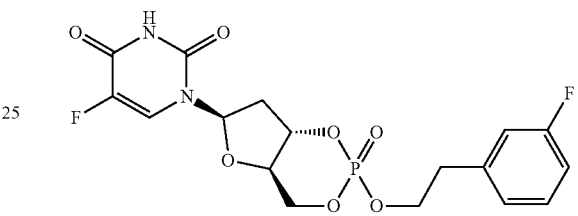

Compound 210 was prepared according to the method described in Scheme I from N,N,N',N'-tetraisopropyl-1-(3-fluorophenethoxy)phosphanediamine and floxuridine, and isolated as a mixture of two isomers. [M–1]$^+$ calculated for $C_{17}H_{17}F_2N_2O_8P$: 429.06; found: 429.0.

Example 111

5-Fluoro-1-((4aR,6R,7aS)-2-(2,4-difluoro-phenethoxy)-2-oxidotetrahydro-4H-furo[3,2-d][1,3,2]dioxaphosphinin-6-yl)pyrimidine-2,4(1H,3H)-dione (Compound 211)

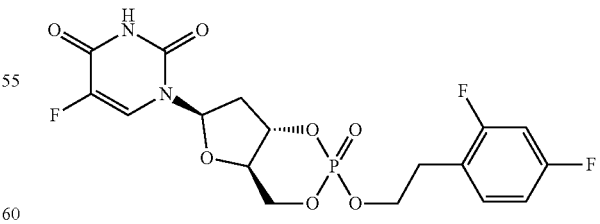

Compound 211 was prepared according to the method described in Scheme I from N,N,N',N'-tetraisopropyl-1-(2,4-difluorophenethoxy)phosphanediamine and floxuridine, and isolated as a mixture of two isomers. [M–1]$^+$ calculated for $C_{17}H_{16}F_3N_2O_8P$: 447.05; found: 447.0.

Example 112

5-Fluoro-1-((4aR,6R,7aS)-2-(4-methylphenethoxy)-2-oxidotetrahydro-4H-furo[3,2-d][1,3,2]dioxaphosphinin-6-yl)pyrimidine-2,4(1H,3H)-dione (Compound 212)

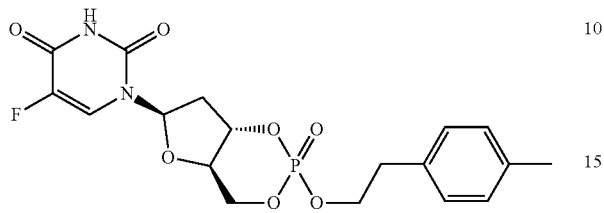

Compound 212 was prepared according to the method described in Scheme I from N,N,N',N'-tetraisopropyl-1-(4-methylphenethoxy)phosphanediamine and floxuridine, and isolated as a mixture of two isomers. [M−1]+ calculated for $C_{18}H_{20}FN_2O_8P$: 425.09; found: 425.1.

Example 113

5-Fluoro-1-((4aR,6R,7aS)-2-(2-fluorophenethoxy)-2-oxidotetrahydro-4H-furo[3,2-d][1,3,2]dioxaphosphinin-6-yl)pyrimidine-2,4(1H,3H)-dione (Compound 213)

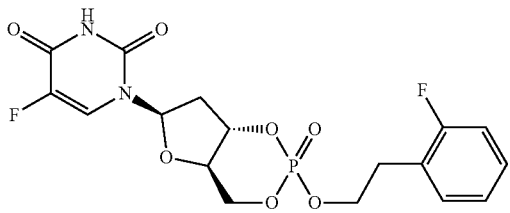

Compound 213 was prepared according to the method described in Scheme I from N,N,N',N'-tetraisopropyl-1-(2-fluorophenethoxy)phosphanediamine and floxuridine, and isolated as a mixture of two isomers. [M−1]+ calculated for $C_{17}H_{17}F_2N_2O_8P$: 429.06; found: 429.1.

Example 114

5-Fluoro-1-((4aR,6R,7aS)-2-(2,6-difluorophenethoxy)-2-oxidotetrahydro-4H-furo[3,2-d][1,3,2]dioxaphosphinin-6-yl)pyrimidine-2,4(1H,3H)-dione (Compound 214)

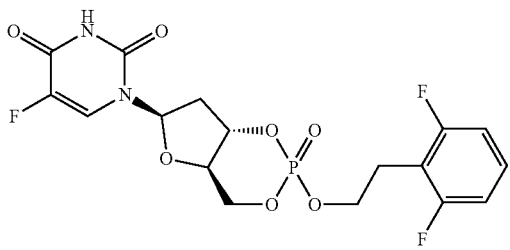

Compound 214 was prepared according to the method described in Scheme I from N,N,N',N'-tetraisopropyl-1-(2,6-difluorophenethoxy)phosphanediamine and floxuridine, and isolated as a mixture of two isomers. [M−1]+ calculated for $C_{17}H_{16}F_3N_2O_8P$: 447.05; found: 447.1.

Example 115

5-Fluoro-1-((4aR,6R,7aS)-2-(2,4,6-trifluorophenethoxy)-2-oxidotetrahydro-4H-furo[3,2-d][1,3,2]dioxaphosphinin-6-yl)pyrimidine-2,4(1H,3H)-dione (Compound 215)

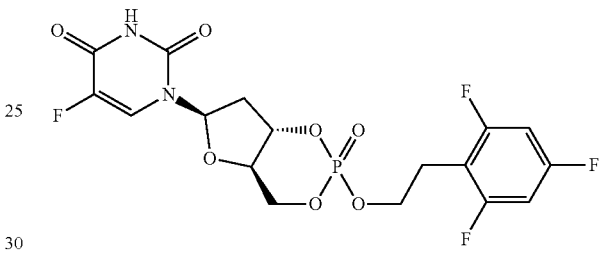

Compound 215 was prepared according to the method described in Scheme I from N,N,N',N'-tetraisopropyl-1-(2,4,6-trifluorophenethoxy)phosphanediamine and floxuridine, and isolated as a mixture of two isomers. [M−1]+ calculated for $C_{17}H_{15}F_4N_2O_8P$: 465.05; found: 465.0.

Example 116

5-Fluoro-1-((4aR,6R,7aS)-2-(4-fluoro-2-methylbenzyloxy)-2-oxidotetrahydro-4H-furo[3,2-d][1,3,2]dioxaphosphinin-6-yl)pyrimidine-2,4(1H,3H)-dione (Compound 216)

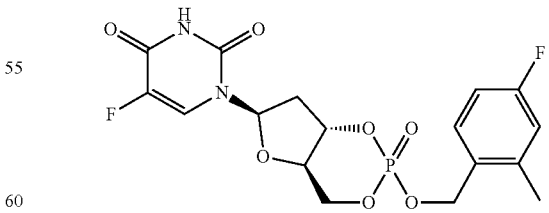

Compound 216 was prepared according to the method described in Scheme I from N,N,N',N'-tetraisopropyl-1-(2-methoxybenzyloxy)phosphanediamine and floxuridine, and isolated as a mixture of two isomers. [M−1]+ calculated for $C_{17}H_{17}F_2N_2O_8P$: 429.06; found: 429.1.

Example 117

5-Fluoro-1-((4aR,6R,7aS)-2-oxido-2-((1-phenylcyclopropyl)methoxy)tetrahydro-4H-furo[3,2-d][1,3,2]dioxaphosphinin-6-yl)pyrimidine-2,4(1H,3H)-dione (Compound 217)

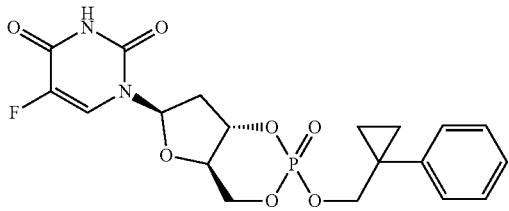

Compound 217 was prepared according to the method described in Scheme I from N,N,N',N'-tetraisopropyl-1-((1-phenylcyclopropyl)methoxy)phosphanediamine and floxuridine, and isolated as a mixture of two isomers. [M−1]+ calculated for $C_{19}H_{20}FN_2O_7P$: 437.09; found: 437.1.

Example 118

1-((4aR,6R,7aS)-2-((2-(Diethoxymethyl)benzyl)oxy)-2-oxidotetrahydro-4H-furo[3,2-d][1,3,2]dioxaphosphinin-6-yl)-5-fluoropyrimidine-2,4(1H,3H)-dione (Compound 218)

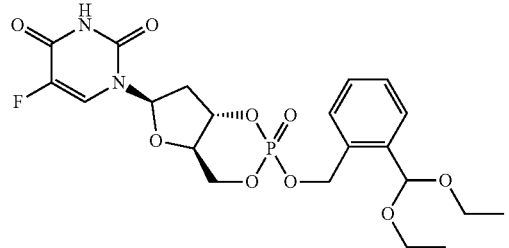

Compound 218 was prepared according to the method described in Scheme I from N,N,N',N'-tetraisopropyl-1-((2-diethoxymethyl)benzyloxy)phosphanediamine and floxuridine, and isolated as a mixture of two isomers. [M−1]+ calculated for $C_{21}H_{26}FN_2O_9P$: 499.13; found: 499.0.

Example 119

1-((4aR,6R,7aS)-2-((2-(1,3-Dioxolan-2-yl)-4-fluorobenzyl)oxy)-2-oxidotetrahydro-4H-furo[3,2-d][1,3,2]dioxaphosphinin-6-yl)-5-fluoropyrimidine-2,4(1H,3H)-dione (Compound 219)

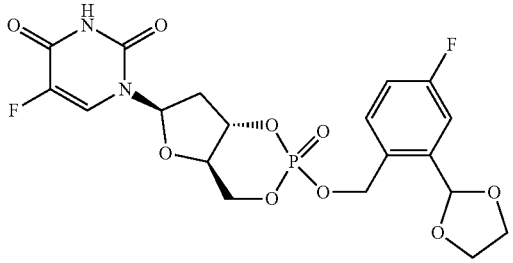

Compound 219 was prepared according to the method described in Scheme I from N,N,N',N'-tetrasopropyl-1-((2-(1,3-dioxolan-2-yl)-4-fluorobenzyloxy)phosphanediamine and floxuridine, and isolated as a mixture of two isomers. [M−1]+ calculated for $C_{19}H_{19}F_2N_2O_9P$: 487.07; found: 487.0.

Example 120

5-Fluoro-1-((4aR,6R,7aS)-2-(3-phenylpropyloxy)-2-oxidotetrahydro-4H-furo[3,2-d][1,3,2]dioxaphosphinin-6-yl)pyrimidine-2,4(1H,3H)-dione (Compound 220)

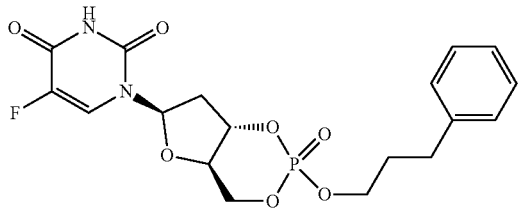

Compound 220 was prepared according to the method described in Scheme I from N,N,N',N'-tetraisopropyl-1-(3-phenylpropyloxy)phosphanediamine and floxuridine, and isolated as a mixture of two isomers. [M+1]+ calculated for $C_{18}H_{20}FN_2O_{7P}$: 425.09; found: 425.1.

Example 121

5-Fluoro-1-((4aR,6R,7aS)-2-(3-(2-fluorophenyl)propyloxy)-2-oxidotetrahydro-4H-furo[3,2-d][1,3,2]dioxaphosphinin-6-yl)pyrimidine-2,4(1H,3H)-dione (Compound 221)

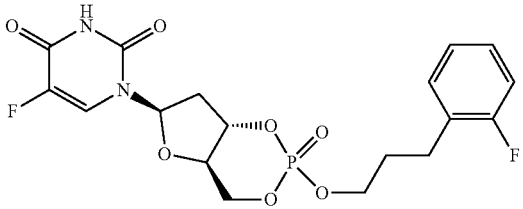

Compound 221 was prepared according to the method described in Scheme I from N,N,N',N'-tetraisopropyl-1-(3-(2-fluorophenyl)propyloxy)phosphanediamine and floxuridine, and isolated as a mixture of two isomers. [M+1]+ calculated for $C_{18}H_{19}F_2N_2O_7P$: 443.08; found: 443.0.

Example 122

5-Fluoro-1-((4aR,6R,7aS)-2-(3-(4-fluorophenyl)propyloxy)-2-oxidotetrahydro-4H-furo[3,2-d][1,3,2]dioxaphosphinin-6-yl)pyrimidine-2,4(1H,3H)-dione (Compound 222)

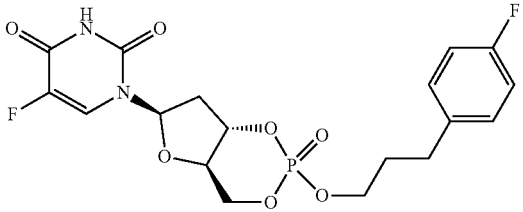

Compound 222 was prepared according to the method described in Scheme I from N,N,N',N'-tetraisopropyl-1-(3-(4-fluorophenyl)propyloxy)phosphanediamine and floxuridine, and isolated as a mixture of two isomers. [M+1]+ calculated for $C_{18}H_{19}F_2N_2O_7P$: 443.08; found: 443.0.

Example 123

1-((4aR,6R,7aS)-2-(4,4-Dipropoxybutoxy)-2-oxido-tetrahydro-4H-furo[3,2-d][1,3,2]dioxaphosphinin-6-yl)-5-fluoropyrimidine-2,4(1H,3H)-dione (Compound 223)

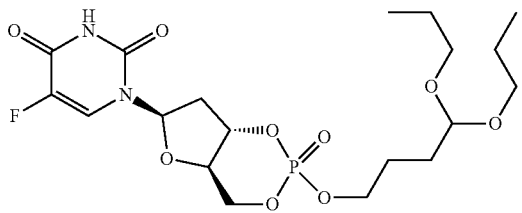

Compound 223 was prepared according to the method described in Scheme I from N,N,N',N'-tetraisopropyl-1-(4,4-bis-(propyloxy)butyloxy)phosphanediamine and floxuridine, and isolated as a mixture of two isomers. [M+1]+ calculated for $C_{19}H_{30}FN_2O_9P$: 479.16; found: 479.0.

BIOLOGICAL EXAMPLES

Examples of use of the method include the following. It will be understood that the following are examples and that the method is not limited solely to these examples.

Example 124: Tissue Distribution Following Oral Administration of Reference Compounds and the Disclosed Compounds The liver specificity of the disclosed compounds is compared relative to a corresponding active compound in liver and other organs that could be targets of toxicity.
Methods:
Reference compounds and the cyclic deoxyribonucleotide, acetal, and hemiaminal compounds are administered at 5-50 mg/kg to fasted rats by oral gavage. Plasma concentrations of the metabolites, and parent compounds in circulation and in the hepatic portal vein are determined by HPLC-UV, and the liver, small intestine, and other organ concentrations are measured by LC-MS using the standard chromatography method.
Results:
Table 1 provides the results of selected compounds, which demonstrated the liver targeting of the acetal and hemiaminal compounds and provide evidence for improved efficiency of the compounds over other types of compounds in liver-targeting and achieving high level of the active in the liver. This can occur solely by the high efficiency liver targeting provided by the acetal and hemiaminal compounds.

Table 1. Drug and metabolite levels in the liver and blood 1 hour after oral administration of selected compounds at 5 mg/kg dose in rats

| Compound | Drug$_{liver}$ (ng/g) | Drug$_{blood}$ (ng/mL) | Met$_{liver}$ (ng/g) | Met$_{blood}$ (ng/g) |
|---|---|---|---|---|
| 109 | 373 | 83.9 | 49.8 | 122 |
| 116 | 978 | 1,346 | 147 | 427 |
| 118 | 1,224 | 3,680 | 62.3 | 158 |

-continued

| Compound | Drug$_{liver}$ (ng/g) | Drug$_{blood}$ (ng/mL) | Met$_{liver}$ (ng/g) | Met$_{blood}$ (ng/g) |
|---|---|---|---|---|
| 122 | 1,980 | 301 | 109 | 3.73 |
| 127 | <6 | 7.81 | 1,141 | 47.9 |
| 132 | 1,366 | 59.9 | 327 | <4 |
| 139 | <6 | 11.3 | 1,534 | 34.0 |
| 147 | <6 | <1 | 135 | 1.96 |
| 156 | <6 | 3.66 | 661 | 14.6 |

Table 2 provides the results of selected cyclic deoxyribonucleotide compounds demonstrating liver-targeting.

TABLE 2

Prodrug and metabolite levels in the liver and blood 1 hour after oral administration of reference and selected compounds at 5 mg/kg dose in rats

| Compound | Drug$_{liver}$ (ng/g) | Drug$_{blood}$ (ng/mL) | FdUMP$_{liver}$ (ng/g) | FUDR$_{blood}$ (ng/mL) | FdUMP$_{liver}$/FUDR$_{blood}$ |
|---|---|---|---|---|---|
| Capecitabine | 44.7 | 88.4 | <12 | <3 | <10 |
| NUC-3373 | <6 | <1 | 54.8 | 11.4 | 4.8 |
| 201 | 1,042 | 109 | 894 | 18.3 | 49 |
| 202 | 2,562 | 158 | 551 | 4.9 | 112 |
| 207 | 429 | 29.4 | 324 | 8.4 | 39 |
| 217 | 255 | 21.7 | 909 | 13.9 | 65 |
| 219 | 49.9 | 20 | 842 | 12.2 | 69 |
| 220 | 944 | 122 | 1,508 | 22.1 | 68 |

FdUMP = Floxuridine monophosphate;
FUDR = Floxuridine;
Capecitabine = Active ingredient of Xeloda, a prodrug;
NUC-3373 = ProTide prodrug developed by NuCana PLC.

FdUMP=Floxuridine monophosphate; FUDR=Floxuridine; Capecitabine=Active ingredient of Xeloda, a prodrug; NUC-3373=ProTide prodrug developed by NuCana PLC.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15%, 10%, 5%, 3%, 1%, 0.1%, or otherwise. Similarly, in certain embodiments, the terms "generally perpendicular" and "substantially perpendicular" refer to a value, amount, or characteristic that departs from exactly perpendicular by less than or equal to 15%, 10%, 5%, 3%, 1%, 0.1%, or otherwise.

The above description discloses several methods and materials. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

Although the invention has been described with reference to embodiments and examples, it should be understood that numerous and various modifications can be made without departing from the spirit of the invention. Accordingly, the invention is limited only by the following claims

What is claimed is:
1. A compound of Formula VI:

(VI)

(a)
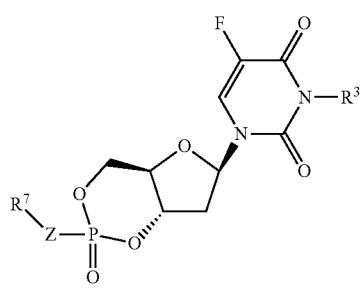

(b)
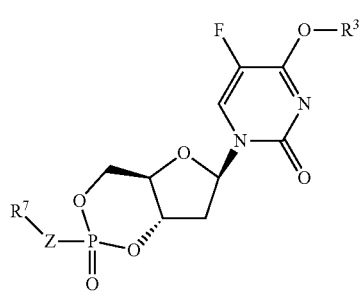

(c)
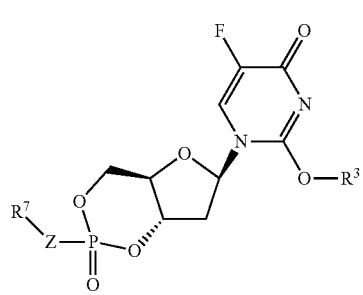

or a diastereomer or a pharmaceutically acceptable salt thereof, wherein $R^3$ is selected from the group consisting of H, an optionally substituted $C_1$-$C_{10}$ alkyl-$OCH_2$—, an optionally substituted $C_1$-$C_{10}$ alkyl-$NHCH_2$—, an optionally substituted $C_1$-$C_{10}$ acyl, an optionally substituted $C_1$-$C_{10}$ alkyl-OC(O)—, an optionally substituted $C_{6-10}$ aryl-$CH_2OCH_2$—, an optionally substituted $C_{6-10}$ aryl-$OCH_2$—, an optionally substituted $C_{6-10}$ aryl-C(O)—, an optionally substituted 5-10 membered heteroaryl-$CH_2OCH_2$—, an optionally substituted 5-10 membered heteroaryl-$OCH_2$—, an optionally substituted $C_{6-10}$ aryl-OC(O)—, an optionally substituted 5-10 membered heteroaryl-C(O)—, and an optionally substituted 5-10 membered heteroaryl-OC(O)—; and $R^7$ is selected from the group consisting of an optionally substituted $C_2$-$C_{20}$ alkyl, an optionally substituted $C_2$-$C_{20}$ alkenyl, an optionally substituted $C_3$-$C_{20}$ cycloalkyl, an optionally substituted $C_{6-10}$ aryl, an optionally substituted 5-10 membered heteroaryl, an optionally substituted $C_1$-$C_{10}$ alkyl-$OCH_2$—, an optionally substituted $C_1$-$C_{10}$ alkyl-CO—$OCH_2$—, an optionally substituted $C_{6-10}$ aryl-$OCH_2$—, an optionally substituted 5-10 membered heteroaryl-$OCH_2$—; an optionally substituted $C_{6-10}$ aryl-$CH_2$—, an optionally substituted 5-10 membered heteroaryl-$CH_2$—, an optionally substituted $C_3$-$C_{10}$-cycloalkenyl-$CH_2$—,

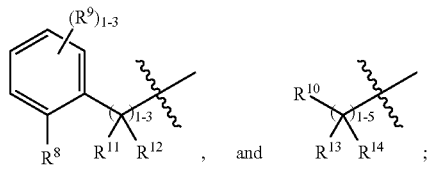

$R^8$ is selected from the group consisting of H, halo, $C_1$-$C_{10}$ alkyl, —O—$C_{1-6}$ alkyl, —$OCH_2OR^{15}$, —CH$(OR^{15})_2$, —C-amido, —$CH_2OCH_2OR^{15}$,

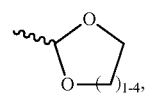

and —$CH_2$O-carboxy;

each $R^9$ is independently selected from the group consisting of H, halo, and $C_1$-$C_{10}$ alkyl;

$R^{10}$ is selected from the group consisting of —O-carboxy, —$OCH_2OR^{15}$, —$CH(OR^{15})_2$, —C-carboxy, —C-amido, —$CH_2OCH_2OR^{15}$,

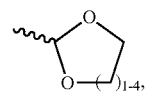

—$CH_2$O-carboxy, $C_1$-$C_{10}$ alkyl, and $C_3$-$C_{10}$ cycloalkyl;

each $R^{11}$ and $R^{12}$ are independently H or $C_1$-$C_{10}$ alkyl; or alternatively, an $R^{11}$ and $R^{12}$ attached to the same carbon atom may be taken together with the atom to which they are attached form a $C_3$-$C_{10}$ cycloalkyl;

each $R^{13}$ and $R^{14}$ are independently H or $C_1$-$C_{10}$ alkyl; or alternatively, an $R^{13}$ and $R^{14}$ attached to the same carbon atom may be taken together with the atom to which they are attached form a $C_3$-$C_{10}$ cycloalkyl;

R¹⁵ is an optionally substituted $C_1$-$C_{10}$ alkyl; and
Z is O;
wherein when a group is described as optionally substituted, the group may be substituted with one or more substituents independently selected from $C_1$-$C_6$ alkyl, $C_2$-$C_6$ alkenyl, $C_2$-$C_6$ alkynyl, $C_3$-$C_7$ carbocyclyl, $C_3$-$C_7$-carbocyclyl-$C_1$-$C_6$-alkyl, 3-10 membered heterocycyl, 3-10 membered heterocycyl-$C_1$-$C_6$-alkyl, aryl, aryl-$C_1$-$C_6$-alkyl, 5-10 membered heteroaryl, 5-10 membered heteroaryl-$C_1$-$C_6$-alkyl, halo, cyano, hydroxy, $C_1$-$C_6$ alkoxy, $C_1$-$C_6$ alkoxy-$C_1$-$C_6$-alkyl, aryloxy, $C_3$-$C_7$ carbocyclyloxy, 3-10 membered heterocyclyl-oxy, 5-10 membered heteroaryl-oxy, $C_3$-$C_7$-carbocyclyl-$C_1$-$C_6$-alkoxy, 3-10 membered heterocyclyl-$C_1$-$C_6$-alkoxy, aryl-$C_1$-$C_6$-alkoxy, 5-10 membered heteroaryl-$C_1$-$C_6$-alkoxy, sulfhydryl, halo-$C_1$-$C_6$-alkyl, halo-$C_1$-$C_6$-alkoxy, $C_1$-$C_6$ alkylthio, arylthio, $C_3$-$C_7$ carbocyclylthio, 3-10 membered heterocyclyl-thio, 5-10 membered heteroaryl-thio, $C_3$-$C_7$-carbocyclyl-$C_1$-$C_6$-alkylthio, 3-10 membered heterocyclyl-$C_1$-$C_6$-alkylthio, aryl-$C_1$-$C_6$-alkylthio, 5-10 membered heteroaryl-$C_1$-$C_6$-alkylthio, amino, amino-$C_1$-$C_6$-alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, $C_2$-$C_{10}$ heteroalkyl, and oxo; wherein when the one or more substituents is selected from the group consisting of $C_3$-$C_7$ carbocyclyl, $C_3$-$C_7$-carbocyclyl-$C_1$-$C_6$-alkyl, 3-10 membered heterocyclyl, 3-10 membered heterocycyl-$C_1$-$C_6$-alkyl, aryl, aryl-$C_1$-$C_6$-alkyl, 5-10 membered heteroaryl, 5-10 membered heteroaryl-$C_1$-$C_6$-alkyl, aryloxy, $C_3$-$C_7$ carbocyclyloxy, 3-10 membered heterocyclyl-oxy, 5-10 membered heteroaryl-oxy, $C_3$-$C_7$-carbocyclyl-$C_1$-$C_6$-alkoxy, 3-10 membered heterocyclyl-$C_1$-$C_6$-alkoxy, aryl-$C_1$-$C_6$-alkoxy, 5-10 membered heteroaryl-$C_1$-$C_6$-alkoxy, arylthio, $C_3$-$C_7$ carbocyclylthio, 3-10 membered heterocyclyl-thio, 5-10 membered heteroaryl-thio, $C_3$-$C_7$-carbocyclyl-$C_1$-$C_6$-alkylthio, 3-10 membered heterocyclyl-$C_1$-$C_6$-alkylthio, aryl-$C_1$-$C_6$-alkylthio, and 5-10 membered heteroaryl-$C_1$-$C_6$-alkylthio, the one or more substituents are optionally substituted with halo, $C_1$-$C_6$ alkyl, $C_1$-$C_6$ alkoxy, $C_1$-$C_6$ haloalkyl, and $C_1$-$C_6$ haloalkoxy; and
wherein heteroaryl is an aromatic ring or aromatic ring system of two or more fused rings containing one or more of nitrogen, oxygen, and sulfur in the ring backbone.

2. The compound of claim 1, wherein R³ is H.

3. The compound of claim 1, wherein Z is O.

4. The compound of claim 1, wherein R⁷ is selected from the group consisting of an optionally substituted $C_2$-$C_{20}$ alkyl, an optionally substituted $C_2$-$C_{20}$ alkenyl, an optionally substituted $C_3$-$C_{20}$ cycloalkyl, an optionally substituted $C_{6-10}$ aryl, an optionally substituted 5-10 membered heteroaryl, an optionally substituted $C_1$-$C_{10}$ alkyl-OCH₂—, an optionally substituted $C_1$-$C_{10}$ alkyl-CO—OCH₂—, an optionally substituted $C_{6-10}$ aryl-OCH₂—, an optionally substituted 5-10 membered heteroaryl-OCH₂—; an optionally substituted $C_{6-10}$ aryl-CH₂—, and an optionally substituted 5-10 membered heteroaryl-CH₂—.

5. The compound of claim 1, wherein R⁷ is an optionally substituted $C_2$-$C_{20}$ alkyl.

6. The compound of claim 1, wherein R⁷ is an optionally substituted $C_{6-10}$ aryl.

7. The compound of claim 1, wherein R⁷ is an optionally substituted $C_{6-10}$ aryl-CH₂—.

8. The compound of claim 1, having the structure:

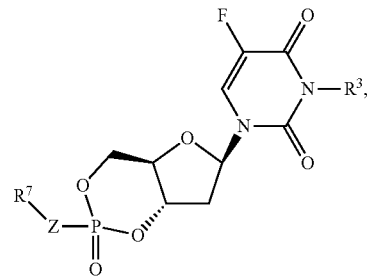

or a diastereomer or a pharmaceutically acceptable salt thereof.

9. The compound of claim 8, wherein R⁷ is

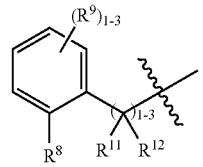

10. The compound of claim 9, wherein:

R⁸ is selected from the group consisting of H, F, $C_1$-$C_{10}$ alkyl, —OMe, —OEt, —OCH₂OR¹⁵, —CH(OR¹⁵)₂, —C-amido, —CH₂OCH₂OR¹⁵,

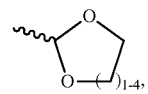

and —CH₂O-carboxy; and

R⁹ is selected from the group consisting of H, F, and $C_1$-$C_{10}$ alkyl.

11. The compound of claim 10, wherein R⁸ is H and R⁹ is H or F.

12. The compound of claim 10, wherein R⁸ is selected from the group consisting of —OMe, —OEt, —OCH₂OR¹⁵, —CH(OR¹⁵)₂, —C-amido, —CH₂OCH₂OR¹⁵,

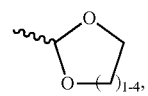

and —CH₂O-carboxy.

13. The compound of claim 10, wherein R⁸ is F.

14. The compound of claim 10, wherein R⁹ is H.

15. The compound of claim 10, wherein R⁹ is F.

16. The compound of claim 8, wherein $R^7$ is
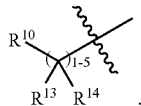
17. The compound of claim 16, wherein $R^{10}$ is selected from the group consisting of —O-carboxy, —OCH$_2$OR$^{15}$, —CH(OR$^{15}$)$_2$, —C-carboxy, —C-amido, —CH$_2$OCH$_2$OR$^{15}$,
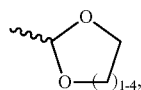
and —CH$_2$O-carboxy.
18. The compound of claim 1, wherein $R^{10}$ is a $C_1$-$C_{10}$ alkyl or a $C_3$-$C_{10}$ cycloalkyl.
19. The compound of claim 1, wherein the compound is selected from:
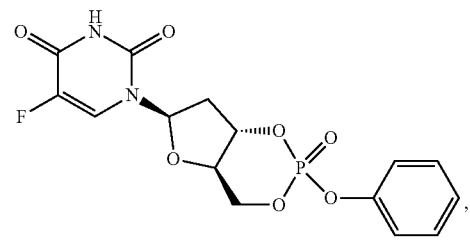
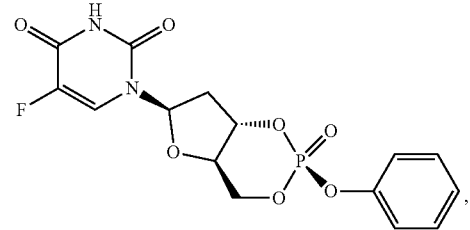
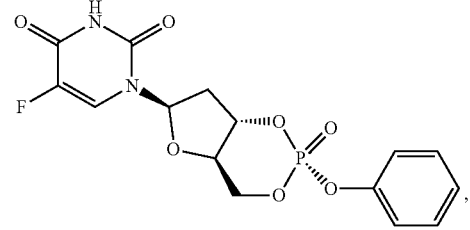
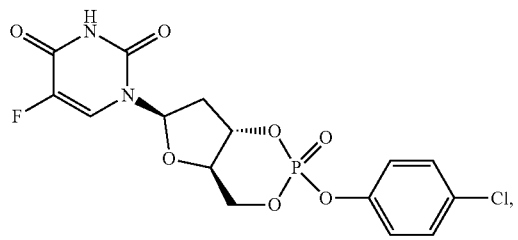
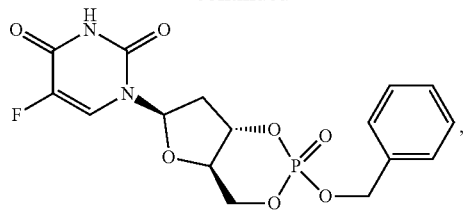
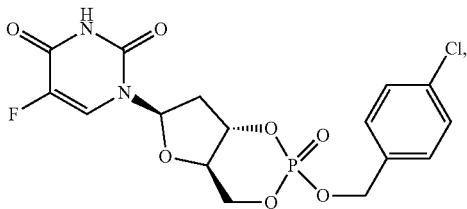
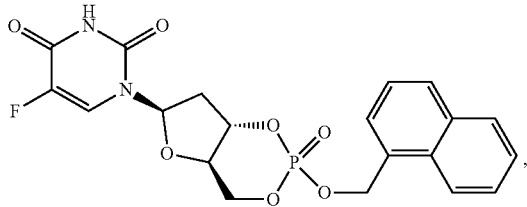
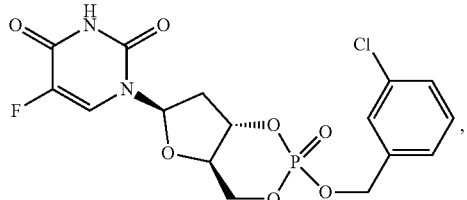
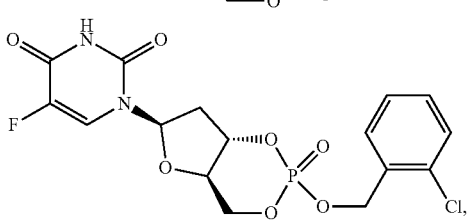
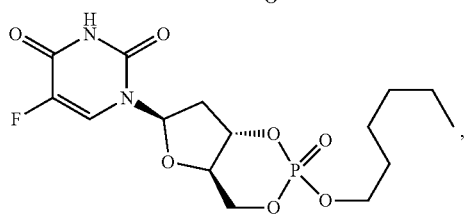
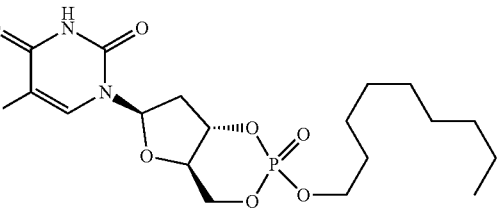
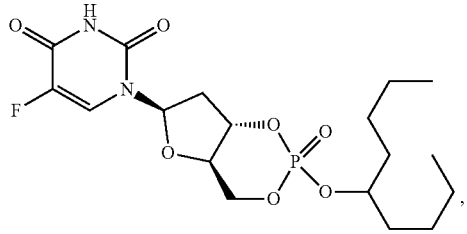

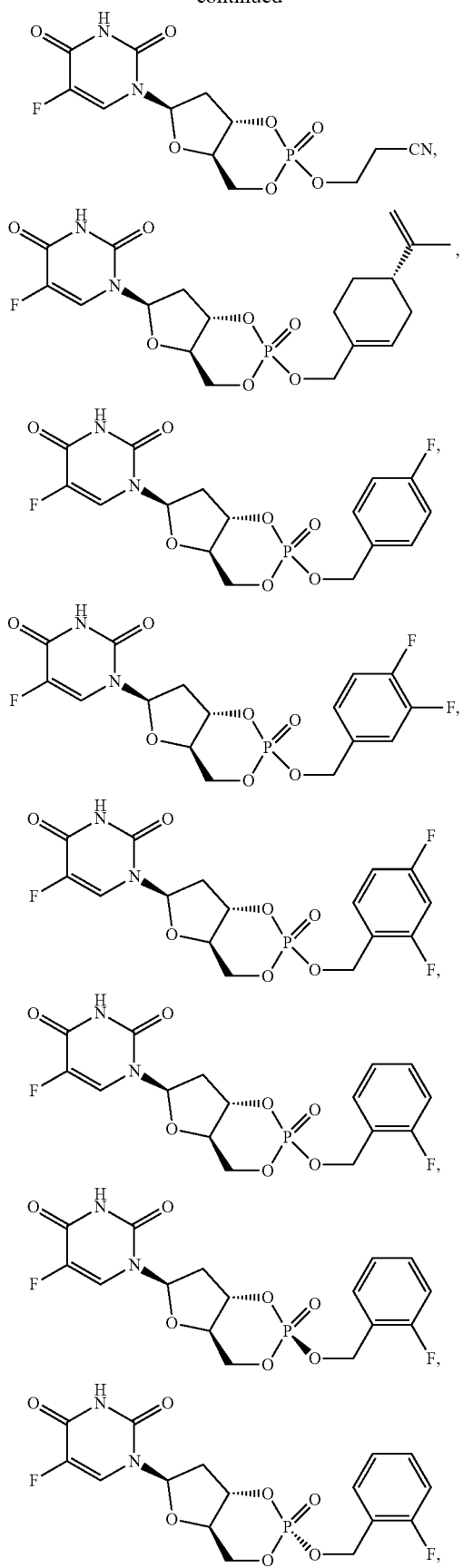
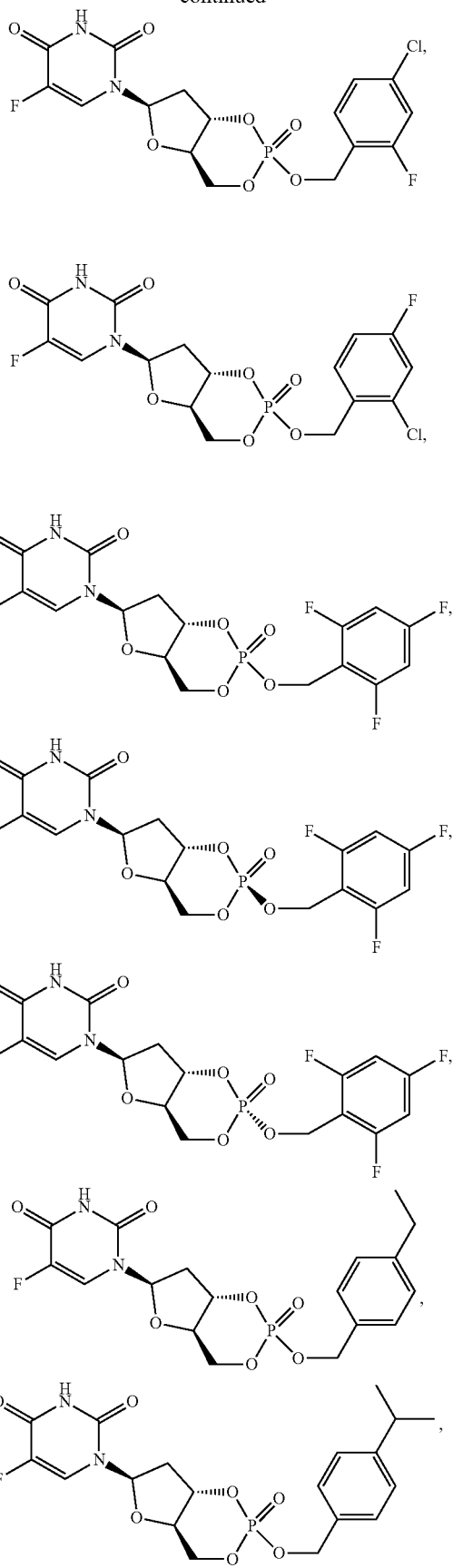

-continued
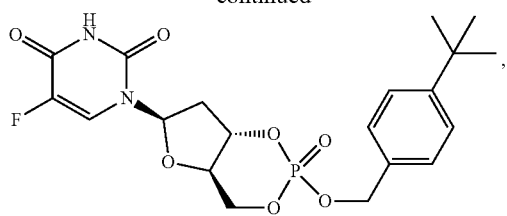
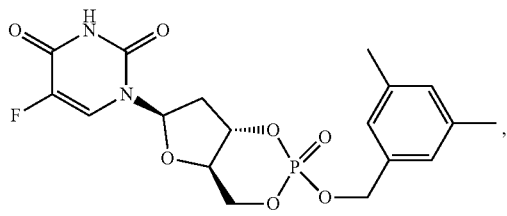
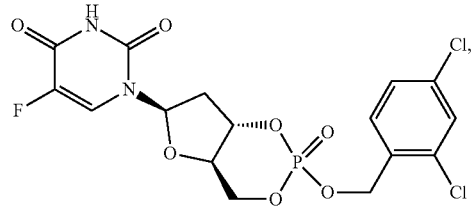
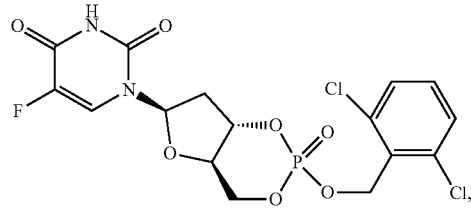
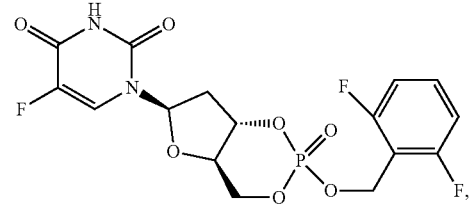
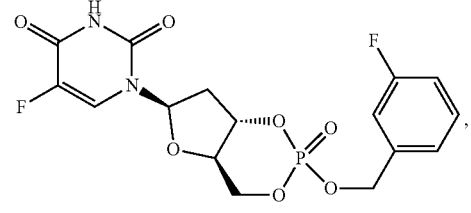
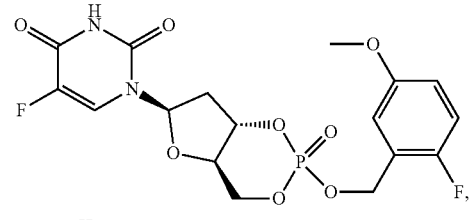
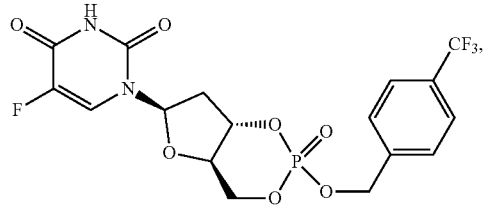
-continued
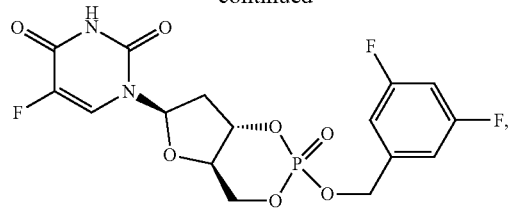
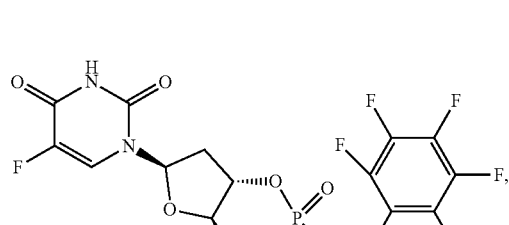
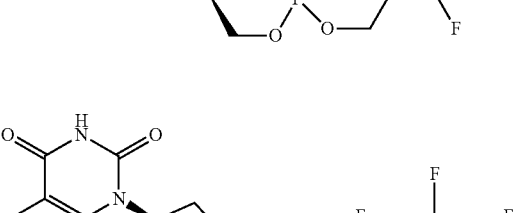
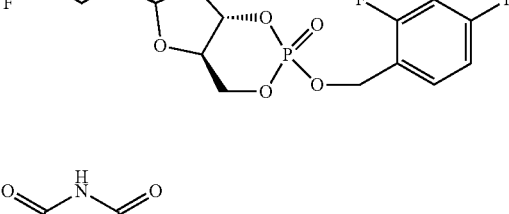
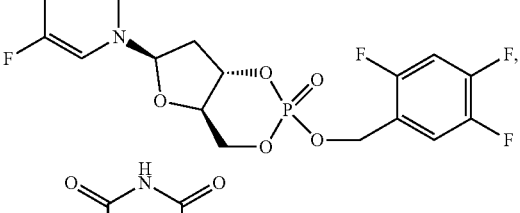
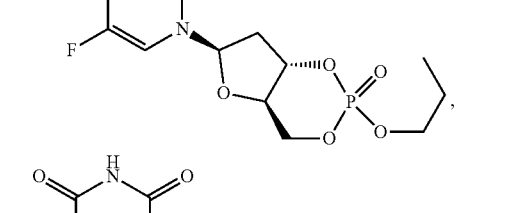
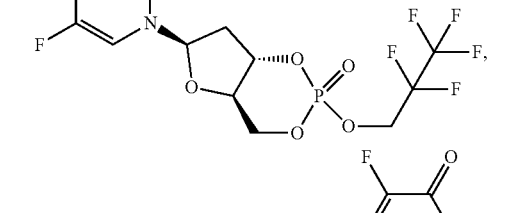
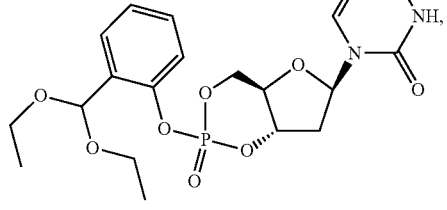

97
-continued
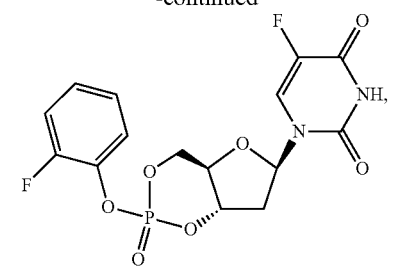
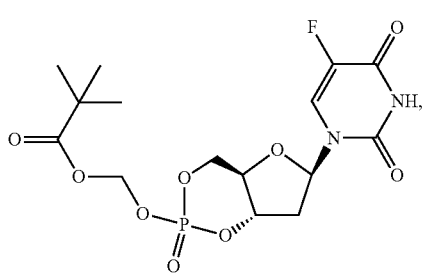
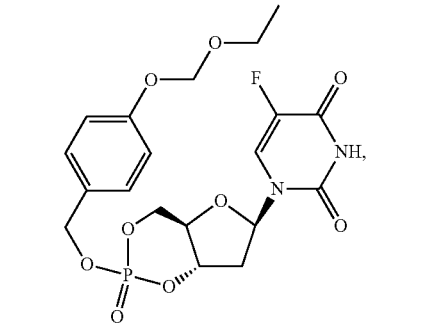
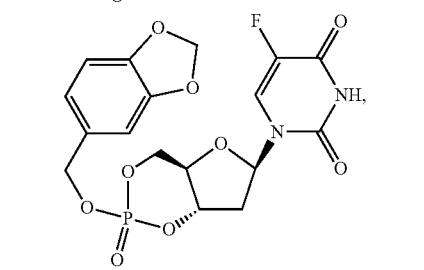
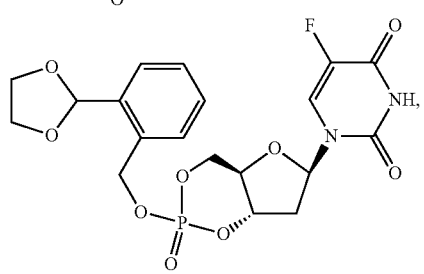
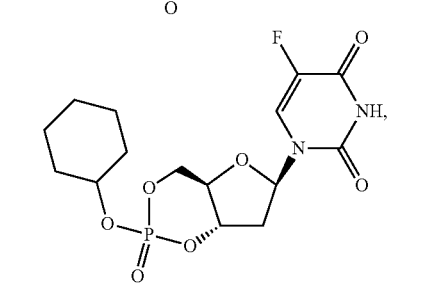
98
-continued
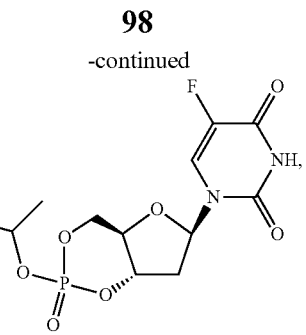
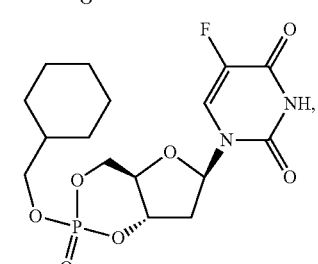
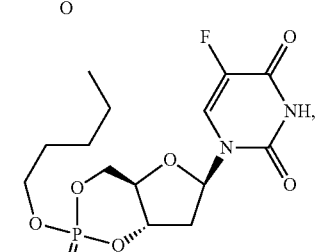
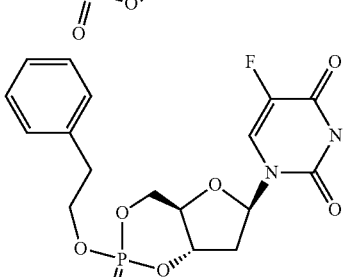
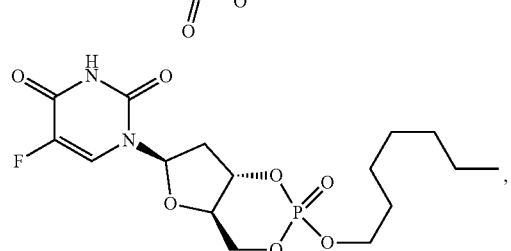
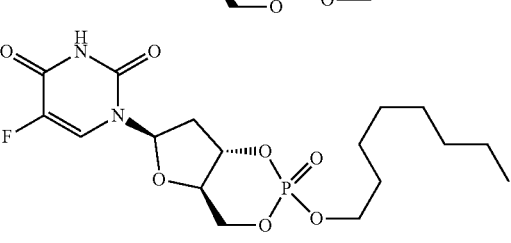
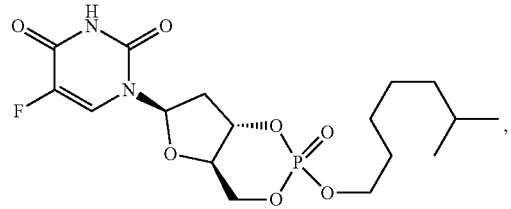

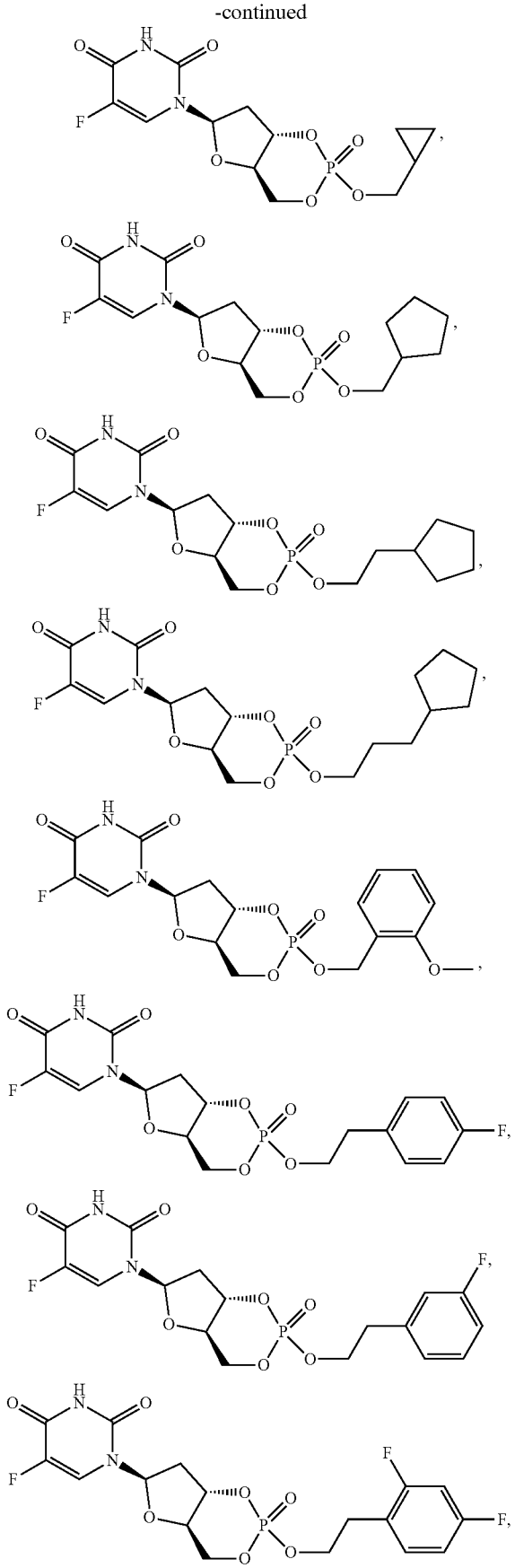
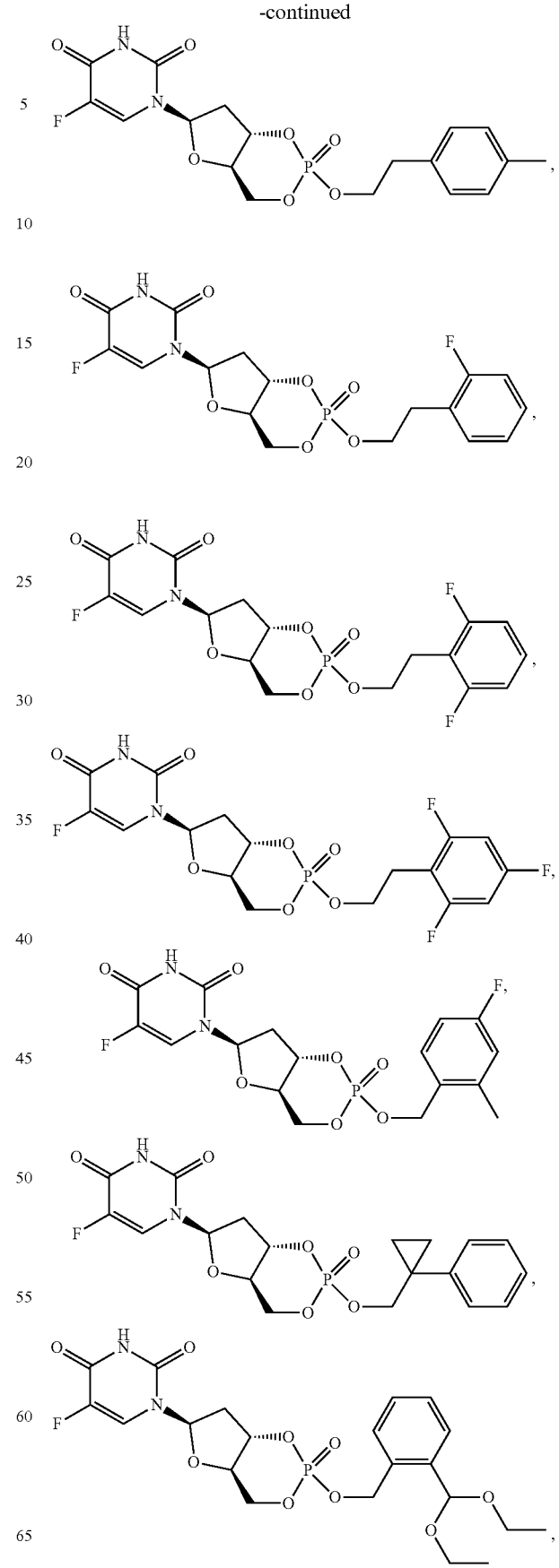

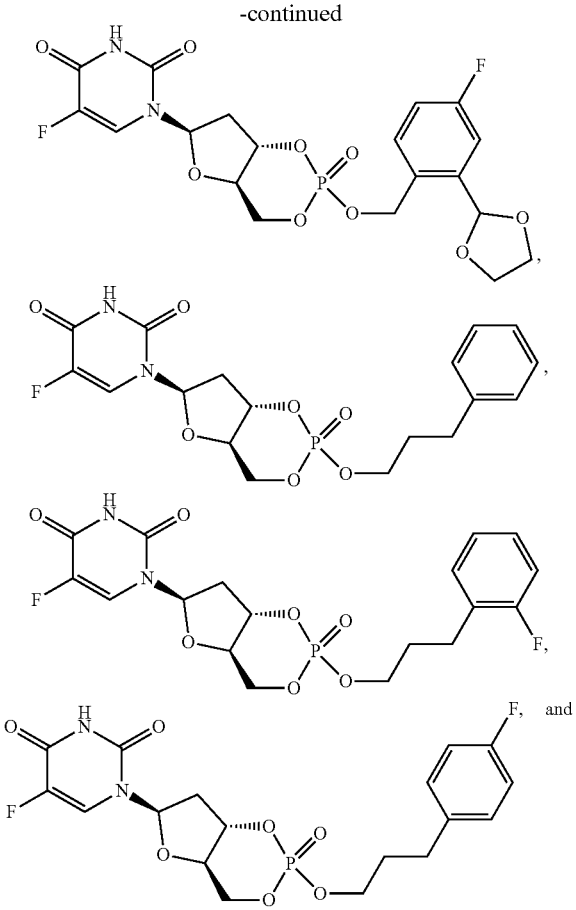

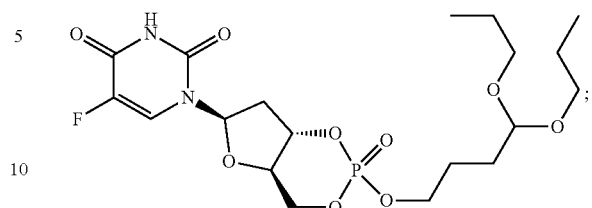

or a diastereomer or a pharmaceutically acceptable salt thereof.

20. A pharmaceutical composition comprising the compound of claim 1 and a pharmaceutically acceptable excipient.

21. A method of treating a disease, disorder or condition comprising administering an effective amount of the compound of claim 1 to a subject in need thereof;

wherein the disease, disorder or condition is a disease, disorder or condition of the liver.

22. A method of treating a disease, disorder or condition comprising administering an effective amount of the compound of claim 1 to a subject in need thereof;

wherein the disease, disorder or condition is selected from the group consisting of hepatocellular carcinoma, kidney cancer, colorectal cancer, breast cancer, stomach cancer, gastric cancer, esophageal cancer, pancreatic cancer, and cervical cancer.

\* \* \* \* \*